(12) United States Patent
Sakai et al.

(10) Patent No.: US 6,590,097 B1
(45) Date of Patent: Jul. 8, 2003

(54) SULFATED FUCOGALACTAN

(75) Inventors: Takeshi Sakai, Hirosaki (JP); Hitomi Kimura, Hirosaki (JP); Kaoru Kojima, Hirosaki (JP); Kaoru Katayama, Otsu (JP); Kazuo Shimanaka, Takatsuki (JP); Katsushige Ikai, Shiga (JP); Ikunoshin Kato, Uji (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/913,599

(22) PCT Filed: Feb. 21, 2000

(86) PCT No.: PCT/JP00/00965
§ 371 (c)(1),
(2), (4) Date: Aug. 16, 2001

(87) PCT Pub. No.: WO00/50464
PCT Pub. Date: Aug. 31, 2000

(30) Foreign Application Priority Data

Feb. 23, 1999 (JP) ............................................ 11-044752
Aug. 19, 1999 (JP) ........................................... 11-232809
Dec. 9, 1999 (JP) ............................................ 11-350112

(51) Int. Cl.⁷ ............................ C08B 37/00; C07H 1/00; C07H 5/10
(52) U.S. Cl. ...................... 536/123.1; 536/4.1; 536/118; 536/119; 536/124; 536/18.5; 568/28
(58) Field of Search ................................ 536/4.1, 123.1, 536/118, 119, 18.5, 124; 568/28

(56) References Cited

U.S. PATENT DOCUMENTS 4,859,769 A * 8/1989 Karlsson et al.
6,054,577 A * 4/2000 Sakai et al.
6,194,192 B1 * 2/2001 Ueno et al.
6,207,652 B1   3/2001 Sakai et al.

OTHER PUBLICATIONS

Masashi Mizuno et al. "Fucogalactan isolated from Sarcodon aspratus elicits release of tumor necrosis factor–α and nitric oxide from murine macrophages", Immunopharmacology 46 (2000) 113–121.

* cited by examiner

Primary Examiner—Samuel Barts
Assistant Examiner—Michael C. Henry
(74) Attorney, Agent, or Firm—Browdy and Neimark, P.L.L.C.

(57) ABSTRACT

Sulfated fucogalactan or its salt useful as a reagent for sugar chain engineering or an HGF-production inducer; a degraded product or its salt obtained by treating the sulfated fucogalactan with a sulfated fucogalactan digesting enzyme; the sulfated fucogalactan digesting enzyme useful in sugar chain engineering; a process for producing the degraded product by treating sulfated fucogalactan or its salt with the above enzyme; and a process for producing the sulfated fucogalactan digesting enzyme.

5 Claims, 27 Drawing Sheets

SULFATED FUCOGALACTAN

REFERENCE TO RELATED APPLICATIONS

The present application is the national stage under 35 U.S.C. §371 of international application PCT/JP00/00965, filed Feb. 21, 2000 which designated the United States, and which application was not published in the English language.

TECHNICAL FIELD

The present invention relates to a sulfated fucogalactan which is useful as a reagent for glycotechnology, a smaller molecule from the sulfated polysaccharide and a method for producing the same, as well as a sulfated fucogalactan-digesting enzyme which is useful in a field of glycotechnology and a method for producing the enzyme.

BACKGROUND ART

Brown algae contain a variety of sulfated-fucose-containing polysaccharides. For example, sulfated-fucose-containing polysaccharides such as (1) sulfated fucans consisting of fucose and sulfate groups; (2) sulfated fucoglucuronomannans containing glucuronic acid, mannose, fucose and sulfate groups, e.g., the sulfated-fucose-containing polysaccharide-U as described in WO 97/26896 (approximate molar ratio of constituting saccharides, fucose: mannose: galactose: uronic acid: sulfate group=10:7:4:5:20; hereinafter referred to as U-fucoidan); and (3) sulfated fucogalactan consisting of fucose and galactose, e.g., the sulfated-fucose-containing polysaccharide-F as described in WO 97/26896 (approximate molar ratio of constituting saccharides, fucose: galactose=10:1; hereinafter referred to as F-fucoidan) are known. Almost all of these sulfated-fucose-containing polysaccharides are macromolecular anions. Therefore, they behave in a chemically and physically similar manner in various purification steps, making it difficult to separate them each other. For this reason, biological activities of sulfated-fucose-containing polysaccharides derived from brown algae have often been examined without separating them each other. Therefore, it was difficult to identify the sulfated-fucose-containing polysaccharide that was responsible for the observed biological activity.

To date, correlation between an activity and a molecule has been known for the sulfated fucan fraction as described in Agricultural and Biological Chemistry, 44(8): 1965–1966 (1980), which is responsible for anticoagulant activity, and U-fucoidan as described in WO 97/26896, which is responsible for an apoptosis-inducing activity against tumor cells.

The use of the sulfated fucan fraction as an anticoagulant in place of heparin has been examined. However, if the sulfated fucan is to be used as a pharmaceutical, it is required to obtain a highly pure sulfated fucan in order to avoid side effects due to unexpected activities. Thus, a method therefor has been desired.

Regarding U-fucoidan, it is similarly required to conveniently obtain a highly pure sulfated-fucose-containing polysaccharide-U in order to prepare a pharmaceutical utilizing the apoptosis-inducing activity against tumor cells. Thus, a method therefor has been desired.

Generally, enzymatic digestion is the most efficient manner utilized for structural analysis of polysaccharides and production of oligosaccharides. Furthermore, only one polysaccharide can be readily removed from a mixture of polysaccharides which are hardly separated each other as follows. The polysaccharide to be removed is converted into smaller molecules by digesting it with an enzyme that specifically digests the polysaccharide. The mixture is then subjected to molecular weight fractionation such as ultrafiltration.

If an enzyme that specifically digests a sulfated fucogalactan is available, structural analysis of the sulfated fucogalactan and production of a sulfated fucogalactan oligosaccharide are readily conducted.

As described above, a sulfated fucogalactan-digesting enzyme and a method for enzymatically producing a sulfated fucogalactan oligosaccharide have been desired.

OBJECTS OF INVENTION

Thus, the main object of the present invention is to provide (1) a sulfated fucogalactan or a salt thereof which is useful as a reagent for glycotechnology or an inducer of hepatocyte growth factor (HGF) production; (2) a smaller molecule obtained by allowing a sulfated fucogalactan-digesting enzyme to act on a sulfated fucogalactan, or a salt thereof; (3) a sulfated fucogalactan-digesting enzyme which is useful for glycotechnology; (4) a method for producing a smaller molecule obtained by allowing said enzyme to act on a sulfated fucogalactan or a salt thereof; and (5) a method for producing a sulfated fucogalactan-digesting enzyme.

SUMMARY OF INVENTION

As a result of intensive study, the present inventors have found a sulfated fucogalactan contained in brown algae, a sulfated fucogalactan-digesting enzyme that digests the sulfated polysaccharide and a method for producing the same. Furthermore, the present inventors have found a smaller molecule from a sulfated fucogalactan which can be utilized as a reagent for glycotechnology and a method for producing the same, thereby completing the present invention.

The first aspect of the present invention relates to a sulfated fucogalactan having the following chemical and physical properties or a salt thereof. The sulfated fucogalactan contains galactose and fucose as constituting saccharides at a molar ratio of 1:1 to 6:1 and contains a sulfated saccharide of general formula (XI) as an essential component of the constituting saccharides:

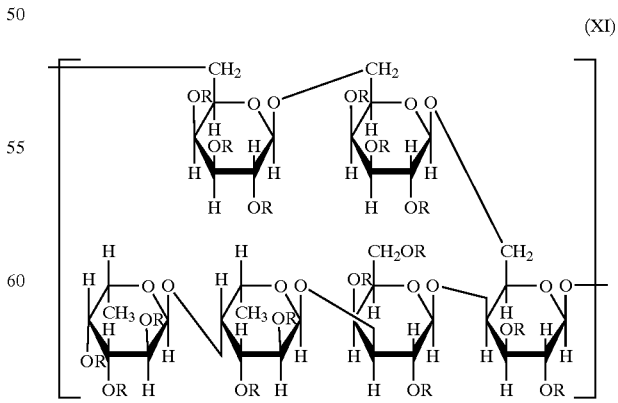

wherein R is H or $SO_3H$.

Furthermore, the sulfated fucogalactan is converted into smaller molecules by a sulfated fucogalactan-digesting enzyme of the present invention to generate at least one compound selected from the group consisting of the compounds of general formulas (I) to (IV):

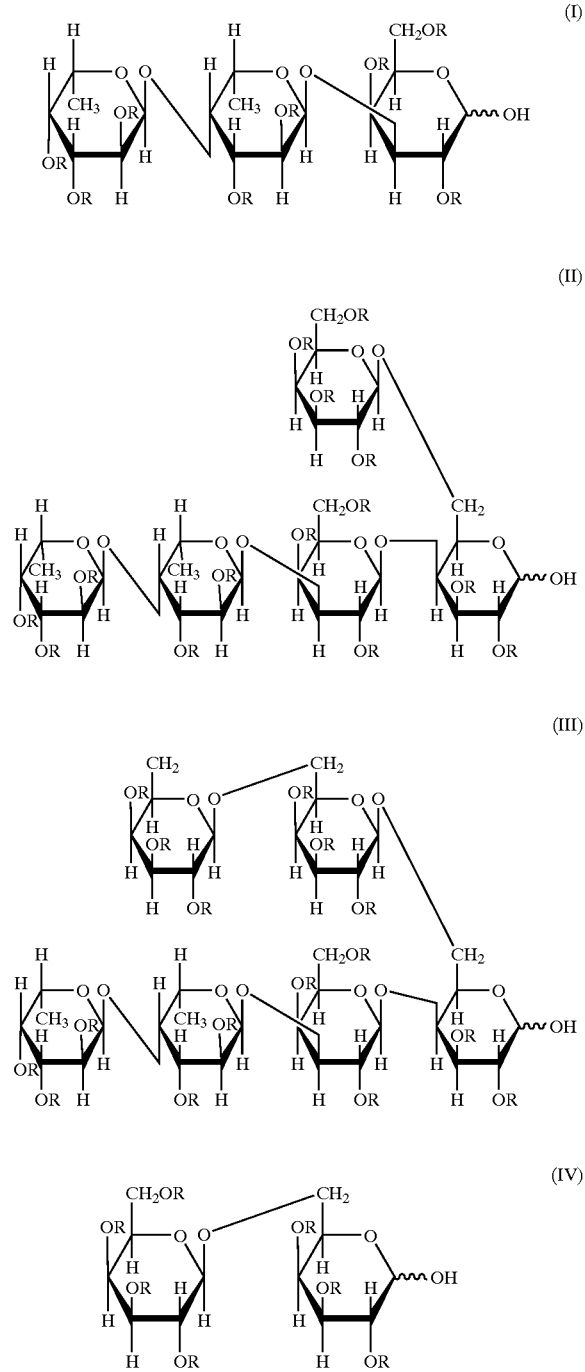

wherein R is H or SO₃H.

The second aspect of the present invention relates to a saccharide having a chemical structure selected from the group consisting of general formulas (II), (III') and (IV):

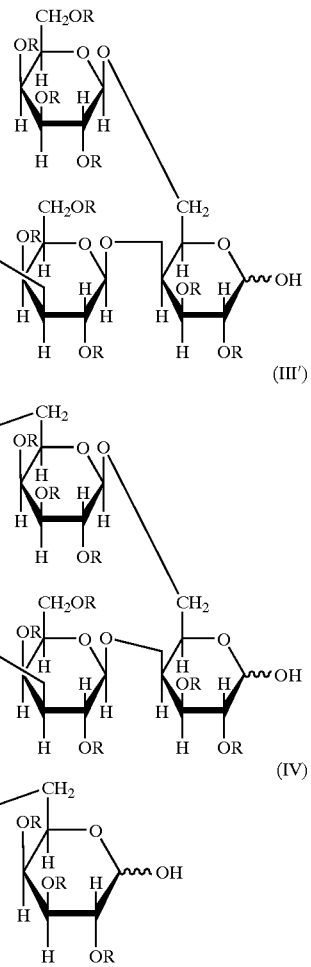

wherein R is H or SO$_3$H, or a salt thereof.

The third aspect of the present invention relates to a sulfated fucogalactan-digesting enzyme having the following chemical and physical properties. The enzyme can act on a sulfated fucogalactan containing galactose and fucose as constituting saccharides at a molar ratio of 1:1 to 6:1 or a salt thereof to convert the sulfated fucogalactan into smaller molecules and generate an oligosaccharide having sulfated galactose or galactose at its reducing end, has an optimal pH of about 7 to 9, and has an optimal temperature of about 25 to 45° C.

The fourth aspect of the present invention relates to a method for producing a smaller molecule from a sulfated fucogalactan or a salt thereof, characterized in that the method comprises allowing the sulfated fucogalactan-digesting enzyme according to the third aspect to act on a sulfated fucogalactan derived from brown algae or a salt thereof and obtaining a smaller molecule. Examples of the smaller molecules obtained using the enzyme include the oligosaccharide or a salt thereof according to the second aspect.

The fifth aspect of the present invention relates to a method for producing the sulfated fucogalactan-digesting enzyme according to the third aspect, characterized in that the method comprises culturing a bacterium of genus Flavobacterium capable of producing the sulfated fucogalactan-digesting enzyme and collecting the enzyme from the culture.

DETAILED DESCRIPTION OF THE INVENTION

Figure 1:
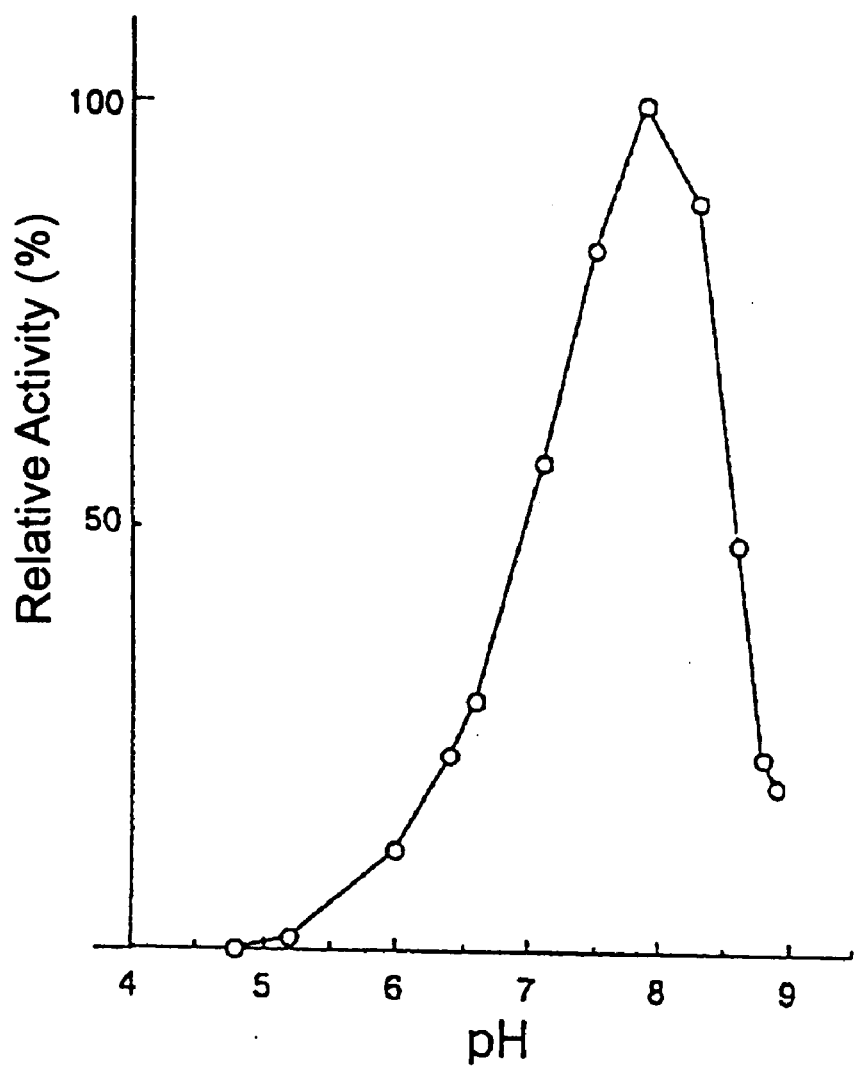
FIG. 1: a graph which illustrates the relationship between pH and the relative activity (%) of the sulfated fucogalactan-digesting enzyme according to the present invention.

The present invention will be explained in detail.

Seaweed belonging to brown algae contain plural kinds of sulfated-fucose-containing polysaccharides. Several molecular types of such polysaccharides including sulfated fucans and sulfated fucoglucuronomannans have been reported.

The sulfated fucogalactan of the present invention mainly contains galactose and fucose as constituting saccharides at a molar ratio of 1:1 to 6:1 (hereinafter referred to as the sulfated fucogalactan of the present invention or G-fucoidan). Examples thereof include a sulfated fucogalactan containing galactose and fucose at a molar ratio of 2:1. The sulfated fucogalactan is a sulfated polysaccharide having mean molecular weight of about 130,000 (molecular weight distribution: about 100,000 to about 200,000) as determined using HPLC gel filtration, for example. The molecular weight, the saccharide composition and the sulfate group content of the sulfated fucogalactan vary depending on the harvest time of the raw material for the sulfated fucogalactan, the method used for drying the raw material and the method used for storing the raw material. In addition, they vary depending on the heating conditions, pH and the like used for extracting the sulfated fucogalactan. For example, the sulfated fucogalactan may be hydrolyzed with acid. Thus, the molecular weight, the molecular weight distribution, the saccharide composition or the sulfate group content of the sulfated fucogalactan as described herein are just examples and may be readily changed depending on the conditions used for extracting the sulfated fucogalactan. For example, when the sulfated fucogalactan of the present invention is prepared by using the sulfated-fucose-containing polysaccharide-U-digesting enzyme and the sulfated-fucose-containing polysaccharide-F-digesting enzyme as described herein, the sulfated fucogalactan of the present invention having the saccharide composition and the molecular weight as described above is obtained. Thus, a sulfated fucogalactan having any molecular weight, molecular weight distribution, saccharide composition or sulfate group content can be prepared using appropriately selected preparation conditions. For example, about five sulfate group residues are contained in six principal constituting saccharides of the sulfated fucogalactan of the present invention. Generally, sulfate groups attached to saccharides through ester bonds are chemically unstable and readily cleaved with acid, alkali or heat. The sulfate group content is reduced, for example, by heating under acidic or alkaline conditions. Accordingly, the sulfated fucogalactan of the present invention can be intentionally desulfated. The amount of sulfate groups to be cleaved can be controlled by selecting the type and/or the concentration of the acid or alkali as well as the temperature and/or the time of heating upon the desulfation. Thus, the sulfated fucogalactans of the present invention include all of those derived from brown algae which are the sulfated fucogalactans having the characteristics as described above and the sulfated fucogalactans that are converted into smaller molecules by the sulfated fucogalactan-digesting enzyme of the present invention.

The main backbone of the sulfated fucogalactan of the present invention is represented by general formula (XII) below. The sulfated fucogalactans of the present invention include those of the general formula wherein n is an integer of 1 or more, for example 1 to 1000, preferably 1 to 500. The sulfated fucogalactans of the present invention include those having a structure in which general formula (XII) is continuously repeated and those having a structure in which general formula (XII) is discontinuously included being intervened by other structures as long as they are within the definition as described above.

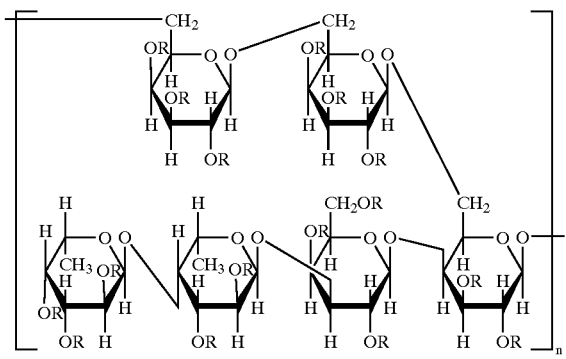

(XII)

wherein R is H or $SO_3H$.

For example, the brown algae from which the sulfated fucogalactans of the present invention can be prepared include, but are not limited to, Kjellmaniella crassifolia, Undaria pinnatifida, Laminaria japonica, Eisenia bicyclis, Ecklonia cava, Ecklonia kurome, Lessonia nigrescence, giant kelp and durvillaea. Without limitation, fucoidans derived from, for example, Kjellmaniella crassifolia contains U-fucoidan and F-fucoidan as well as G-fucoidan of the present invention.

Pharmaceutically acceptable salts can be used as the salts of the sulfated fucogalactan of the present invention. Examples of the salts include salts with alkaline metals such as sodium and potassium, alkaline earth metals such as calcium and magnesium and transition metals such as zinc as well as ammonium salts.

As used herein, a smaller molecule from a sulfated fucogalactan refers to an oligosaccharide having sulfated galactose or galactose at its reducing end, which is obtained by allowing the sulfated fucogalactan-digesting enzyme of the present invention to act on the sulfated fucogalactan of the present invention.

The sulfated fucogalactan-digesting enzyme of the present invention acts on the sulfated fucogalactan of the present invention to convert the sulfated fucogalactan into smaller molecules and generate an oligosaccharide having sulfated galactose or galactose at its reducing end. The endo-type fucose sulfate-containing polysaccharide-digesting enzyme as described in WO 97/26896, which digests a sulfated-fucose-containing polysaccharide-F, does not digest the sulfated fucogalactan of the present invention. In addition, the sulfated fucogalactan-digesting enzyme of the present invention is an enzyme that digests β 1–6 bonds and β 1–4 bonds between sulfated D-galactose or galactose and sulfated D-galactose or galactose in the sulfated fucogalactan of the present invention endowisely.

It is convenient to produce the sulfated fucogalactan of the present invention as a substrate for the sulfated fucogalactan-digesting enzyme of the present invention by first obtaining a fraction containing sulfated-fucose-containing polysaccharides from brown algae and then purifying the sulfated fucogalactan of the present invention therefrom. For example, an extract of water-soluble fraction is first obtained from brown algae in order to produce the fraction containing the sulfated-fucose-containing polysaccharides. In this case, it is preferable to carry out the extraction at pH 4–9 at a temperature of 100° C. or below in order to prevent the conversion of the sulfated-fucose-containing polysaccharides into smaller molecules.

The methods used for the removal of alginic acid from the extract include a method that utilizes isoelectric precipitation of alginic acid by treatment under acidic conditions, a method in which a salt (e.g., calcium salt) that forms precipitation with alginic acid is added, a method in which alginic acid is digested with an alginic acid-degrading enzyme and the like. Furthermore, small molecules such as amino acids and mannitol can be efficiently removed using ultrafiltration. Active carbon treatment is effective for the removal of hydrophobic substances.

A mixture of sulfated-fucose-containing polysaccharides can be obtained as described above. The sulfated fucogalactan of the present invention may be prepared from the mixture by allowing the sulfated-fucose-containing polysaccharide-F-digesting enzyme as described in WO 97/26896 as an endo-type fucose sulfate-containing polysaccharide-digesting enzyme and the sulfated-fucose-containing polysaccharide-U-digesting enzyme as described in WO 97/26896 as an endo-type fucoidan-digesting enzyme to act on the mixture of sulfated-fucose-containing polysaccharides, and then removing fractions of smaller molecules using ultrafiltration.

The thus obtained sulfated fucogalactan preparation may contain several kinds of sulfated-fucose-containing polysaccharides in addition to the sulfated fucogalactan. In this case, the sulfated fucogalactan of the present invention can be isolated, for example, by separation and purification using anion-exchange resin. Use of such procedure makes the amount of resin to be used less than the amount used for a procedure in which a mixture of sulfated-fucose-containing polysaccharides is directly subjected to separation with anion-exchange resin. Furthermore, the separation is remarkably improved because of the absence of the contaminating above-mentioned two types of sulfated-fucose-containing polysaccharides.

The sulfated fucogalactan of the present invention obtained as described above can be used as a substrate for determining an activity when the sulfated fucogalactan-digesting enzyme of the present invention is purified. Alternatively, it can be used as a raw material for producing the sulfated fucogalactan oligosaccharides of the present invention. The above-mentioned mixture of sulfated-fucose-containing polysaccharides may be used as a raw material for producing the sulfated fucogalactan oligosaccharides.

Any bacterial strains can be used for producing the enzyme of the present invention as long as they produce an enzyme that converts the sulfated fucogalactan of the present invention into smaller molecules. For example, Flavobacterium sp. SA-0082 as described in WO 97/26896 can be preferably used. This strain was deposited at the National Institute of Bioscience and Human-Technology, Agency of Industrial Science and Technology, Ministry of International Trade and Industry, 1–3, Higashi 1-chome, Tsukuba-shi, Ibaraki 305-8566, Japan on Mar. 29, 1995 under accession number FERM P-14872, and deposited at the National Institute of Bioscience and Human-Technology, Agency of Industrial Science and Technology, Ministry of International Trade and Industry under accession number FERM BP-5402 (date of request for transmission to international depositary authority: Feb. 15, 1996). This strain was determined to belong to genus Flavobacterium on the basis of bacteriological properties including Gram staining, GC content of the DNA and the principal quinone. On the other hand, the present inventors conducted homology search for the base sequence of the 16S rDNA of the present bacterium using Advanced BLAST search of National Center for Biotechnology Information (NCBI) which is available on the Internet since base sequences of 16S rDNAs are often taken into consideration in classification criteria recently.

Search for a bacterium of which the sequence of the gene is highly homologous to the above-mentioned base sequence revealed that the gene of Polaribacter filamentus has the highest homology in the entire region (89% homology in a region of 1424 bases). No other bacterium having a highly homologous sequence in the entire region was found. The sequences from Polaribacter irgensii (89% homology in a region of 1360 bases), Cytophaga sp. (92% homology in a region of 1249 bases) and Flexibacter maritimus (91% homology in a region of 1247 bases) exhibited relatively high homology. Generally, bacteria can not be identified to be of the same genus if the homology between the base sequences of 16S rDNAs is 90% or less. Therefore, the present bacterium was judged not to belong to a genus for known bacteria if such genetic classification is used. Thus, it is considered that the present bacterium is a novel bacterium belonging to order Cytophagales because most of the bacteriological properties of the present bacterium match with those of bacteria of genus Flavobacterium belonging to order Cytophagales and because all of the four bacteria of which the base sequences of the 16S rDNAs are highly homologous to the base sequence of the 16S rDNA of the present bacterium belong to order Cytophagales. As used herein, the bacteria of genus Flavobacterium include bacteria bacteriologically classified into genus Flavobacterium as well as bacteria genetically classified into order Cytophagales based on the sequence homology. Thus, the methods for producing the sulfated fucogalactan-digesting enzyme of the present invention include a method in which a bacterium belonging to order Cytophagales is cultured to produce the sulfated fucogalactan-digesting enzyme of the present invention.

Any media can be used for a bacterial strain in the method for producing the sulfated fucogalactan-digesting enzyme of the present invention as long as they are metabolized by the bacterial strain used to produce the sulfated fucogalactan-digesting enzyme of the present invention. For example, a sulfated fucogalactan, a mixture of sulfated-fucose-containing polysaccharides, seaweed powder, alginic acid, fucose, galactose, glucose, mannitol, glycerol, saccharose, maltose and the like can be utilized as carbon source. Peptone, yeast extract, meat extract and the like can be preferably used as nitrogen source. Furthermore, the present bacterium grows very well in seawater or artificial seawater that contains the nutrients as described above.

The yield varies depending on the conditions used to culture the producer strain of the sulfated fucogalactan-digesting enzyme of the present invention. Preferable culture conditions are a culture temperature of 15 to 30° C. and pH of the medium of 6 to 9. The maximal yield of the sulfated fucogalactan-digesting enzyme of the present invention is achieved after culturing with aeration and stirring for 5 to 72 hours. Naturally, the culture conditions are determined such that the yield of the sulfated fucogalactan-digesting enzyme of the present invention becomes maximal depending on the bacterial strain used, the composition of the medium and the like. The sulfated fucogalactan-digesting enzyme is present in both of the cells and the culture supernatant.

A cell-free extract is obtained by culturing Flavobacterium sp. SA-0082 in an appropriate medium, collecting the cells, and disrupting the cells by conventional means for cell disruption such as sonication. A purified enzyme preparation can be then obtained from the extract by conventional purification means. The sulfated fucogalactan-digesting enzyme of the present invention in a purified form substantially free of other sulfated-fucose-containing polysaccharide-digesting enzymes can be obtained by purification using, for example, salting out, ion-exchange column chromatography, hydrophobic bond column chromatography, gel filtration or the like. Furthermore, the purification procedure similar to that for the purification of the intracellular enzyme can be used to purify the enzyme of the present invention from the culture supernatant which also contains the enzyme in large quantities and is obtained by removing cells from the culture.

Figure 2:
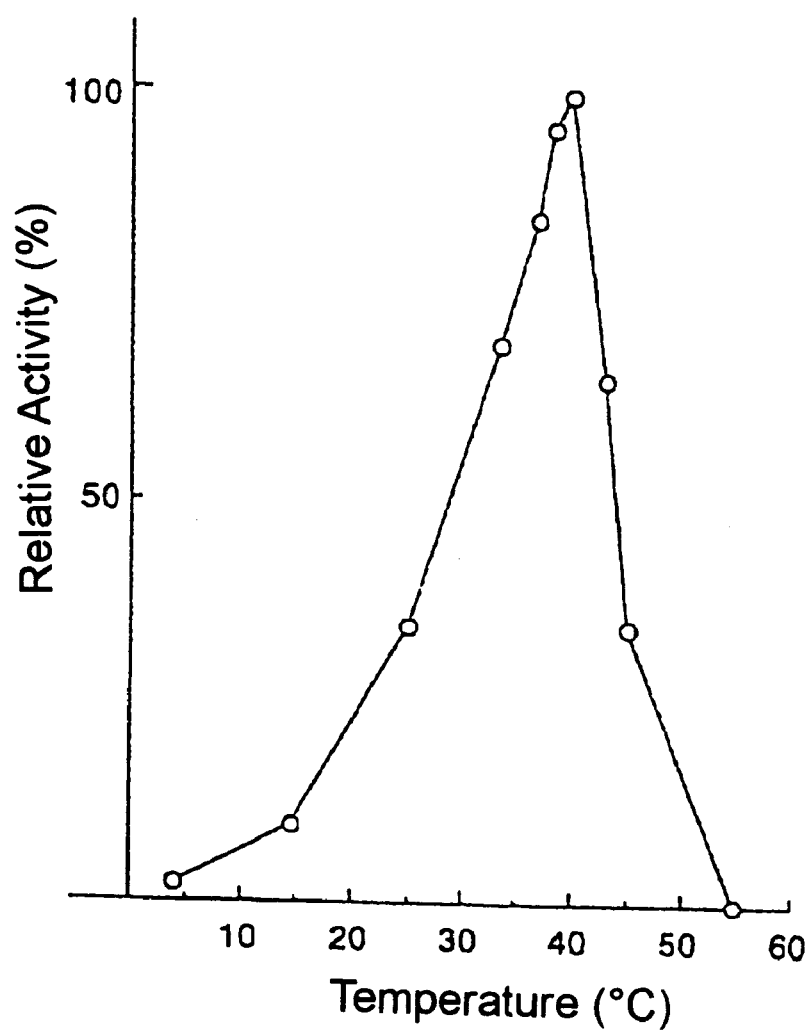
FIG. 2: a graph which illustrates the relationship between temperature and the relative activity (%) of the sulfated fucogalactan-digesting enzyme according to the present invention.

The chemical and physical properties of the sulfated fucogalactan-digesting enzyme of the present invention are as follows:

(I) acting on a sulfated fucogalactan containing galactose and fucose as constituting saccharides at a molar ratio of 1:1 to 6:1 or a salt thereof to convert the sulfated fucogalactan into smaller molecules and generate an oligosaccharide having sulfated galactose or galactose at its reducing end;

(II) having an optimal pH of about 7 to 9 (FIG. 1, a graph which illustrates the relationship between the reaction pH and the relative activity of the enzyme of the present invention, in which the vertical axis represents the relative activity (%) and the horizontal axis represents the pH); and (III) having an optimal temperature of about 25 to 45° C. (FIG. 2, a graph which illustrates the relationship between the reaction temperature and the relative activity of the enzyme of the present invention, in which the vertical axis represents the relative activity (%) and the horizontal axis represents the temperature (°C.)).

The activity of the sulfated fucogalactan-digesting enzyme of the present invention can be determined, for example, by analyzing digestion product, which is obtained by allowing the enzyme to act on the sulfated fucogalactan, using HPLC and determining the degree of conversion into smaller molecules. Alternatively, the activity can be determined by measuring the generation of reducing ends according to a conventional method. The activity can be determined using either a cell extract from the producer strain or an enzyme solution obtained after purification on chromatography.

The smaller molecule from the sulfated fucogalactan of the present invention or a salt thereof can be prepared by allowing the sulfated fucogalactan-digesting enzyme of the present invention to act on the sulfated fucogalactan of the present invention or a material containing the sulfated fucogalactan. For example, a partially purified product from the sulfated fucogalactan of the present invention, a fraction of sulfated-fucose-containing polysaccharides derived from brown algae, a product obtained by extracting brown algae with an aqueous solvent, or brown algae itself can be preferably used as the material containing the sulfated fucogalactan of the present invention.

The sulfated fucogalactan of the present invention or the material containing the sulfated fucogalactan may be dissolved according to a conventional method. The sulfated fucogalactan of the present invention or the material containing the sulfated fucogalactan may be dissolved in the solution at the maximal concentration. However, the concentration is usually selected taking its operationality and the titer of the enzyme into consideration. The solvent for the sulfated fucogalactan of the present invention may be selected from water, buffers and the like depending on the objects. Usually, the pH of the solution is nearly neutral. The enzymatic reaction is usually carried out at about 30° C. The molecular weight of the smaller molecules can be controlled by adjusting the amount of the enzyme, the reaction time and the like. Smaller molecules from the sulfated fucogalactan of the present invention having more homogeneous molecular weight distribution can be prepared by subjecting the smaller molecules to molecular weight fractionation. Conventional means for molecular weight fractionation such as gel filtration and molecular weight fractionation membrane can be applied. Optionally, the smaller molecules may be further purified using ion-exchange resin treatment, active carbon treatment or the like, or they may be desalted, sterilized or lyophilized.

Without limitation, the smaller molecules from the sulfated fucogalactan of the present invention include, for example, disaccharide to hexasaccharides obtained by allowing the sulfated fucogalactan-digesting enzyme of the present invention to act on the sulfated fucogalactan of the present invention. The positions of substitution with sulfate groups in the smaller molecules of the present invention vary depending on the preparation method. All of the smaller molecules obtained by the action of the sulfated fucogalactan-digesting enzyme of the present invention are included in the smaller molecules of the present invention. For example, the chemical structures of the smaller molecules are represented by general formulas (I) to (IV) below. Among these, general formula (III) is supposed to be the constituting unit of the sulfated fucogalactan.

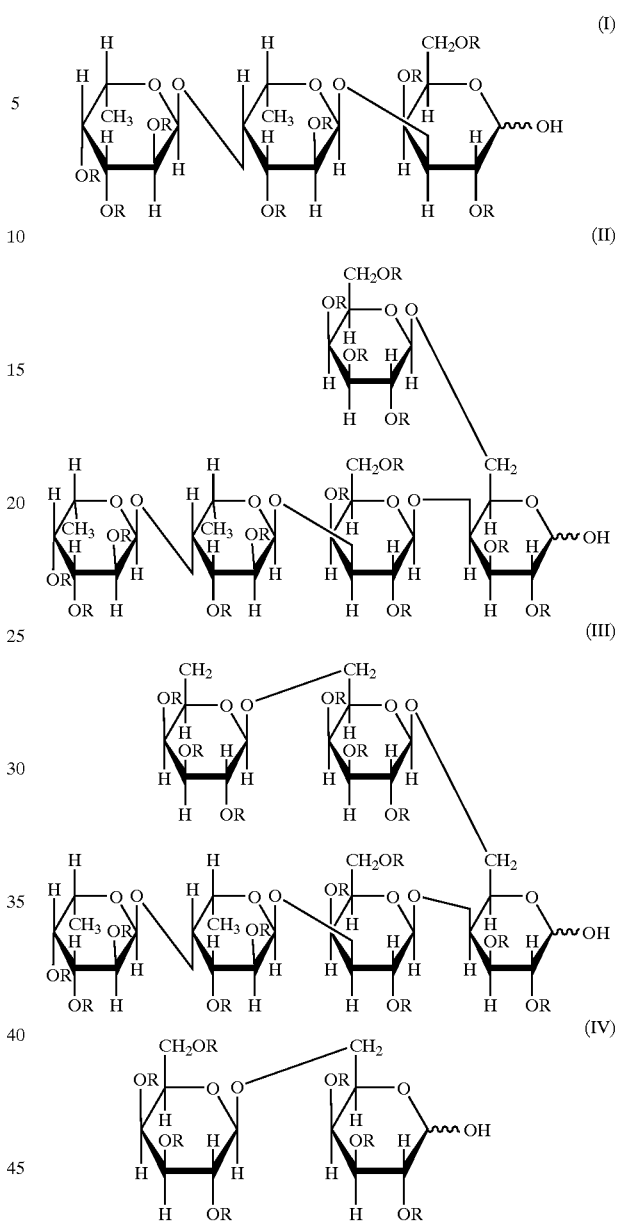

wherein R is H or $SO_3H$.

The smaller molecules of the present invention have sulfate groups within the molecules, which groups react with various bases to form salts. The smaller molecule from the sulfated fucogalactan of the present invention is stable when it is in a form of salt. It is usually provided in a form of sodium and/or potassium and/or calcium salt. The smaller molecule from the sulfated fucogalactan of the present invention in a free form can be derived from a salt thereof by utilizing cation-exchange resin such as Dowex 50W (Dow Chemical). Optionally, it can be further subjected to conventional salt-exchange to convert it into any one of various salts of interest.

Pharmaceutically acceptable salts can be used as the salts of the smaller molecules from the sulfated fucogalactan of the present invention. Examples of the salts include salts with alkaline metals such as sodium and potassium, alkaline earth metals such as calcium and magnesium and transition metals such as zinc as well as ammonium salts.

Only the sulfated fucogalactan of the present invention contained in any fractions containing sulfated-fucose-containing polysaccharides can be converted into smaller molecules by using the sulfated fucogalactan-digesting enzyme of the present invention. Thus, the sulfated fucogalactan of the present invention can be selectively removed by using the enzyme in combination with molecular weight fractionation. For example, it has been reported that fractions containing sulfated fucans have various biological activities such as an anticoagulant activity, an activity of suppressing cancer metastasis and an activity of suppressing viral infection. Fractions containing sulfated fucans obtained from brown algae according to conventional methods contain sulfated fucans and other polysaccharides. The sulfated fucogalactan can be removed from the fractions containing sulfated fucans by utilizing the sulfated fucogalactan-digesting enzyme of the present invention. As a result, highly pure sulfated fucans can be obtained.

Furthermore, it has been reported that, for example, sulfated fucoglucuronomannans have an apoptosis-inducing activity against tumor cells. The sulfated fucogalactan of the present invention contaminating in sulfated fucoglucuronomannans obtained from brown algae can be readily removed by utilizing the sulfated fucogalactan-digesting enzyme of the present invention. As a result, highly pure sulfated fucoglucuronomannans can be conveniently obtained.

For example, a solution of a material containing the sulfated fucogalactan of the present invention in an aqueous solvent is prepared in order to remove the sulfated fucogalactan of the present invention. The material containing the sulfated fucogalactan of the present invention may be dissolved according to a conventional method. The material containing the sulfated fucogalactan of the present invention may be dissolved in the solution at the maximal concentration. However, the concentration is usually selected taking its operationality and the titer of the enzyme into consideration. The solvent for the sulfated fucogalactan of the present invention may be selected from water, buffers and the like depending on the objects. Usually, the preferable pH of the solution is nearly neutral. The sulfated fucogalactan-digesting enzyme of the present invention or a substance onto which the enzyme has been immobilized, or both, is then added to and reacted with the solution of the material containing the sulfated fucogalactan of the present invention to convert the sulfated fucogalactan of the present invention into smaller molecules. The enzymatic reaction is usually carried out at about 30° C. The amount of the enzyme, the reaction time and the like may be suitably adjusted depending on the ability of molecular weight fractionation in the subsequent step. A product of interest from which the smaller molecules from the sulfated fucogalactan of the present invention have been readily removed can be prepared by subjecting the resulting mixture to molecular weight fractionation. Conventional means for molecular weight fractionation such as gel filtration and ultrafiltration utilizing molecular weight fractionation membrane can be applied.

The sulfated fucogalactan-digesting enzyme of the present invention acts on the sulfated fucogalactan of the present invention. Thus, it can be used for the structural analysis of the sulfated fucogalactan of the present invention. For example, the smaller molecules having chemical structure of general formulas (I) to (IV) above are obtained by allowing the sulfated fucogalactan-digesting enzyme of the present invention to act on the sulfated fucogalactan of the present invention.

The sulfated fucogalactan component of the present invention can be selectively removed from sulfated-fucose-containing polysaccharides that contain the sulfated fucogalactan of the present invention by using the sulfated fucogalactan-digesting enzyme of the present invention. For example, highly pure sulfated fucans or sulfated fucoglucuronomannans from which the sulfated fucogalactan component of the present invention has been removed can be preferably used as raw materials for pharmaceuticals.

The sulfated fucogalactan-digesting enzyme of the present invention can be used in combination with the sulfated-fucose-containing polysaccharide-F-digesting enzyme as described in WO 97/26896 and/or the sulfated-fucose-containing polysaccharide-U-digesting enzyme as described in WO 97/26896. Without limitation, when a mixture of sulfated-fucose-containing polysaccharides obtained, for example, by extraction of Kjellmaniella crassifolia at pH 4 to 9 at 100° C. or below is treated with the above-mentioned sulfated-fucose-containing polysaccharide-U-digesting enzyme and the sulfated fucogalactan-digesting enzyme of the present invention, sulfated polysaccharides which contain sulfated saccharides of general formula (XIV) below as the essential components of constituting saccharides in a repetitive manner can be obtained. Sulfated saccharides of the following general formula wherein n is a integer of 1 or more, for example 1 to 10,000, preferably 1 to 5,000 are obtained.

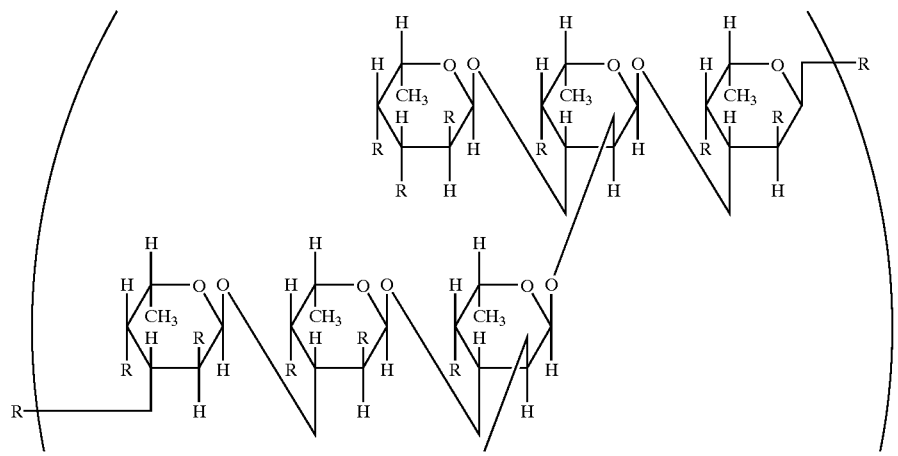

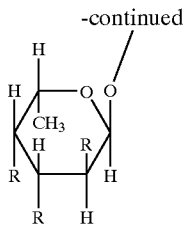

wherein R is H or OSO₃H.

The above-mentioned sulfated polysaccharide contains fucose as a constituting saccharide. For example, extraction at pH 6 to 8 at 95° C. for 2 hours results in mean molecular weight of about 200,000 (molecular weight distribution: about 10,000 to about 1,000,000). Furthermore, for example, extraction at pH 6 to 8 at 25° C. for 24 hours results in mean molecular weight of about 13,000,000 (molecular weight distribution: about 100,000 to about 20,000,000). The mean molecular weight and the molecular weight distribution vary depending on the extraction conditions as described above. However, the resulting sulfated polysaccharides are converted into smaller molecules by the sulfated-fucose-containing polysaccharide-F-digesting enzyme regardless of the extraction conditions used. The molecular weight and the sulfate group content of the sulfated polysaccharide vary depending on the harvest time of the raw material for the sulfated polysaccharides, the method used for drying the raw material and the method used for storing the raw material. In addition, they vary depending on the heating conditions, pH and the like used for the extraction. For example, the sulfated polysaccharide may be hydrolyzed with acid. Therefore, the molecular weight, the molecular weight distribution or the sulfate group content of the sulfated polysaccharide as described herein are just examples and may be readily changed depending on the conditions used for extracting the sulfated polysaccharide. Thus, a sulfated polysaccharide having any molecular weight, molecular weight distribution or sulfate group content can be prepared using appropriately selected preparation conditions. For example, about twelve sulfate groups are contained in seven principal constituting saccharides of the sulfated polysaccharide. Generally, sulfate groups attached to saccharides through ester bonds are chemically unstable and readily cleaved with acid, alkali or heat. The sulfate group content is reduced, for example, by heating under acidic or alkaline conditions. Accordingly, the sulfated polysaccharides can be intentionally desulfated. The amount of sulfate groups to be cleaved can be controlled by selecting the type and/or the concentration of the acid or alkali as well as the temperature and/or the time of heating upon the desulfation.

Furthermore, novel sulfated saccharides can be obtained by using the sulfated fucogalactan-digesting enzyme, the sulfated-fucose-containing-polysaccharide-F-digesting enzyme and the sulfated-fucose-containing polysaccharide-U-digesting enzyme in combination. In addition, sulfated saccharides can be classified in a manner different from the conventional one by the use of the combination of the above-mentioned three digesting enzymes. Without limitation, for example, the following fractions can be obtained when the enzymes are allowed to act on a mixture of sulfated-fucose-containing polysaccharides derived from brown algae such as Kjellmaniella crassifolia:

(1) a fraction of sulfated saccharides which are not digested with the sulfated-fucose-containing-polysaccharide-F-digesting enzyme or the sulfated-fucose-containing polysaccharide-U-digesting enzyme but are digested with the sulfated fucogalactan-digesting enzyme (the sulfated fucogalactan of the present invention);

(2) a fraction of sulfated saccharides which are not digested with the sulfated fucogalactan-digesting enzyme or the sulfated-fucose-containing-polysaccharide-F-digesting enzyme but are digested with the sulfated-fucose-containing polysaccharide-U-digesting enzyme;

(3) a fraction of sulfated saccharides which are not digested with the sulfated fucogalactan-digesting enzyme or the sulfated-fucose-containing polysaccharide-U-digesting enzyme but are digested with the sulfated-fucose-containing-polysaccharide-F-digesting enzyme; and (4) a fraction of sulfated saccharides which are not digested with the sulfated fucogalactan-digesting enzyme, the sulfated-fucose-containing-polysaccharide-F-digesting enzyme or the sulfated-fucose-containing polysaccharide-U-digesting enzyme. These fractions of sulfated saccharides could not be obtained without the use of the sulfated fucogalactan-digesting enzyme of the present invention in combination with the sulfated-fucose-containing-polysaccharide-F-digesting enzyme or the sulfated-fucose-containing polysaccharide-U-digesting enzyme.

The sulfated fucogalactan of the present invention or a salt thereof has an activity of inducing growth factor production, in particular, an activity of inducing hepatocyte growth factor (HGF) production.

Liver rapidly regenerates to the original size after it is subjected to partial hepatectomy. The essential factor involved in the liver regeneration was unknown for a long time. Then, HGF was found in plasma from patients with fulminant hepatitis and isolated and purified therefrom (J. Clin. Invest., 88:414–419, 1988). Furthermore, the cDNA for human HGF was cloned, and the primary structure of HGF was revealed (Biochem. Biophys. Res. Commun., 163:967–973, 1989). Furthermore, it was demonstrated that scatter factor (SF), which activates the motility of cells, and tumor cytotoxic factor (TCF) are the same substance with HGF (Proc. Natl. Acad. Sci. USA 88:7001–7005, 1991; Biochem. Biophys. Res. Commun., 180:1151–1158, 1991).

HGF promotes the growth of many types of epithelial cells including bile duct epithelial cells, renal tubule epithelial cells and tunica mucosa ventriculi cells in addition to hepatocytes. Furthermore, HGF is a multifunctional active substance which exhibits a wide variety of physiological activities including activation of motility of epithelial cells as well as induction of morphogenesis such as vascularization and lumen formation of epithelial cells. In other words, HGF is involved in growth promotion and motility activation of epithelial cell for repair of damaged organ, induction of morphogenesis such as vascularization and the like in various organs. HGF also exhibits an activity of proliferating hepatocyte, an activity of promoting protein synthesis, an activity of improving cholestasia, an activity of preventing renal damage due to drug and the like. Based on these facts, HGF is expected to serve as therapeutic agents for severe hepatitis, cirrhosis and cholestasia in liver.

mRNA for HGF is synthesized in brain, kidney, lung and the like. HGF exhibits growth activities on hepatocytes, renal tubule cells, epidermal cells and the like. Thus, HGF is a mesodermic cell growth factor. Therefore, the sulfated fucogalactan of the present invention or a salt thereof, which induces the production of hepatocyte growth factor, is useful as an ingredient for a composition for treating or preventing hepatitis, severe hepatitis, cirrhosis, cholestasia in liver, chronic nephritis, pneumonia and wound.

The sulfated fucogalactan of the present invention or a salt thereof can be used as an active ingredient for a cosmetic composition based on its activity of inducing HGF production. For example, it is useful as a cosmetic composition for inducing HGF production. Thus, a biological cosmetic composition having an activity of inducing HGF production can be provided.

A cosmetic composition for inducing growth factor production (e.g., a cosmetic composition for inducing HGF production) containing the sulfated fucogalactan of the present invention or a salt thereof can be formulated according to conventional methods into, for example, lotion, milky lotion, cream, pack, bath agent, facial cleansing agent, bath cleansing agent, hair agent, hair tonic and shampoo.

The sulfated fucogalactan of the present invention, the smaller molecule from the sulfated fucogalactan or a salt thereof can be used as an antigen. Antibodies are produced according to conventional methods. For example, a polyclonal antibody can be prepared by immunizing an animal such as a rabbit with the sulfated fucogalactan of the present invention, the smaller molecule from the sulfated fucogalactan or a salt thereof along with an adjuvant. Furthermore, a monoclonal antibody can be prepared by fusing melanoma cells with antibody-producing B cells obtained by immunization with an antigen, selecting hybridomas producing the antibody of interest and culturing the cells. Such antibodies can be used for purifying the sulfated fucogalactan of the present invention, the smaller molecule from the sulfated fucogalactan or a salt thereof. Also, the antibodies can be used to identify the sulfated fucogalactan of the present invention in seaweed. For example, the content of the sulfated fucogalactan of the present invention in a seaweed extract can be readily determined using an antibody that recognizes the sulfated fucogalactan of the present invention. Thus, an extract with high content can be efficiently prepared. Furthermore, antibodies that recognize the sulfated fucogalactan of the present invention, the smaller molecule from the sulfated fucogalactan or a salt thereof are useful for the analysis of the mode of action of inhibiting fertilization, the mode of action of inhibiting viral infection, in vivo metabolism or the like of the sulfated fucogalactan of the present invention, the smaller molecule from the sulfated fucogalactan or a salt thereof.

Additionally, the smaller molecule, or the oligosaccharide, obtained by allowing the sulfated fucogalactan-digesting enzyme of the present invention to act on the sulfated fucogalactan of the present invention or a salt thereof can be used as a reagent for glycotechnology. A substance which is very useful as a reagent for glycotechnology can be provided, for example, by subjecting the smaller molecule to pyridyl-(2)-amination as described in JP-B 5-65108 to prepare a pyridyl-(2)-aminated product of the smaller molecule.

EXAMPLES

The following examples further illustrate the present invention in detail but are not to be construed to limit the scope thereof.

Example 1

Preparation of Sulfated Fucogalactan (1) Sulfated fucogalactan was prepared as follows.

2 Kg of dried Kjellmaniella crassifolia was disrupted using a cutter mill (Masuko Sangyo) equipped with a screen having a pore diameter of 1 mm, stirred in 20 L of 80% ethanol at 25° C. for 3 hours, filtered and washed. The resulting residue was suspended in 20 L of 30 mM imidazole buffer (pH 8.2) containing 50 mM calcium chloride, 100 mM sodium chloride, 10% ethanol and 1 U of the sulfated-fucose-containing polysaccharide-F-digesting enzyme. The sulfated-fucose-containing polysaccharide-F-digesting enzyme was obtained from a culture of Alteromonas sp. SN-1009 (deposited at the National Institute of Bioscience and Human-Technology, Agency of Industrial Science and Technology, Ministry of International Trade and Industry, 1–3, Higashi 1-chome, Tsukuba-shi, Ibaraki-ken 305–8566, Japan on Feb. 13, 1996 under accession number FERM P-15436, and deposited at the National Institute of Bioscience and Human-Technology, Agency of Industrial Science and Technology, Ministry of International Trade and Industry under accession number FERM BP-5747 (date of request for transmission to international depositary authority: Nov. 15, 1996)) as described in WO97/26896. The high viscosity and elasticity due to sulfated-fucose-containing polysaccharides having high molecular weight were completely lost after the suspension was stirred at 25° C. for 2 days. The suspension was filtered through a stainless steel screen having a pore diameter of 32 μm to remove smaller molecules from the sulfated-fucose-containing polysaccharides, and then washed. The resulting residue was suspended in 40 L of sodium phosphate buffer (pH 6.6) containing 100 mM sodium chloride, 10% ethanol and 4 g of alginate lyase K (Nagase Biochemicals). The suspension was stirred at 25° C. for 4 days, and then centrifuged to obtain a supernatant. The supernatant was concentrated to 2 L using an ultrafiltration device equipped with hollow fibers with exclusion molecular weight of 100,000 to remove smaller molecules from alginic acid contained in the supernatant. The solvent of the concentrate was exchanged for 100 mM sodium chloride containing 10% ethanol. An equal volume of 400 mM calcium acetate was added to the solution. After stirring, the mixture was centrifuged. 1 N hydrochloric acid was added to the resulting supernatant to adjust the pH to 2 while cooling on ice. The formed precipitate was removed by centrifugation. 1 N sodium hydroxide was added to the resulting supernatant to adjust the pH to 8.0. The solution was concentrated to 1 L by ultrafiltration and the solvent was exchanged for 100 mM sodium chloride. The formed precipitate was removed by centrifugation. The following procedure was carried out in order to remove hydrophobic substances in the resulting supernatant. Sodium chloride was added to the supernatant at a concentration of 1 M. The mixture was loaded onto a 3-L Phenyl-Cellulofine column (Seikagaku Corporation) equilibrated with 1 M sodium chloride and flow-through fractions were collected. The fractions were concentrated using an ultrafiltration device, subjected to solvent exchange for 20 mM sodium chloride and lyophilized. The weight of the lyophilization product was 29.3 g.

(2) 15 g of the lyophilization product was dissolved in 1.5 L of 50 mM tris-hydrochloride buffer containing 400 mM sodium chloride and 9 U of the sulfated-fucose-containing polysaccharide-U-digesting enzyme. The sulfated-fucose-containing polysaccharide-U-digesting enzyme was obtained from a culture of Flavobacterium sp. SA-0082 (deposited at the National Institute of Bioscience and Human-Technology, Agency of Industrial Science and Technology, Ministry of International Trade and Industry, 1–3, Higashi 1-chome, Tsukuba-shi, Ibaraki-ken 305–8566, Japan on Mar. 29, 1995 under accession number FERM P-14872, and deposited at the National Institute of Bioscience and Human-Technology, Agency of Industrial Science and Technology, Ministry of International Trade and Industry under accession number FERM BP-5402 (date of request for transmission to international depositary authority: Feb. 15, 1996)) as described in WO97/26896. The solution was reacted at 25° C. for 6 days and then concentrated to about 300 ml using an evaporator. The concentrate was placed in a dialysis tube with exclusion molecular weight of 3500 and extensively dialyzed to remove smaller molecules from the sulfated fucoglucuronomannans. The solution retained in the dialysis tube was loaded onto a 4-L DEAE-Cellulofine A-800 (Chisso Corporation) equilibrated with 50 mM sodium chloride. After extensive washing with 50 mM sodium chloride, elution was carried out with a gradient of 50 to 650 mM sodium chloride. Extensive elution from the column was further carried out with 650 mM sodium chloride. The fraction eluted with 650 mM sodium chloride was collected as a sulfated fucogalactan fraction, concentrated using an ultrafiltration device with exclusion molecular weight of 100,000, subjected to solvent exchange for 10 mM sodium chloride and lyophilized to obtain 0.85 g of a lyophilization product of the sulfated fucogalactan fraction. The saccharide composition of the fraction was analyzed. The amount of fucose was determined as described in Journal of Biological Chemistry, 175:595 (1948).

The dried product of the sulfated fucogalactan was dissolved in 1 N hydrochloric acid at a concentration of 0.5%. The solution was treated at 110° C. for 2 hours to hydrolyze into constituting monosaccharides. Reducing ends of the monosaccharides resulted from the hydrolysis were subjected to pyridyl-(2)-amination using GlycoTAG (Takara Shuzo) and GlycoTAG Reagent Kit (Takara Shuzo) to determine the ratio of constituting saccharides using HPLC. The HPLC was carried out as follows.

Instrument: L-6200 (Hitachi);
Column: Palpak Type A (4.6 mm×150 mm; Takara Shuzo);
Eluent: 700 mM borate buffer (pH 9.0): acetonitrile=9:1;
Detection: excitation wavelength at 310 nm and emission wavelength at 380 nm using fluorescence detector F-1150 (Hitachi);
Flow rate: 0.3 ml/minute; and
Column temperature: 65° C.

The amount of uronic acid was determined as described in Analytical Biochemistry, 4:330 (1962). Furthermore, the content of sulfate was determined as described in Biochemical Journal, 84:106 (1962).

As a result, the sulfated fucogalactan contained galactose and fucose as constituting saccharides at a molar ratio of about 2:1. Substantially no uronic acid or other neutral sugar was contained therein. The molar ratio of fucose and sulfate group was about 1:2.

(3) Method for measuring activity of sulfated fucogalactan-digesting enzyme

The activity of the sulfated fucogalactan-digesting enzyme of the present invention was measured using the sulfated fucogalactan fraction obtained in (2) as follows.

Briefly, 60 μl of 50 mM imidazole-hydrochloride buffer (pH 7.5), 4.8 μl of 2.5% solution of the sulfated fucogalactan fraction, 6 μl of 4 M sodium chloride, 37.2 μl of water and 12 μl of the sulfated fucogalactan-digesting enzyme of the first aspect of the present invention were mixed together. After reacting at 37° C. for 3 hours, the reaction mixture was treated at 100° C. for 10 minutes. After centrifugation, 100 μl of the supernatant was analyzed using HPLC to determine the degree of conversion into smaller molecules. As a control, a reaction mixture obtained by a reaction under the similar conditions in which the buffer used for dissolving the sulfated fucogalactan-digesting enzyme of the first aspect of the present invention was used in place of the enzyme and a reaction mixture obtained by a reaction in which water was used in place of the sulfated fucogalactan fraction were prepared, and similarly analyzed using HPLC.

1 unit of the enzyme is defined as an amount of the enzyme that cleaves galactosyl bonds in 1 μmol of the sulfated fucogalactan fraction in 1 minute in the above-mentioned reaction system. The amount of cleaved galactosyl bond was calculated according to the following equation.

$\{(4.8 \times 1000 \times 2.5/100)MG\} \times \{(MG/M)-1\} \times \{1/(180 \times 0.012)\} = U/ml$  4.8×1000×2.5/100: sulfated fucogalactan added to the reaction system (μg);

MG: mean molecular weight of sulfated fucogalactan in the fraction as a substrate;

M: mean molecular weight of reaction product;

(MG/M)-1: number of bonds cleaved by the enzyme in one molecule of the sulfated fucogalactan;

180: reaction time (minutes); and 0.012: volume of enzyme solution (ml).

The HPLC was carried out as follows.

Instrument: L-6200 (Hitachi);
Column: OHpak SB-806HQ (8×300 mm; Showa Denko);
Eluent: 50 mM sodium chloride containing 5 mM sodium azide;
Detection: differential refractive index detector (Shodex RI-71, Showa Denko);
Flow rate: 1 ml/minute; and
Column temperature: 25° C.

The following procedure was carried out in order to determine the mean molecular weight of the reaction product. Commercially available pullulan (STANDARD P-82, Showa Denko) of which the molecular weight was known was analyzed under the same conditions as those for the above-mentioned HPLC analysis. The relationship between the molecular weight of pullulan and retention time was expressed as a curve, which was used as a standard curve for determining the molecular weight of the enzymatic reaction product.

The amount of protein was determined by measuring the absorbance of the enzyme solution at 280 nm. The calculation was carried out defining the absorbance of a solution containing a protein at a concentration of 1 mg/ml as 1.0.

Example 2

Determination of Mode of Action of Sulfated Fucogalactan-Digesting Enzyme (1) Preparation of sulfated fucogalactan-digesting enzyme For the production of the sulfated fucogalactan-digesting enzyme, Flavobacterium sp. SA-0082 (FERM BP-5402) was inoculated into 600 ml of a medium consisting of artificial seawater (Jamarine Laboratory) containing 0.1% glucose, 1.0% peptone and 0.05% yeast extract (pH 7.5) which had been sterilized at 120° C. for 20 minutes, and cultured at 24° C. for 23 hours to prepare a seed culture. 20 L of a medium consisting of artificial seawater containing 0.2% sulfated-fucose-containing polysaccharide fraction from Kjellmaniella crassifolia prepared as described in Example 3(1) below, 2.0% peptone, 0.01% yeast extract and 0.01% antifoaming agent (KM70, Shin-Etsu Chemical) (pH 7.5) was placed in 30 L jar fermentor and sterilized at 120° C. for 20 minutes. After cooling, 600 ml of the seed culture was inoculated into the medium and cultured at 24° C. for 23 hours with aeration at 10 L per minute and stirring at 125 rpm. After cultivation, the culture was centrifuged to collect cells.

The cells were suspended in 1,200 ml of 10 mM tris-hydrochloride buffer (pH 8.0) containing 0.4 M sodium chloride, sonicated and centrifuged to obtain a cell extract. The cell extract was extensively dialyzed against the same buffer and centrifuged to obtain a supernatant. Ammonium sulfate was added to the supernatant at a final concentration of 90% saturation. The formed precipitate collected by centrifugation was dissolved in 150 ml of 10 mM tris-hydrochloride buffer (pH 8.0) containing 50 mM sodium chloride and extensively dialyzed against the same buffer. A supernatant obtained by centrifugation was loaded onto a 500-mL DEAE-Sepharose FF column (Amersham Pharmacia) equilibrated with the same buffer. After washing with the same buffer, elution was then carried out with a gradient of 50 mM to 600 mM sodium chloride to collect an active fraction.

The active fraction was extensively dialyzed against 10 mM tris-hydrochloride buffer (pH 8.0) containing 0.1 M sodium chloride, loaded onto a 100-mL DEAE-Cellulofine A-800 column (Chisso Corporation) equilibrated with the same buffer. After washing with the same buffer, elution was carried out with a gradient of 0.1 M to 0.4 M sodium chloride to collect an active fraction. Sodium chloride was added to the active fraction at a concentration of 4 M. The fraction was loaded onto a 20-mL Phenyl-Cellulofine column (Chisso Corporation) equilibrated with 10 mM tris-hydrochloride buffer (pH 8.0) containing 4 M sodium chloride. After washing with the same buffer, elution was carried out with a gradient of 4 M to 1 M sodium chloride. Extensive elution was further carried out with 10 mM tris-hydrochloride buffer (pH 8.0) containing 1 M sodium chloride to collect an active fraction. Sodium chloride was added to the active fraction at a concentration of 3 M. The fraction was loaded onto a 10-mL Phenyl-Cellulofine column (Chisso Corporation) equilibrated with 10 mM tris-hydrochloride buffer (pH 8.0) containing 3 M sodium chloride. After washing with the same buffer, elution was carried out with a gradient of 3 M to 0.5 M sodium chloride. Extensive elution was further carried out with 10 mM tris-hydrochloride buffer (pH 8.0) containing 0.5 M sodium chloride to collect an active fraction. The thus obtained purified enzyme was used as a sulfated fucogalactan-digesting enzyme.

(2) Preparation of smaller molecules from sulfated fucogalactan

Smaller molecules were prepared by allowing the purified sulfated fucogalactan-digesting enzyme to act on the sulfated fucogalactan fraction as described in Example 1(2). Briefly, 1.94 g of the sulfated fucogalactan fraction was dissolved in 25 mM tris-hydrochloride buffer (pH 8.0) containing 0.2 M sodium chloride. 186 mU of the sulfated fucogalactan-digesting enzyme as described in Example 2(1) was added thereto. The mixture was reacted at 25° C. for 6 days. The reaction mixture was concentrated to 80 ml using an evaporator and subjected to molecular weight fractionation using Cellulofine GCL-1000 column (Chisso Corporation) (4×90 cm). A fraction corresponding to molecular weight of 15,000 or less was collected to obtain a fraction of enzymatic digest from sulfated fucogalactan.

A portion of the fraction of enzymatic digest from sulfated fucogalactan was subjected to pyridyl-(2)-amination of reducing ends using GlycoTAG (Takara Shuzo) and Glyco-TAG Reagent Kit (Takara Shuzo). The resulting pyridyl-(2)-aminated saccharides were hydrolyzed by treating them in 2 N hydrochloric acid at 100° C. for 3 hours. The saccharides at the reducing ends were examined using HPLC. The HPLC was carried out as follows.

Instrument: L-6200 (Hitachi);

Column: Palpak Type A (4.6×150 mm; Takara Shuzo);

Eluent: 0.7 M borate buffer (pH 9.0): acetonitrile=9:1;

Detection: excitation wavelength at 310 nm and emission wavelength at 380 nm using fluorescence detector (F-1150, Hitachi);

Flow rate: 0.3 ml/minute; and

Column temperature: 65° C.

As a result, only galactose was detected. Thus, it was demonstrated that all of the saccharides at the reducing ends in the fraction of enzymatic digest from sulfated fucogalactan were sulfated galactose or galactose.

Furthermore, a portion of the sample which had been subjected to the analysis of the saccharides at the reducing ends was subjected to pyridyl-(2)-amination again and analyzed using HPLC as described above in order to analyze the composition of neutral saccharides in the fraction of enzymatic digest from sulfated fucogalactan. As a result, it was demonstrated that the fraction of enzymatic digest from sulfated fucogalactan consisted of galactose and fucose with a molar ratio of about 2:1. The above-mentioned results demonstrated that the sulfated fucogalactan-digesting enzyme of the present invention was an endo-type galactosidase which cleaves galactosyl bonds in the sulfated fucogalactan to generate oligosaccharides having sulfated galactose or galactose at their reducing ends.

Example 3

(1) Sulfated fucose-containing polysaccharide fraction was prepared from Kjellmaniella crassifolia. Briefly, 2 Kg of commercially available dried Kjellmaniella crassifolia was disrupted using a cutter mill (Masuko Sangyo) equipped with a screen having a pore diameter of 1 mm and suspended in 20 L of 80% ethanol. The suspension was stirred at 25° C. for 3 hours and filtered through a filter paper. The resulting residue was suspended in 40 L of 30 mM sodium phosphate buffer (pH 6.5) containing 100 mM sodium chloride. The suspension was treated at 95° C. for 2 hours and filtered through a stainless steel screen having a pore diameter of 106 μm. 200 g of active carbon, 4.5 L of ethanol and 12,000 U of alginate lyase K (Nagase Biochemicals) were added to the filtrate. The mixture was stirred at 25° C. for 20 hours, and then centrifuged. The resulting supernatant was concentrated to 4 L using an ultrafiltration device equipped with hollow fibers with exclusion molecular weight of 100,000, centrifuged to remove insoluble substances and allowed to stand at 5° C. for 24 hours. The formed precipitate was removed by centrifugation. The solvent of the resulting supernatant was exchanged for 100 mm sodium chloride using an ultrafiltration device. The solution was cooled to 4° C. or below, and the pH was adjusted to 2.0 with hydrochloric acid. The formed precipitate was removed by centrifugation. The pH of the resulting supernatant was adjusted with sodium hydroxide to 8.0. The supernatant was concentrated to 4 L. The solvent was exchanged for 20 mM sodium chloride using an ultrafiltration device. Insoluble substances in the solution were removed by centrifugation. 82 ml of 50% ethanol was added to the solution. The mixture was lyophilized to obtain 76 g of a dried product of sulfated-fucose-containing polysaccharide fraction from Kjellmaniella crassifolia.

(2) Flavobacterium sp. SA-0082 (FERM BP-5402) was inoculated into 100 ml of a medium consisting of artificial seawater containing 0.2% sulfated-fucose-containing polysaccharide fraction from Kjellmaniella crassifolia prepared as described in Example 3(1), 1.0% peptone and 0.01% yeast extract (pH 7.5) in a 500-ml Erlenmeyer flask which had been sterilized at 120° C. for 20 minutes, and cultured at 24° C. for 23 hours with shaking. After cultivation, the culture was centrifuged to obtain cells and a culture supernatant.

The cells were suspended in 5 ml of 10 mM tris-hydrochloride buffer (pH 8.0) containing 0.4 M sodium chloride, sonicated and centrifuged to obtain a cell extract.

Activities of the sulfated fucogalactan-digesting enzyme of the present invention detected in the culture supernatant and the cell extract were 2 mU/ml of the medium and 2 mU/ml of the medium, respectively. It was demonstrated that nearly equal amounts of the sulfated fucogalactan-digesting enzyme of the present invention are contained in the inside and outside of the cells of the bacterium of genus Flavobacterium cultured under the conditions as described above.

Example 4

7 g of the sulfated-fucose-containing polysaccharide fraction obtained in Example 3(1) was dissolved in 700 ml of 20 mM imidazole-hydrochloride buffer (pH 8.0) containing 50 mM sodium chloride and 10% ethanol. The solution was loaded onto a 5-L DEAE-Cellulofine A-800 column (Chisso Corporation) equilibrated with the same buffer. After washing with the same buffer, elution was carried out with a gradient of 50 to 1550 mM sodium chloride. A sulfated-fucose-containing polysaccharide fraction eluted at a salt concentration of 550 to 1550 mM was collected.

The fraction contained a component which is converted into smaller molecules by the sulfated fucogalactan-digesting enzyme, i.e., the sulfated fucogalactan of the present invention at a concentration of about 10%. The fraction was desalted using an ultrafiltration device equipped with hollow fibers with exclusion molecular weight of 100,000. The solvent was exchanged for 20 mM imidazole-hydrochloride buffer (pH 8.0) containing 200 mM sodium chloride. 600 mU of the sulfated fucogalactan-digesting enzyme of the present invention was added thereto. The mixture was reacted at 25° C. for 3 days and subjected to ultrafiltration. The ultrafiltration was continued until the amount of sugar contained in the filtrate became undetectable as measured according to the phenol-sulfuric acid method. The component which is converted into smaller molecules by the sulfated fucogalactan-digesting enzyme of the present invention, i.e., the sulfated fucogalactan of the present invention could be removed from the sulfated-fucose-containing polysaccharide fraction by these steps.

Example 5

(1) Preparation of Enzymatic Digest from Sulfated Fucogalactan (i)

70 g of the sulfated-fucose-containing polysaccharide fraction from Kjellmaniella crassifolia obtained in Example 3 was dissolved in 20 mM imidazole-hydrochloride buffer (pH 7.5) containing 300 mM sodium chloride, 20 mM calcium chloride and 10% ethanol and subjected to ultrafiltration using an ultrafiltration device equipped with hollow fibers with exclusion molecular weight of 100,000 to thoroughly remove any substances which could be filtrated. The same buffer as that used above for the dissolution was used for the ultrafiltration.

5 U of the sulfated-fucose-containing polysaccharide-F-digesting enzyme obtained from a culture of Alteromonas sp. SN-1009 (FERM BP-5747) as described in WO97/26896 was added to the solution retained after the ultrafiltration. The mixture was reacted at 25° C. for 3 days. The reaction mixture was subjected to ultrafiltration using an ultrafiltration device equipped with hollow fibers with exclusion molecular weight of 100,000 to thoroughly remove substances which were converted into smaller molecules by the sulfated-fucose-containing polysaccharide-F-digesting enzyme, i.e., smaller molecules from the fucoidan. The same buffer as that used above for the reaction mixture was used for the ultrafiltration.

20 U of the sulfated-fucose-containing polysaccharide-U-digesting enzyme obtained from a culture of Flavobacterium sp. SA-0082 (FERM BP-5402) as described in WO97/26896 was added to the solution retained after the ultrafiltration. The mixture was reacted at 25° C. for 5 days. The reaction mixture was subjected to ultrafiltration using an ultrafiltration device equipped with hollow fibers with exclusion molecular weight of 100,000 to thoroughly remove substances which were converted into smaller molecules by the sulfated-fucose-containing polysaccharide-U-digesting enzyme, i.e., smaller molecules from the sulfated fucoglucuronomannan. Water was used for the ultrafiltration, which was finally exchanged for 10 mM tris-hydrochloride buffer (pH 8) containing 200 mM sodium chloride.

2 U of the sulfated fucogalactan-digesting enzyme as described in Example 2(1) was added to the solution retained after the ultrafiltration. The mixture was reacted at 25° C. for 5 days. The reaction mixture was divided into two equal portions. One portion was subjected to ultrafiltration using an ultrafiltration device equipped with hollow fibers with exclusion molecular weight of 100,000 to thoroughly ultrafiltrate substances which were converted into smaller molecules by the sulfated fucogalactan-digesting enzyme, i.e., smaller molecules from the sulfated fucogalactan. 10 mM tris-hydrochloride buffer (pH 8) containing 50 mM sodium chloride was used for the ultrafiltration. The thus obtained filtrate was designated as the enzymatic digest from sulfated fucogalactan (i).

(2) Preparation of Enzymatic Digest from Sulfated Fucogalactan (ii)

550 mU of the sulfated fucogalactan-digesting enzyme as described in Example 2(1) was added to the remaining portion of the reaction mixture divided in Example 5(1). The mixture was reacted at 25° C. for 7 days and conversion into smaller molecules was confirmed. The reaction mixture was subjected to ultrafiltration using an ultrafiltration device equipped with hollow fibers with exclusion molecular weight of 100,000 to thoroughly ultrafiltrate smaller molecules from the sulfated fucogalactan. 10 mM tris-hydrochloride buffer (pH 8) containing 50 mM sodium chloride was used for the ultrafiltration. The thus obtained filtrate was designated as the enzymatic digest from sulfated fucogalactan (ii).

(3) Separation and Purification of the Enzymatic Digest from Sulfated Fucogalactan (i)

The enzymatic digest from sulfated fucogalactan (i) obtained in Example 5(1) was concentrated to 500 ml using an evaporator, desalted using an electrodialysis device and loaded onto a 1-L DEAE-Cellulofine A-800 column (Chisso Corporation) equilibrated with 10 mM imidazole-hydrochloride buffer (pH 8) containing 10 mM sodium chloride. After washing with the same buffer, elution was carried out with a gradient of 10 mM to 900 mM sodium chloride. 62 ml of the eluate was collected for each fraction. The sugar content of each fraction was measured according to the phenol-sulfuric acid method. Fractions eluted with about 130 mM sodium chloride and about 220 mM sodium chloride formed peaks of sugar content. These fractions were collected and designated as a 130 mM-eluted fraction (i) and a 220 mM-eluted fraction (i), respectively.

The 130 mM-eluted fraction (i) was desalted using an electrodialysis device. Sodium chloride was dissolved in the fraction at a concentration of 50 mM. The solution was loaded onto a 100-ml DEAE-Cellulofine A-800 column (Chisso Corporation) equilibrated with 10 mM imidazole-hydrochloride buffer (pH 8) containing 50 mM sodium chloride. After washing with the same buffer, elution was carried out with a gradient of 50 mM to 200 mM sodium chloride. 10 ml of the eluate was collected for each fraction. The sugar content of each fraction was measured according to the phenol-sulfuric acid method. Fractions eluted with about 55 mM to about 75 mM sodium chloride formed a peak of sugar content. Fractions eluted with about 60 mM sodium chloride were collected, concentrated to 2 ml using SpeedVac (SAVANT Instruments Inc.), loaded onto a 200-ml Cellulofine GCL-25 column (Chisso Corporation) equilibrated with 10% ethanol, and eluted with the same buffer. 2 ml of the eluate was collected for each fraction. The sugar content of each fraction was measured according to the phenol-sulfuric acid method. A fraction constituting a peak of sugar content was collected and designated as (A).

On the other hand, the 220 mm-eluted fraction (i) was desalted using an electrodialysis device. Sodium chloride was dissolved in the fraction at a concentration of 100 mM. The solution was loaded onto a 100-ml DEAE-Cellulofine A-800 column (Chisso Corporation) equilibrated with 10 mM imidazole-hydrochloride buffer (pH 8) containing 100 mM sodium chloride. After washing with the same buffer, elution was carried out with a gradient of 100 mM to 350 mM sodium chloride. 10 ml of the eluate was collected for each fraction. The sugar content of each fraction was measured according to the phenol-sulfuric acid method. A fraction eluted with about 160 mM sodium chloride was collected, concentrated to 2 ml using SpeedVac (SAVANT Instruments Inc.), loaded onto a 200-ml Cellulofine GCL-25 column (Chisso Corporation) equilibrated with 10% ethanol, and eluted with the same buffer. 2 ml of the eluate was collected for each fraction. The sugar content of each fraction was measured according to the phenol-sulfuric acid method. A fraction constituting a peak of sugar content was collected and designated as (B).

(4) Separation and Purification of the Enzymatic Digest from Sulfated Fucogalactan (ii)

The enzymatic digest from sulfated fucogalactan (ii) as described in Example 5(2) was concentrated to 500 ml using an evaporator, desalted using an electrodialysis device and loaded onto a 1-L DEAE-Cellulofine A-800 column (Chisso Corporation) equilibrated with 10 mM imidazole-hydrochloride buffer (pH 8) containing 10 mM sodium chloride. After washing with the same buffer, elution was carried out with a gradient of 10 mM to 900 mM sodium chloride. 61 ml of the eluate was collected for each fraction. The sugar content of each fraction was measured according to the phenol-sulfuric acid method. Fractions eluted with about 130 mM, about 220 mM and about 270 mM sodium chloride formed peaks of sugar content. These fractions were collected and designated as a 130 mm-eluted fraction (ii), a 220 mM-eluted fraction (ii) and a 270 mM-eluted fraction (ii), respectively.

The 130 mM-eluted fraction (ii) was desalted using an electrodialysis device. Sodium chloride was dissolved in the fraction at a concentration of 20 mM. The solution was loaded onto a 200-ml DEAE-Cellulofine A-800 column (Chisso Corporation) equilibrated with 10 mM imidazole-hydrochloride buffer (pH 8) containing 20 mM sodium chloride. After washing with the same buffer, elution was carried out with a gradient of 20 mM to 150 mM sodium chloride. 13 ml of the eluate was collected for each fraction. The sugar content of each fraction was measured according to the phenol-sulfuric acid method. Fractions eluted with about 50 mM to about 70 mM sodium chloride were collected, concentrated to 30 ml using an evaporator, loaded onto a 1200-ml Cellulofine GCL-25 column (Chisso Corporation) equilibrated with 10% ethanol, and eluted with the same buffer. 10 ml of the eluate was collected for each fraction. The sugar content of each fraction was measured according to the phenol-sulfuric acid method. A fraction constituting a peak of sugar content was collected. Acetic acid was added to the fraction at a concentration of 10 mM. The pH was adjusted to 3.5 with hydrochloric acid. Sodium chloride was added thereto such that the conductivity became the same as that of 10 mM acetate buffer (pH 3.5) containing 20 mM sodium chloride. The solution was loaded onto a 30-ml DEAE-Cellulofine A-800 column (Chisso Corporation) equilibrated with 10 mM acetate buffer (pH 3.5) containing 20 mM sodium chloride. After washing with the same buffer, elution was carried out with a gradient of 20 mM to 120 mM sodium chloride. 3 ml of the eluate was collected for each fraction. The sugar content of each fraction was measured according to the phenol-sulfuric acid method. Fractions eluted with about 65 mM to about 80 mM sodium chloride were collected, and diluted with water such that the conductivity became the same as that of 10 mM acetate buffer (pH 3.5) containing 40 mM sodium chloride. The solution was loaded onto a 20-ml DEAE-Cellulofine A-800 column (Chisso Corporation) equilibrated with 10 mM acetate buffer (pH 3.5) containing 40 mM sodium chloride. After washing with the same buffer, elution was carried out with a gradient of 40 mM to 80 mm sodium chloride. 3 ml of the eluate was collected for each fraction. The sugar content of each fraction was measured according to the phenol-sulfuric acid method. Fractions eluted with about 50 mM to about 65 mM sodium chloride were collected, concentrated to 2 ml using SpeedVac (SAVANT Instruments Inc.), loaded onto a 200-ml Cellulofine GCL-25 column (Chisso Corporation) equilibrated with 10% ethanol, and eluted with the same solution. 2 ml of the eluate was collected for each fraction. The sugar content of each fraction was measured according to the phenol-sulfuric acid method. Mass spectrometric analysis of the fractions constituting peaks of sugar content demonstrated that a former fraction contained the same substance as (A) whereas a latter fraction was substantially free of the same substance as (A). The latter fraction was collected and designated as (C).

On the other hand, water was added to the 220 mM-eluted fraction (ii) such that the conductivity became the same as that of 10 mM imidazole-hydrochloride buffer containing 100 mM sodium chloride. The solution was loaded onto a 200-ml DEAE-Cellulofine A-800 column (Chisso Corporation) equilibrated with 10 mM imidazole-hydrochloride buffer (pH 8) containing 100 mM sodium chloride. After washing with the same buffer, elution was carried out with a gradient of 100 mM to 300 mM sodium chloride. 13 ml of the eluate was collected for each fraction. The sugar content of each fraction was measured according to the phenol-sulfuric acid method. Fractions eluted with about 140 mM to about 170 mM sodium chloride were collected, concentrated to 30 ml using an evaporator, loaded onto a 1200-ml Cellulofine GCL-25 column (Chisso Corporation) equilibrated with 10% ethanol, and eluted with the same solution. 10 ml of the eluate was collected for each fraction. The sugar content of each fraction was measured according to the phenol-sulfuric acid method. Mass spectrometric analysis of the collected fraction constituting a peak of sugar content suggested that the fraction contained the same substance as (B) as described in Example 5(3).

Furthermore, water was added to the 270 mm-eluted fraction (ii) such that the conductivity became the same as that of 10 mM imidazole-hydrochloride buffer (pH 8) containing 150 mM sodium chloride. The solution was loaded onto a 200-ml DEAE-Cellulofine A-800 column (Chisso Corporation) equilibrated with 10 mm imidazole-hydrochloride buffer (pH 8) containing 150 mM sodium chloride. After washing with the same buffer, elution was carried out with a gradient of 150 mM to 300 mM sodium chloride. 12 ml of the eluate was collected for each fraction. The sugar content of each fraction was measured according to the phenol-sulfuric acid method. Fractions eluted with about 160 mM to about 180 mM sodium chloride were collected, concentrated to 2 ml using SpeedVac (SAVANT Instruments Inc.), loaded onto a 200-ml Cellulofine GCL-25 column (Chisso Corporation) equilibrated with 10% ethanol, and eluted with the same solution. 2 ml of the eluate was collected for each fraction. The sugar content of each fraction was measured according to the phenol-sulfuric acid method. A fraction constituting a peak of sugar content was collected and designated as (D).

Example 6

(1) Preparation of Enzymatic Digest from Sulfated Fucogalactan (iii)

15 g of the sulfated-fucose-containing polysaccharide fraction from Kjellmaniella crassifolia obtained in Example 3 was dissolved in 1500 ml of 20 mM imidazole-hydrochloride buffer (pH 7.5) containing 300 mM sodium chloride, 20 mM calcium chloride and 10% ethanol and subjected to ultrafiltration using an ultrafiltration device equipped with hollow fibers with exclusion molecular weight of 100,000 to thoroughly remove any substances which could be filtrated. The same buffer as that used above for the reaction mixture was used for the ultrafiltration. 1 U of the sulfated-fucose-containing polysaccharide-F-digesting enzyme used in Example 5(1) was added to the solution retained after the ultrafiltration. The mixture was reacted at 25° C. for 3 days.

The reaction mixture was subjected to ultrafiltration using an ultrafiltration device equipped with hollow fibers with exclusion molecular weight of 100,000 to thoroughly remove substances which were converted into smaller molecules by the sulfated-fucose-containing polysaccharide-F-digesting enzyme, i.e., smaller molecules from the fucoidan. The same buffer as that used above for the dissolution was used for the ultrafiltration.

1 U of the sulfated-fucose-containing polysaccharide-U-digesting enzyme used in Example 5(1) was added to the solution retained after the ultrafiltration. The mixture was reacted at 25° C. for 5 days.

The reaction mixture was subjected to ultrafiltration using an ultrafiltration device equipped with hollow fibers with exclusion molecular weight of 100,000 to thoroughly remove substances which were converted into smaller molecules by the sulfated-fucose-containing polysaccharide-U-digesting enzyme, i.e., smaller molecules from the sulfated fucoglucuronomannan. 10 mm tris-hydrochloride buffer (pH 8) containing 200 mM sodium chloride and 10% ethanol was used for the ultrafiltration.

600 mU of the sulfated fucogalactan-digesting enzyme as described in Example 2(1) was added to the solution retained after the ultrafiltration. The mixture was reacted at 25° C. for 5 days. The reaction mixture was subjected to ultrafiltration using an ultrafiltration device equipped with hollow fibers with exclusion molecular weight of 100,000 to thoroughly ultrafiltrate substances which were converted into smaller molecules by the sulfated fucogalactan-digesting enzyme, i.e., smaller molecules from the sulfated fucogalactan. 10% ethanol containing 20 mM sodium chloride was used for the ultrafiltration. The thus obtained filtrate was designated as the enzymatic digest from sulfated fucogalactan (iii).

(2) Separation and Purification of the Enzymatic Digest from Sulfated Fucogalactan (iii)

The enzymatic digest from sulfated fucogalactan (iii) obtained in Example 6(1) was desalted using an electrodialysis device, concentrated to 50 ml using an evaporator and loaded onto a 100-ml DEAE-Cellulofine A-800 column (Chisso Corporation) equilibrated with 50 mM ammonium acetate (pH 5.5). After washing with the same buffer, elution was carried out with a gradient of 50 mM to 4 M ammonium acetate. 10 ml of the eluate was collected for each fraction. The sugar content of each fraction was measured according to the phenol-sulfuric acid method. Fractions eluted with about 420 mM to about 620 mM ammonium acetate formed a peak of sugar content. These fractions were collected and designated as a 420 mM to 620 mM-eluted fraction.

(3) Purification of the 420 mM to 620 mM-eluted Fraction

The fraction was desalted using an electrodialysis device. The conductivity was adjusted to that of 50 mM ammonium acetate solution. The solution was loaded onto a 100-ml DEAE-Cellulofine A-800 column (Chisso Corporation) equilibrated with 50 mM ammonium acetate (pH 5.5). After washing with the same buffer followed by 100 mM ammonium acetate (pH 5.5), elution was carried out with a gradient of 100 mM to 800 mM ammonium acetate. 10 ml of the eluate was collected for each fraction. The sugar content of each fraction was measured according to the phenol-sulfuric acid method. Fractions eluted with about 440 mM to about 530 mM ammonium acetate were collected.

The fractions were desalted using an electrodialysis device. The conductivity was adjusted to that of 200 mM ammonium acetate solution. The solution was loaded onto a 100-ml DEAE-Cellulofine A-800 column (Chisso Corporation) equilibrated with 200 mM ammonium acetate (pH 5.5). After washing with the same buffer, elution was carried out with a gradient of 200 mM to 700 mM ammonium acetate. 10 ml of the eluate was collected for each fraction. The sugar content of each fraction was measured according to the phenol-sulfuric acid method. Fractions eluted with about 420 mM to about 470 mM ammonium acetate were collected. Mass spectrometric analysis and nuclear magnetic resonance spectrometric (NMR) analysis of the fraction suggested that the fraction contained the same substance as (B) as described in Example 5(3). Mass spectrometric analysis was carried out using API-III mass spectrometer (Perkin-Elmer Sciex). NMR analysis was carried out using a nuclear magnetic resonance apparatus JMN-α500 (Nippon Denshi).

(4) Further Enzymatic Digestion and Separation/Purification of the Enzymatic Digest from Sulfated Fucogalactan Since fractions other than the 420 mM to 620 mM-eluted fraction in Example 6(2) contained substances having relatively high molecular weight, they were digested with the sulfated fucogalactan-digesting enzyme again. Briefly, The eluted fractions other than the 420 mM to 620 mM-eluted fraction were collected, and desalted using an electrodialysis device. The composition of the solution was adjusted to contain 10 mM phosphate buffer (pH 7.5), 200 mM sodium chloride and 10% ethanol. 460 mU of the sulfated fucogalactan-digesting enzyme as described in Example 2(1) was added thereto and reacted at 25° C. for 8 days. The reaction mixture was desalted using an electrodialysis device. The conductivity was adjusted to that of 50 mM ammonium acetate solution. The solution was loaded onto a 100-ml DEAE-Cellulofine A-800 column (Chisso Corporation) equilibrated with 50 mM ammonium acetate (pH 5.5). After washing with the same buffer, elution was carried out with a gradient of 100 mM to 1 M ammonium acetate. 10 ml of the eluate was collected for each fraction. The sugar content of each fraction was measured according to the phenol-sulfuric acid method. Fractions eluted with about 180 mM to about 280 mM ammonium acetate and about 360 mM to about 430 mM ammonium acetate were collected and designated as (E) and (F), respectively.

Example 7

Structural Determination of Enzymatic Digests from Sulfated Fucogalactan

The six fractions (A), (B), (C), (D), (E) and (F) obtained in Examples 5 and 6 were desalted using an electrodialysis device, lyophilized, and subjected to saccharide composition analysis and mass spectrometric analysis. Mass spectrometric analysis was carried out using API-III mass spectrometer (Perkin-Elmer Sciex). NMR analysis was carried out using a nuclear magnetic resonance apparatus JNM-α500 (Nippon Denshi). Samples were subjected to structural analysis after exchange for heavy water according to a conventional method. Bonds of constituting saccharides were analyzed using the HMBC method, a method for $^1$H-detected heteronuclear multiple bond connectivity. The DQF-COSY method and the HOHAHA method were used for identification in $^1$H-NMR. The HSQC method was used for identification in $^{13}$C-NMR.

(1) Physical Properties of Smaller Molecule (A)

Figure 3:
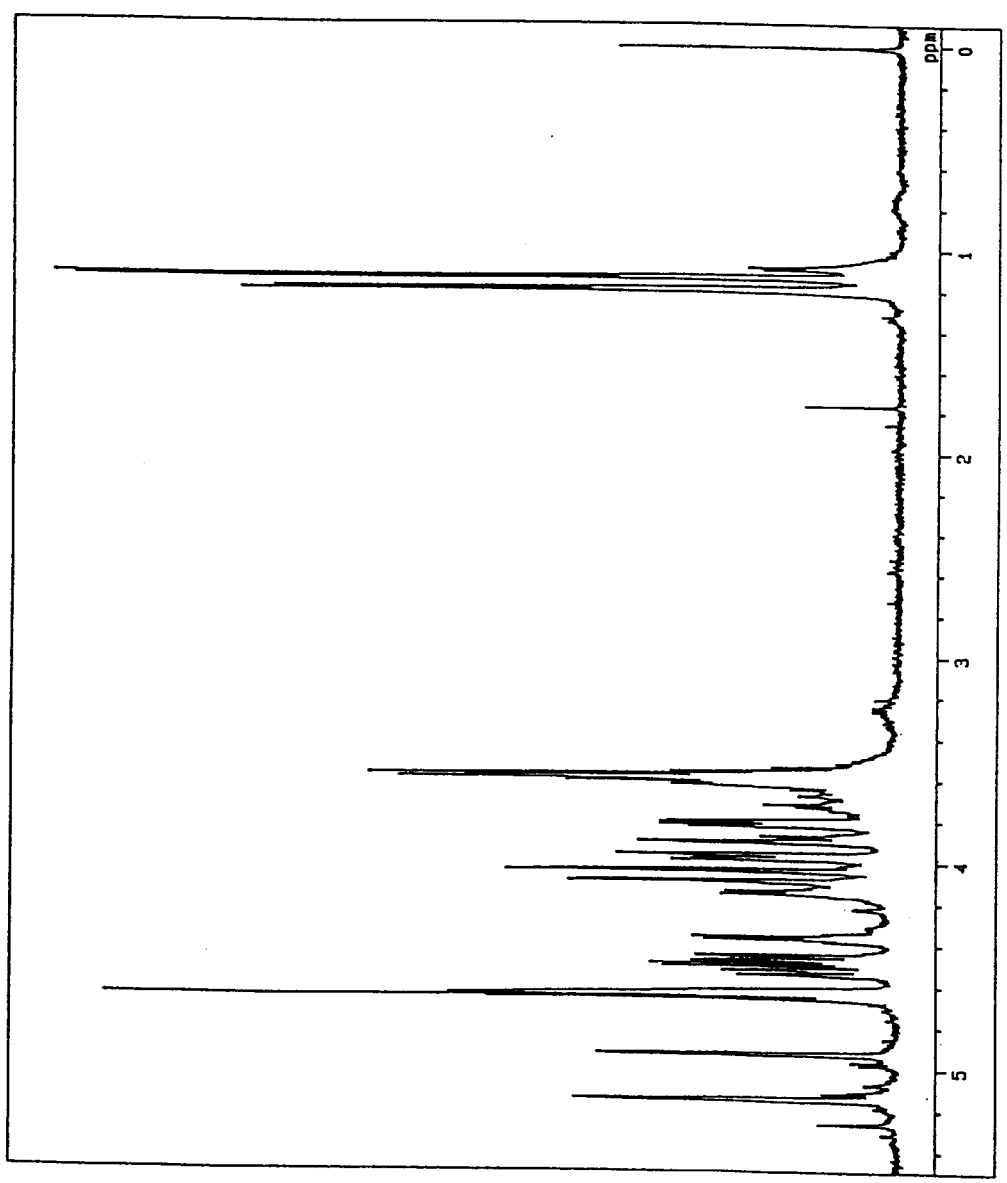
FIG. 3: a figure which illustrates the $^1$H-NMR spectrum of the smaller molecule (A) from the sulfated fucogalactan according to the present invention.
Figure 4:
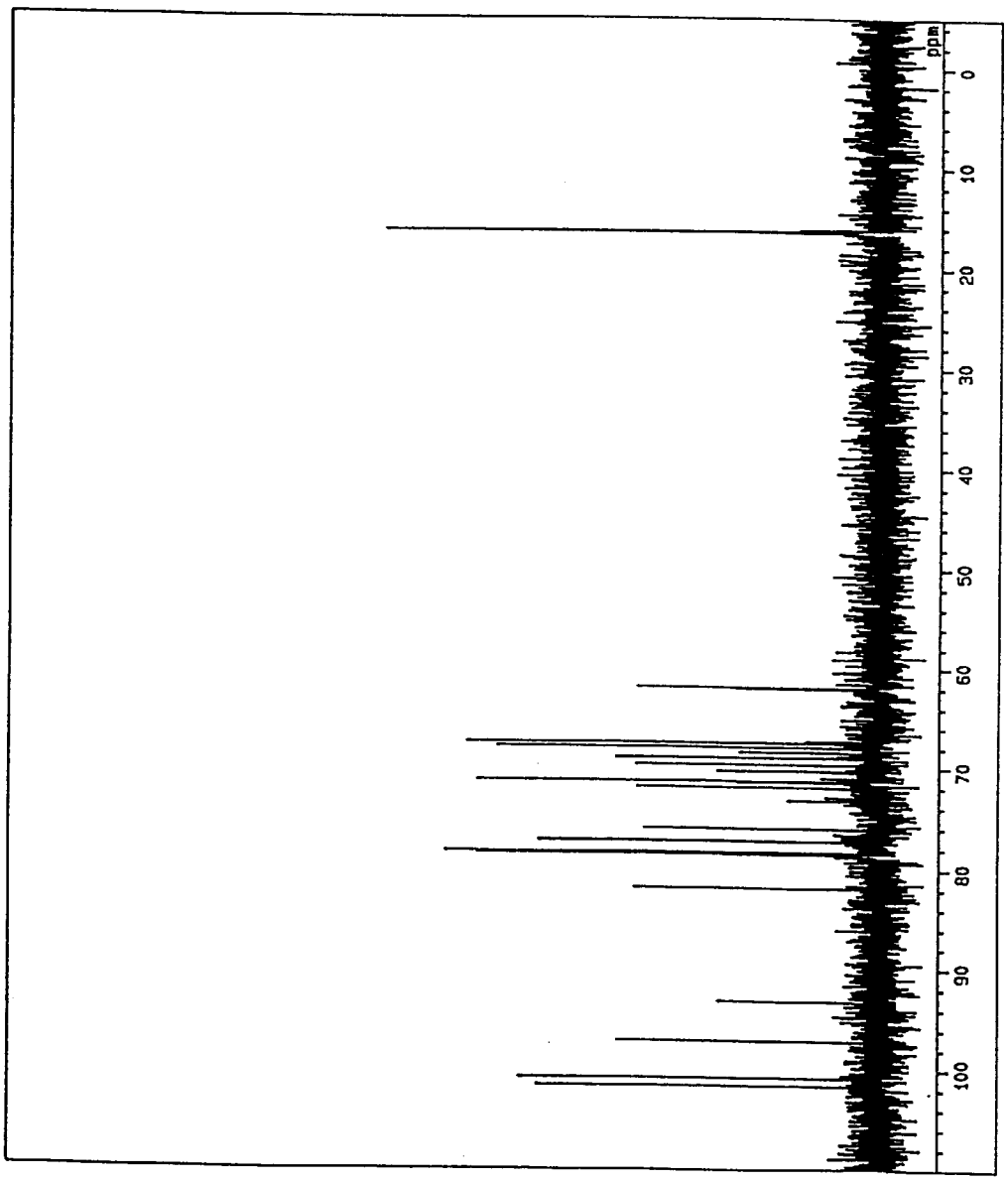
FIG. 4: a figure which illustrates the $^{13}$C-NMR spectrum of the smaller molecule (A) from the sulfated fucogalactan according to the present invention.
Figure 5:
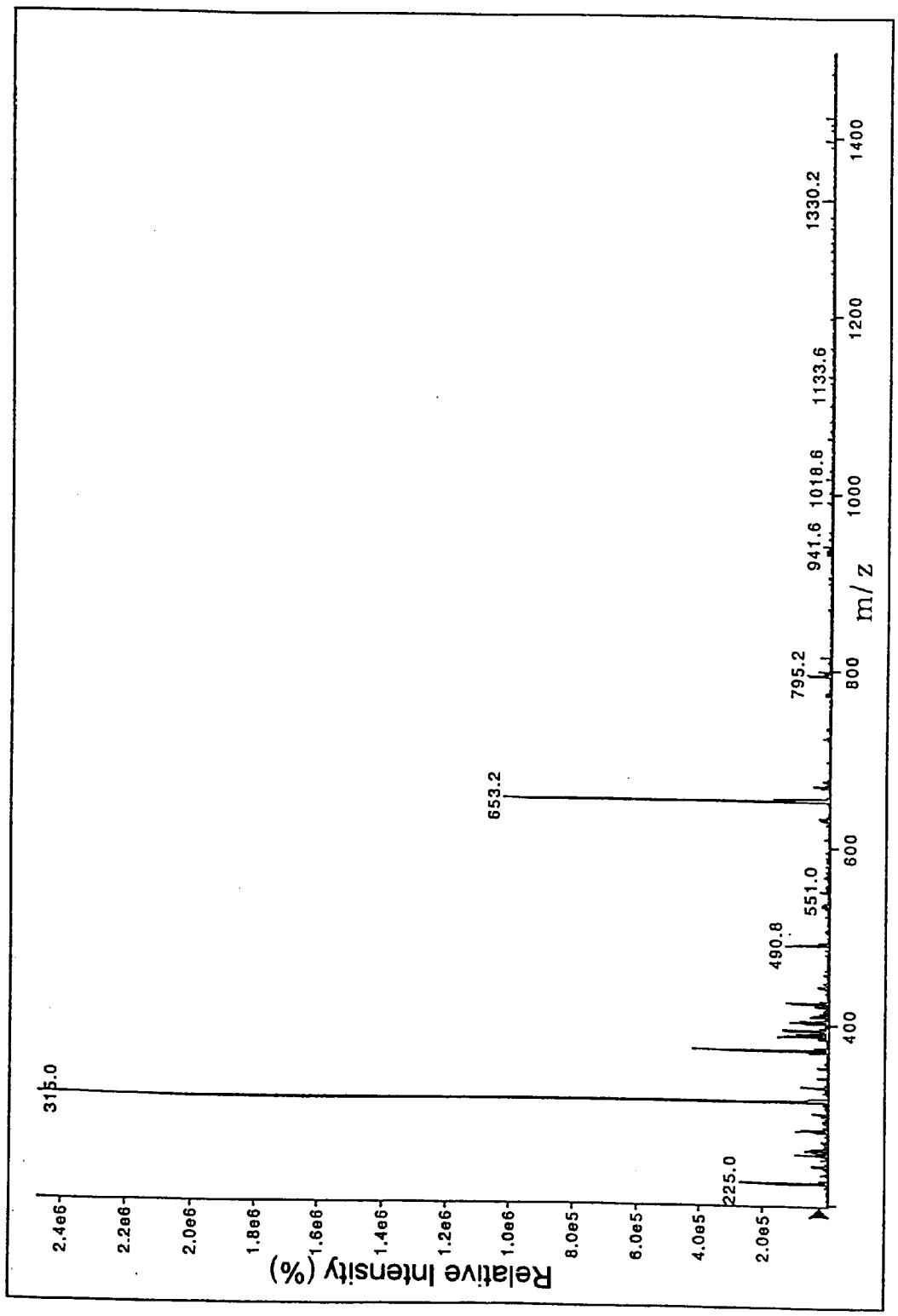
FIG. 5: a figure which illustrates the mass spectrum of the smaller molecule (A) from the sulfated fucogalactan according to the present invention.

The results for mass spectrometric analysis and identification in NMR are shown below. The $^1$H-NMR spectrum, $^{13}$C-NMR spectrum and mass spectrum of the smaller molecule (A) from the sulfated fucogalactan of the present invention are illustrated in FIGS. 3, 4 and 5, respectively. FIG. 3 is a figure which illustrates the $^1$H-NMR spectrum of the smaller molecule (A) from the sulfated fucogalactan of the present invention. FIG. 4 is a figure which illustrates the $^{13}$C-NMR spectrum of the smaller molecule (A) from the sulfated fucogalactan of the present invention. FIG. 5 is a figure which illustrates the mass spectrum of the smaller molecule (A) from the sulfated fucogalactan of the present invention. In FIGS. 3 and 4, the vertical axes represent the signal intensity and the horizontal axes represent the chemical shift value (ppm). In FIG. 5, the vertical axis represents the relative intensity (%) and the horizontal axis represents the m/z value.

Molecular weight: 632; MS m/z 653.2 [M+Na$^+$–2H$^+$]$^-$, 315.0 [M–2H$^+$]$^{2-}$ $^1$H-NMR(D$_2$O); δ; 5.15 (1H, d, J=4.3 Hz, F1-1-H), 4.93 (1H, d, J=3.7 Hz, F2-1-H), 4.53 (1H, d-d, J=10.4, 4.3 Hz, F1-3-H), 4.49 (1H, d, J=7.6 Hz, G1-1-H), 4.46 (1H, d-d, J=10.7, 3.1 Hz, F2-3-H), 4.36 (1H, q, J=6.7 Hz, F2-5-H), 4.14 (1H, q, J=6.7 Hz, F1-5-H), 4.09 (1H, d, J=2.4 Hz, F1-4-H), 4.03 (1H, d, J=3.1 Hz, F2-4-H), 3.97 (1H, d-d, J=10.4, 4.3 Hz, F1-2-H), 3.90 (1H, br-s, G1-4-H), 3.81 (1H, d-d, J=10.7, 3.7 Hz, F2-2-H), 3.59 (1H, m, G1-3-H), 3.59 (1H, m, G1-5-H), 3.59 (2H, m, G1-6-H), 3.56 (1H, m, G1-2-H), 1.19 (3H, d, J=6.7, F1-6-H), 1.14 (3H, d, J=6.7, F2-6-H); $^{13}$C-NMR(D$_2$O).

Chemical shift values for the respective carbons in $^{13}$C-NMR analysis are shown in Table 1.

TABLE 1

| Carbon position | $^{13}$C-NMR chemical shift value (ppm) |
|---|---|
| G1-1 | 97.1 |
| G1-2 | 71.9 |
| G1-3 | 81.8 |
| G1-4 | 69.6 |
| G1-5 | 76.0 |
| G1-6 | 61.8 |
| F1-1 | 101.6 |
| F1-2 | 67.4 |
| F1-3 | 77.2 |
| F1-4 | 78.2 |
| F1-5 | 68.9 |
| F1-6 | 16.4 |
| F2-1 | 100.8 |
| F2-2 | 67.4 |
| F2-3 | 78.5 |
| F2-4 | 71.3 |
| F2-5 | 67.9 |
| F2-6 | 16.2 |

Saccharide composition: L-fucose: D-galactose=2:1 Sulfate group: 2 molecules

The numbers for peak identification in $^1$H-NMR are as indicated in formula (V) below.

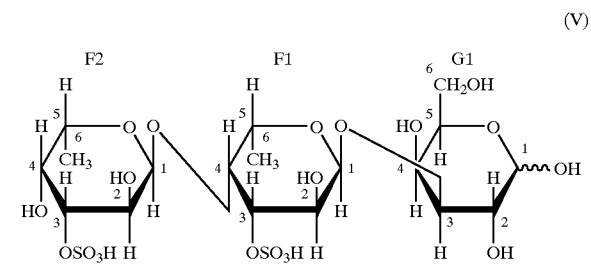

(V)

(2) Physical Properties of Smaller Molecule (B)

Figure 6:
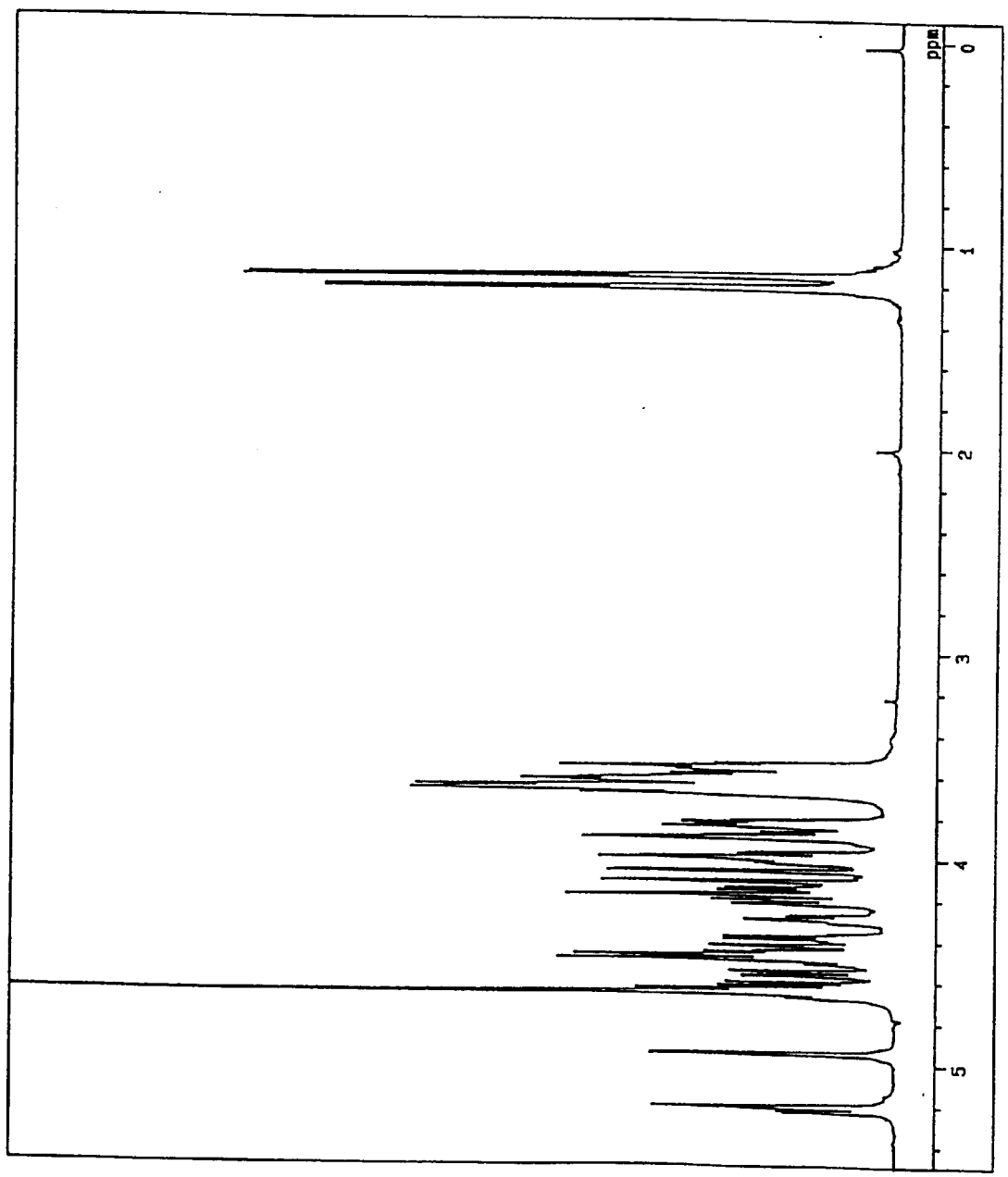
FIG. 6: a figure which illustrates the $^1$H-NMR spectrum of the smaller molecule (B) from the sulfated fucogalactan according to the present invention.
Figure 7:
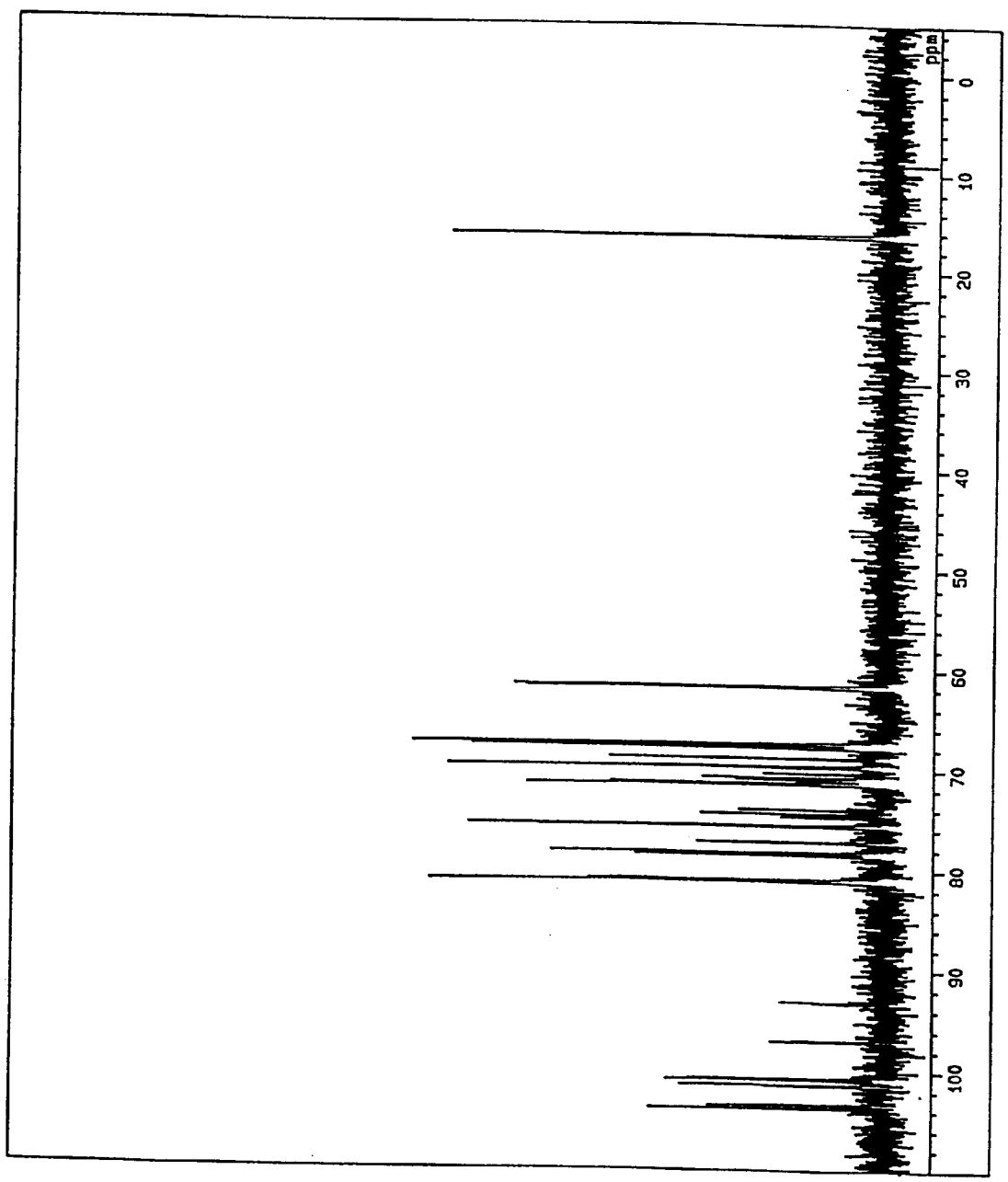
FIG. 7: a figure which illustrates the $^{13}$C-NMR spectrum of the smaller molecule (B) from the sulfated fucogalactan according to the present invention.
Figure 8:
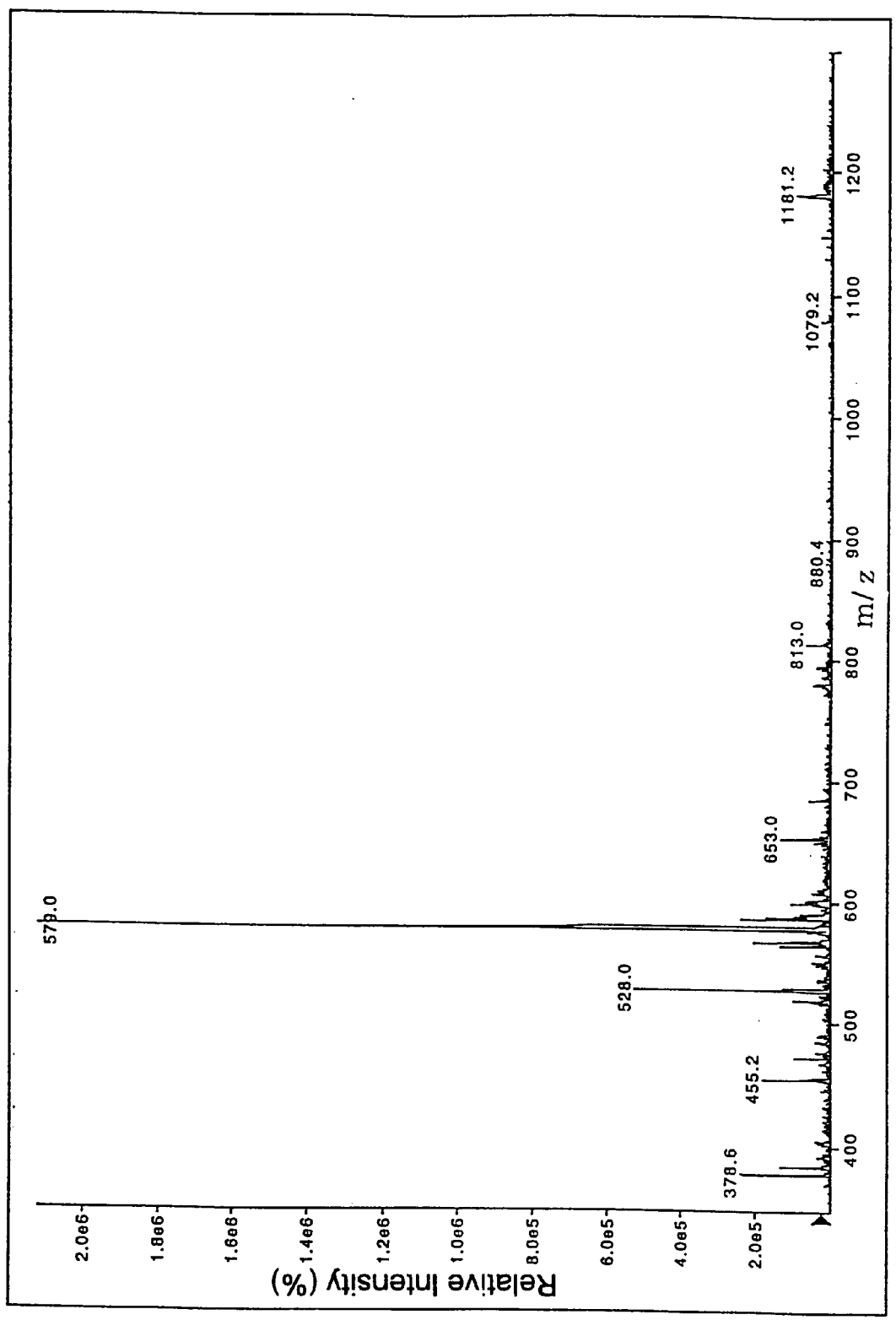
FIG. 8: a figure which illustrates the mass spectrum of the smaller molecule (B) from the sulfated fucogalactan according to the present invention.

The results for mass spectrometric analysis and identification in NMR are shown below. The $^1$H-NMR spectrum, $^{13}$C-NMR spectrum and mass spectrum of the smaller molecule (B) from the sulfated fucogalactan of the present invention are illustrated in FIGS. 6, 7 and 8, respectively. FIG. 6 is a figure which illustrates the $^1$H-NMR spectrum of the smaller molecule (B) from the sulfated fucogalactan of the present invention. FIG. 7 is a figure which illustrates the $^{13}$C-NMR spectrum of the smaller molecule (B) from the sulfated fucogalactan of the present invention. FIG. 8 is a figure which illustrates the mass spectrum of the smaller molecule (B) from the sulfated fucogalactan of the present invention. In FIGS. 6 and 7, the vertical axes represent the signal intensity and the horizontal axes represent the chemical shift value (ppm). In FIG. 8, the vertical axis represents the relative intensity (%) and the horizontal axis represents the m/z value. Molecular weight: 1116; MS m/z 1181.2 [M+3Na$^+$–4H$^+$]$^-$, 579.0 [M+2Na$^+$–4H$^+$]$^{2-}$, 378.6 [M+Na$^+$–4H$^+$]$^{3-}$; $^1$H-NMR(D$_2$O); δ; 5.20 (1H, d, J=4.3 Hz, F1-1-H), 4.95 (1H, d, J=3.7 Hz, F2-1-H), 4.64 (1H, overlapped with HOD, G1-1-H), 4.60 (1H, d, J=7.9 Hz, G2-1-H), 4.55 (1H, d-d, J=10.7, 1.8 Hz, F1-3-H), 4.47 (1H, m, F2-3-H), 4.45

(1H, d, J=7.6 Hz, G3-1-H), 4.42 (1H, br-s, G2-4-H), 4.38 (1H, q, J=6.4 Hz, F2-5-H), 4.28 (1H, m, G2-3-H), 4.20 (1H, m, G3-3-H), 4.17 (1H, br-s, G3-4-H), 4.14 (1H, q, J=6.4 Hz, F1-5-H), 4.11 (1H, d, J=1.8 Hz, F1-4-H), 4.06 (1H, d, J=1.8 Hz, F2-4-H), 4.01 (1H, m, G2-6-H), 3.97 (1H, d-d, J=10.7, 4.3 Hz, F1-2-H), 3.90 (1H, br-s, G1-4-H), 3.88 (1H, m, G2-5-H), 3.83 (1H, m, G2-6-H), 3.82 (1H, m, F2-2-H), 3.68 (1H, m, G1-3-H), 3.66 (1H, m, G2-2-H), 3.65 (2H, m, G3-6-H), 3.62 (1H, m, G3-5-H), 3.61 (2H, m, G1-6-H), 3.59 (1H, m, G1-2-H), 3.55 (1H, m, G1-5-H), 3.54 (1H, m, G3-2-H), 1.21 (3H, d, J=6.4, F1-6-H), 1.15 (3H, d, J=6.4, F2-6-H); $^{13}$C-NMR(D$_2$O).

Chemical shift values for the respective carbons in $^{13}$C-NMR analysis are shown in Table 2.

TABLE 2

| Carbon position | $^{13}$C-NMR chemical shift value (ppm) |
|---|---|
| G1-1 | 103.4 |
| G1-2 | 71.4 |
| G1-3 | 81.0 |
| G1-4 | 69.6 |
| G1-5 | 75.6 |
| G1-6 | 61.6 |
| G2-1 | 97.0 |
| G2-2 | 70.3 |
| G2-3 | 80.9 |
| G2-4 | 73.9 |
| G2-5 | 74.3 |
| G2-6 | 70.7 |
| G3-1 | 103.8 |
| G3-2 | 69.6 |
| G3-3 | 81.0 |
| G3-4 | 67.4 |
| G3-5 | 75.5 |
| G3-6 | 61.7 |
| F1-1 | 101.3 |
| F1-2 | 67.4 |
| F1-3 | 77.2 |
| F1-4 | 78.2 |
| F1-5 | 68.8 |
| F1-6 | 16.3 |
| F2-1 | 100.8 |
| F2-2 | 67.4 |
| F2-3 | 78.5 |
| F2-4 | 71.2 |
| F2-5 | 67.7 |
| F2-6 | 16.2 |

Saccharide composition: L-fucose: D-galactose=2:3
Sulfate group: 4 molecules

The numbers for peak identification in $^1$H-NMR are as indicated in formula (VI) below.

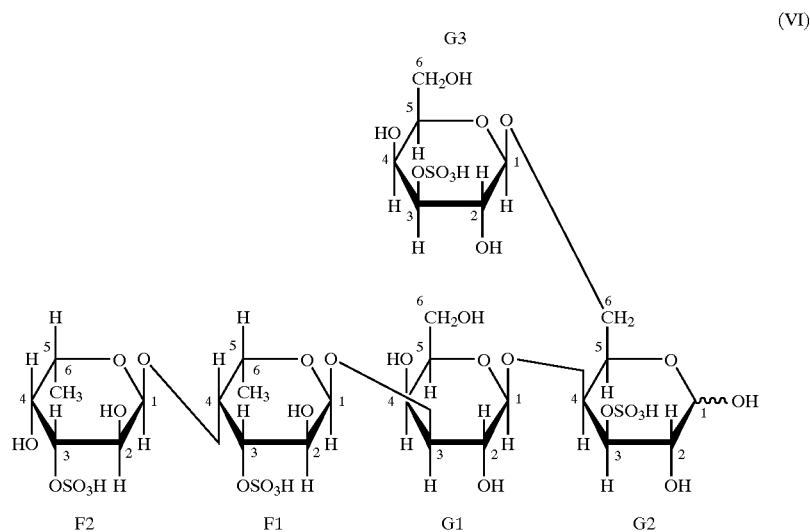

(VI)

(3) Physical Properties of Smaller Molecule (C)

Figure 9:
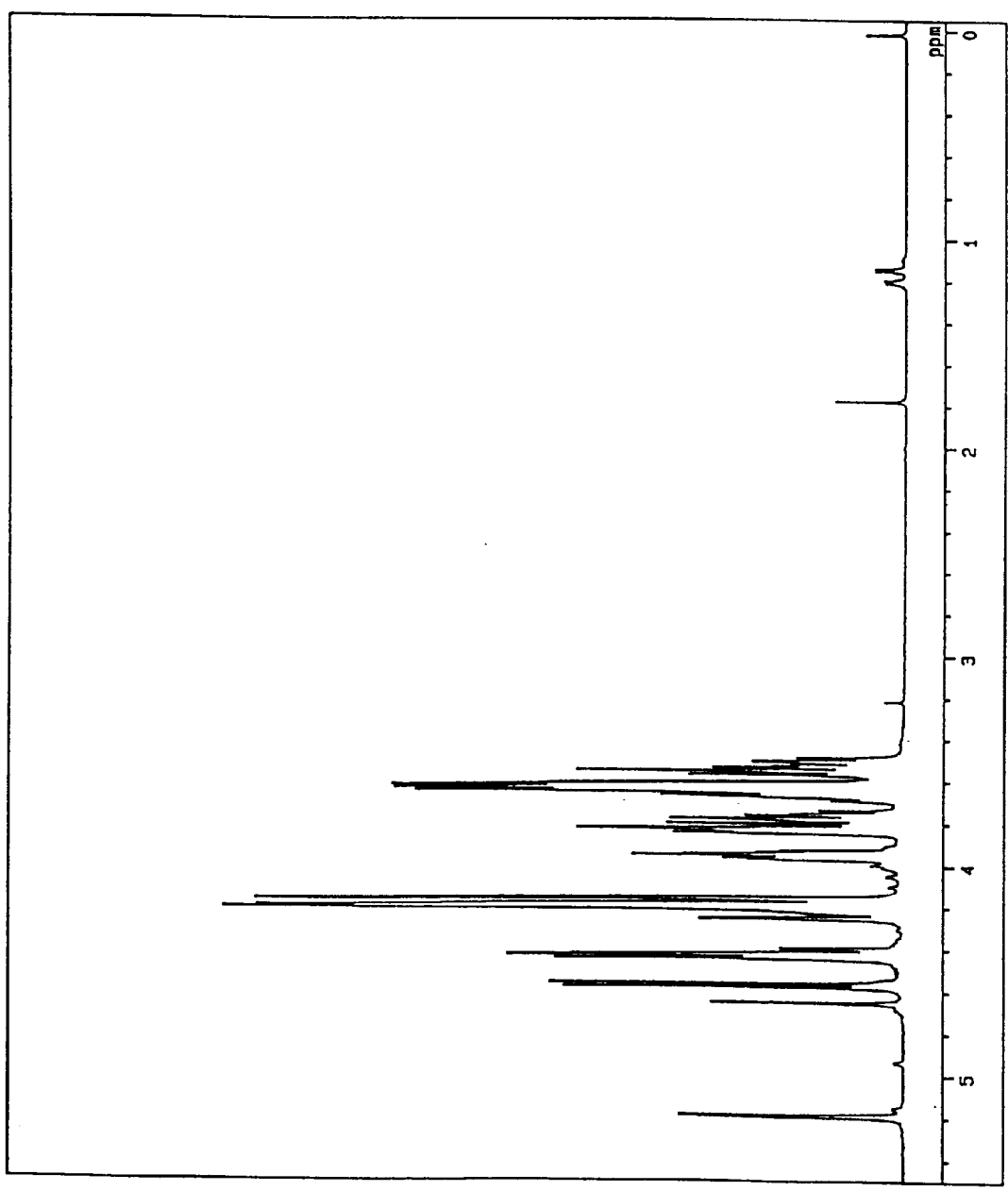
FIG. 9: a figure which illustrates the $^1$H-NMR spectrum of the smaller molecule (C) from the sulfated fucogalactan according to the present invention.
Figure 10:
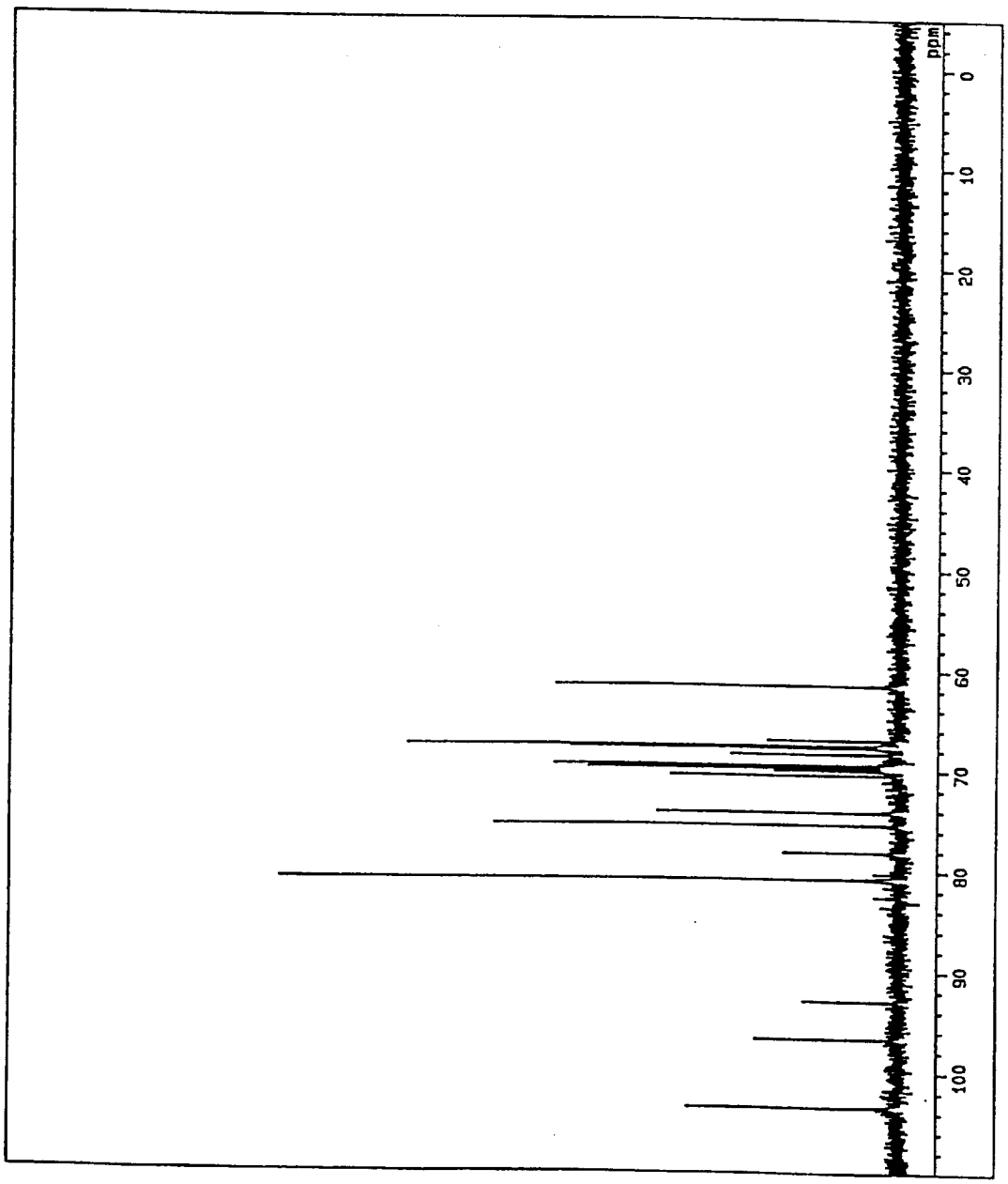
FIG. 10: a figure which illustrates the $^{13}$C-NMR spectrum of the smaller molecule (C) from the sulfated fucogalactan according to the present invention.
Figure 11:
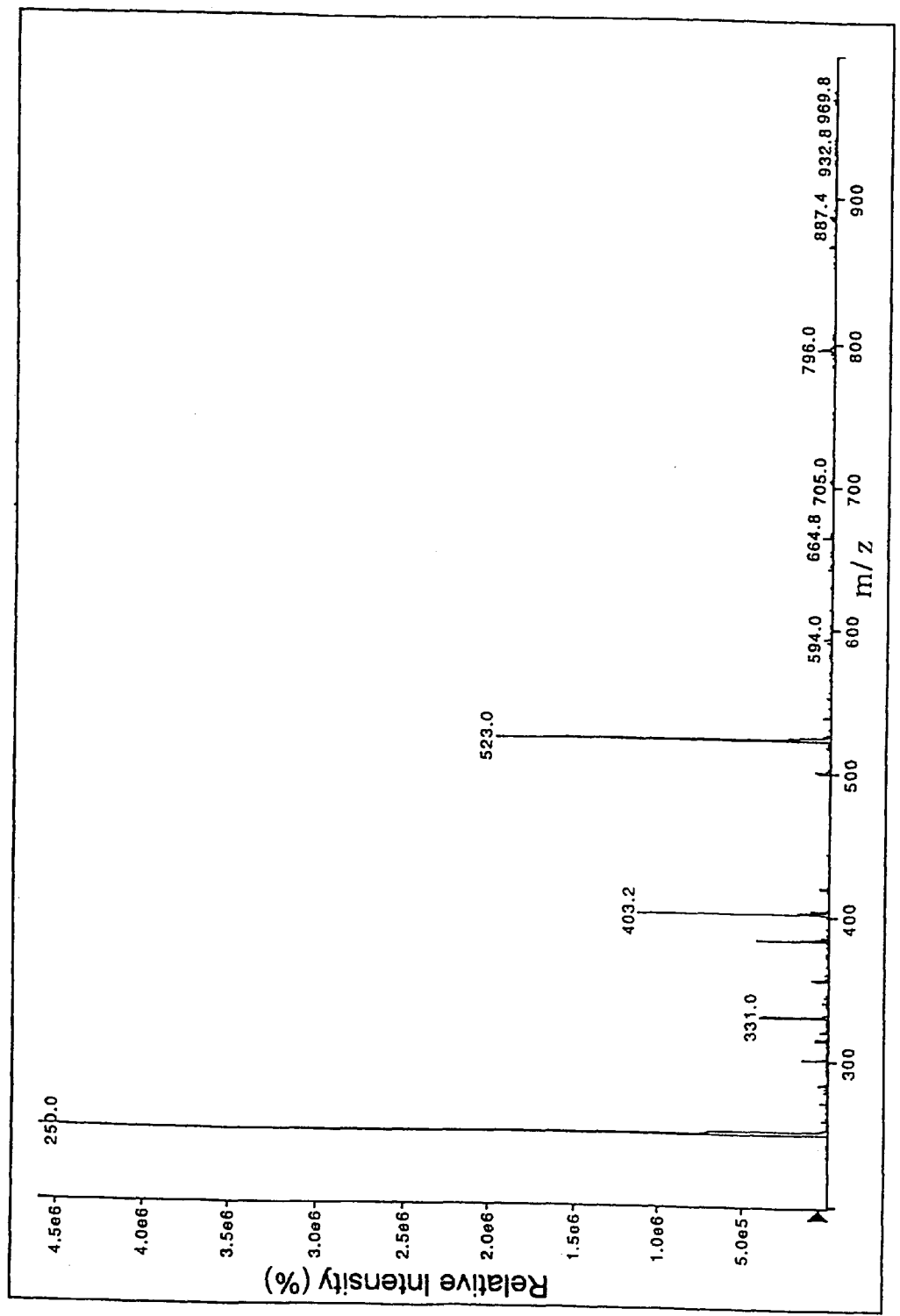
FIG. 11: a figure which illustrates the mass spectrum of the smaller molecule (C) from the sulfated fucogalactan according to the present invention.

The results for mass spectrometric analysis and identification in NMR are shown below. The $^1$H-NMR spectrum, $^{13}$C-NMR spectrum and mass spectrum of the smaller molecule (C) from the sulfated fucogalactan of the present invention are illustrated in FIGS. 9, 10 and 11, respectively. FIG. 9 is a figure which illustrates the $^1$H-NMR spectrum of the smaller molecule (C) from the sulfated fucogalactan of the present invention. FIG. 10 is a figure which illustrates the $^{13}$C-NMR spectrum of the smaller molecule (C) from the sulfated fucogalactan of the present invention. FIG. 11 is a figure which illustrates the mass spectrum of the smaller molecule (C) from the sulfated fucogalactan of the present invention. In FIGS. 9 and 10, the vertical axes represent the signal intensity and the horizontal axes represent the chemical shift value (ppm). In FIG. 11, the vertical axis represents the relative intensity (%) and the horizontal axis represents the m/z value.

Molecular weight: 502; MS m/z 523 [M+Na$^+$−2H$^{+1-}$, 250 [M−2H$^+$]$^{2-}$; $^1$H-NMR(D$_2$O); δ 4.57 (1H, d, J=7.9 Hz, G1-1H), 4.43 (1H, d, J=7.9 Hz, G2-1-H), 4.20 (1H, br-s, G1-3-H), 4.20 (1H, br-s, G1-4-H), 4.20 (1H, br-s, G2-3-H), 4.15 (1H, br-s, G2-4-H), 3.95 (1H, m, G1-6-H), 3.82 (1H, m, G1-5-H), 3.80 (1H, m, G1-6-H), 3.63 (2H, m, G2-6-H), 3.62 (1H, m, G2-5-H), 3.55 (1H, m, G2-2-H), 3.50 (1H, m, G1-2-H); $^{13}$C-NMR(D$_2$O).

Chemical shift values for the respective carbons in $^{13}$C-NMR analysis are shown in Table 3.

TABLE 3

| Carbon position | $^{13}$C-NMR chemical shift value (ppm) |
|---|---|
| G1-1 | 96.7 |
| G1-2 | 70.4 |
| G1-3 | 80.7 |
| G1-4 | 67.6 |
| G1-5 | 74.0 |
| G1-6 | 69.7 |
| G2-1 | 103.4 |
| G2-2 | 69.4 |

TABLE 3-continued

| Carbon position | $^{13}$C-NMR chemical shift value (ppm) |
|---|---|
| G2-3 | 80.7 |
| G2-4 | 67.4 |
| G2-5 | 75.3 |
| G2-6 | 61.4 |

Saccharide composition: D-galactose

Sulfate group: 2 molecules

The numbers for peak identification in $^1$H-NMR are as indicated in formula (VII) below.

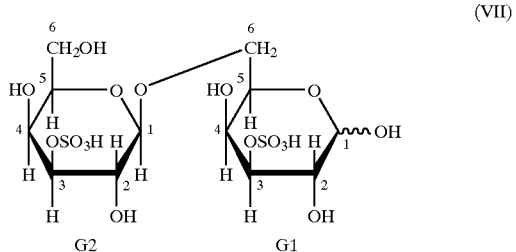

(VII)

(4) Physical Properties of Smaller Molecule (D)

Figure 12:
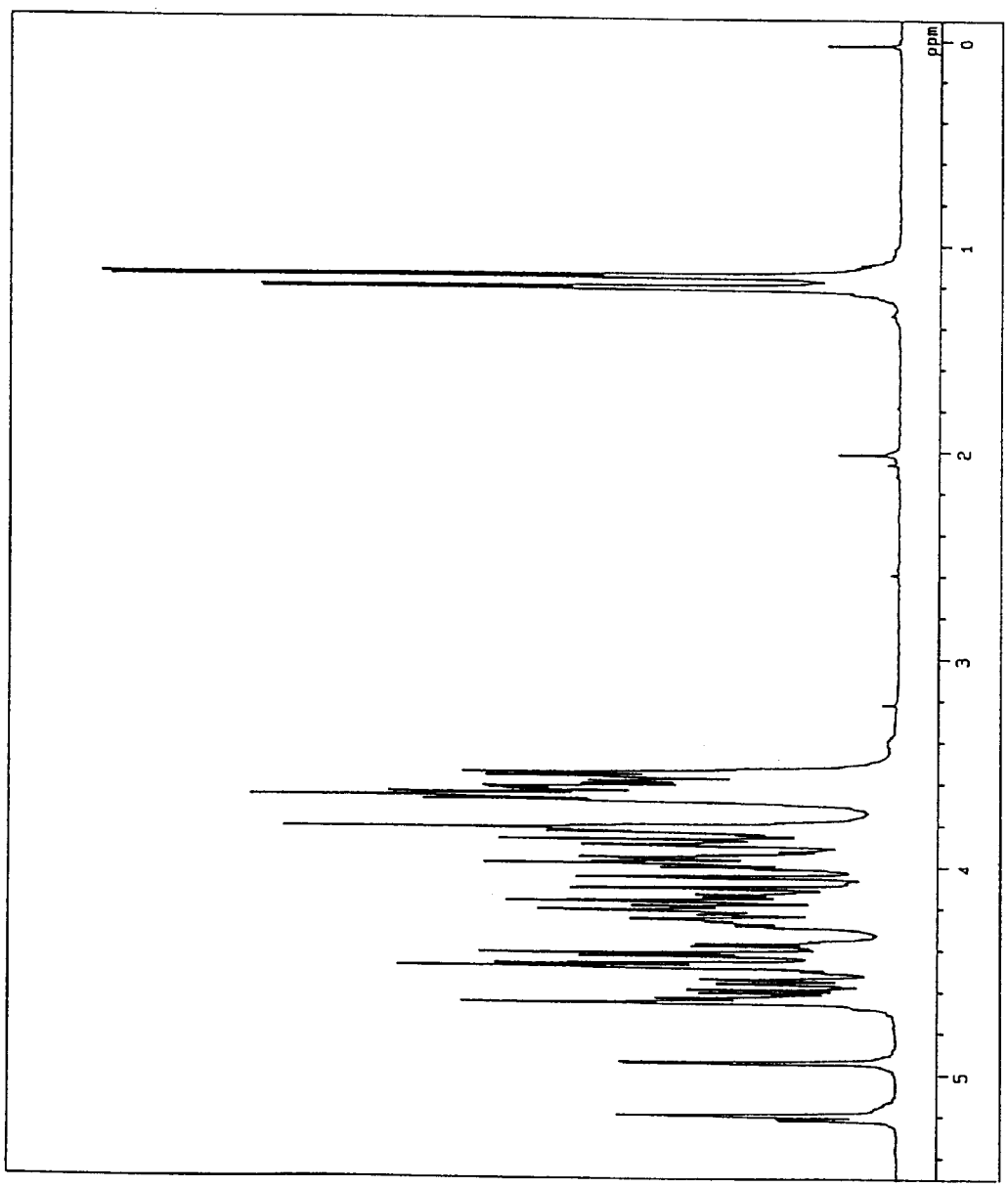
FIG. 12: a figure which illustrates the $^1$H-NMR spectrum of the smaller molecule (D) from the sulfated fucogalactan according to the present invention.
Figure 13:
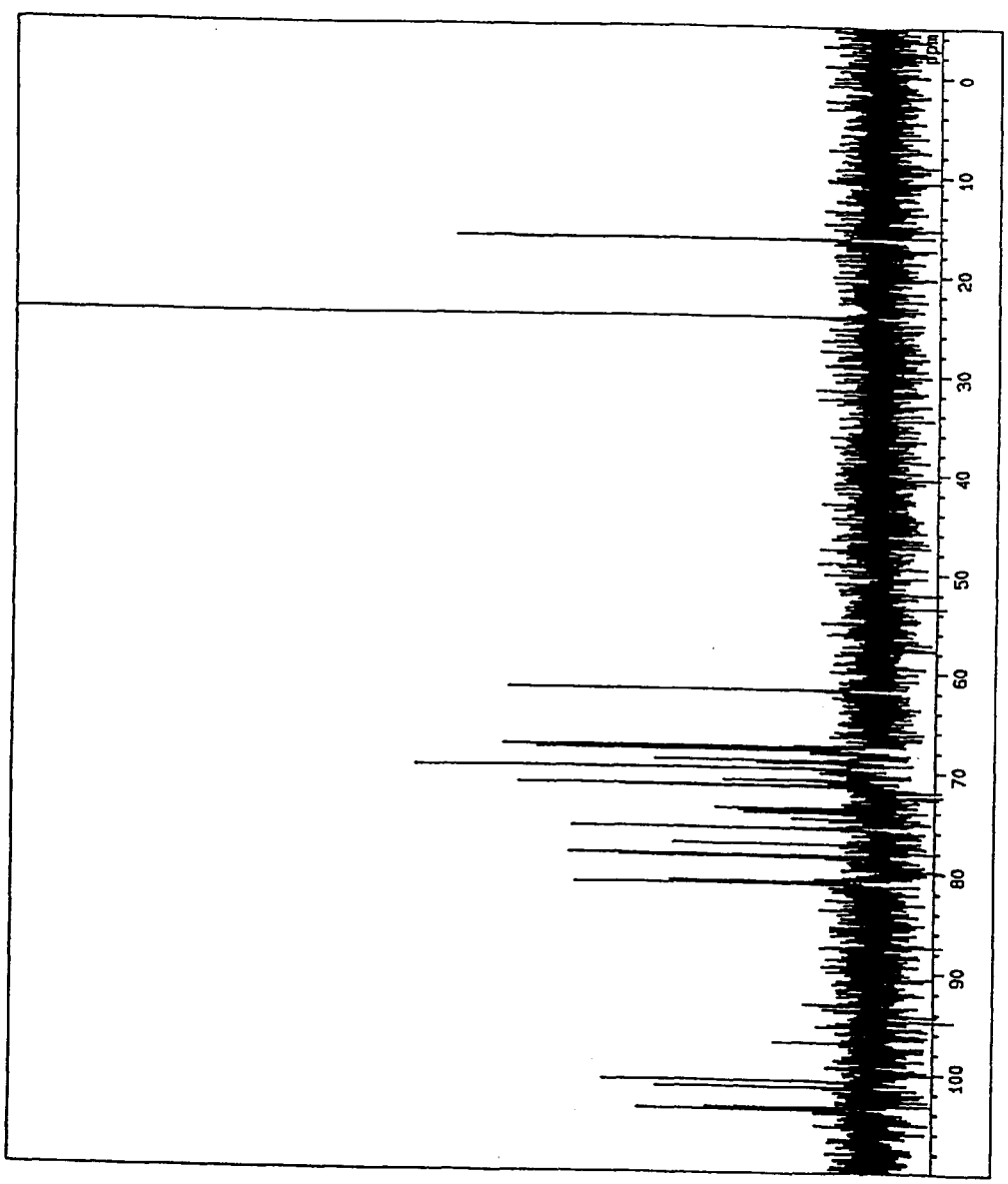
FIG. 13: a figure which illustrates the $^{13}$C-NMR spectrum of the smaller molecule (D) from the sulfated fucogalactan according to the present invention.
Figure 14:
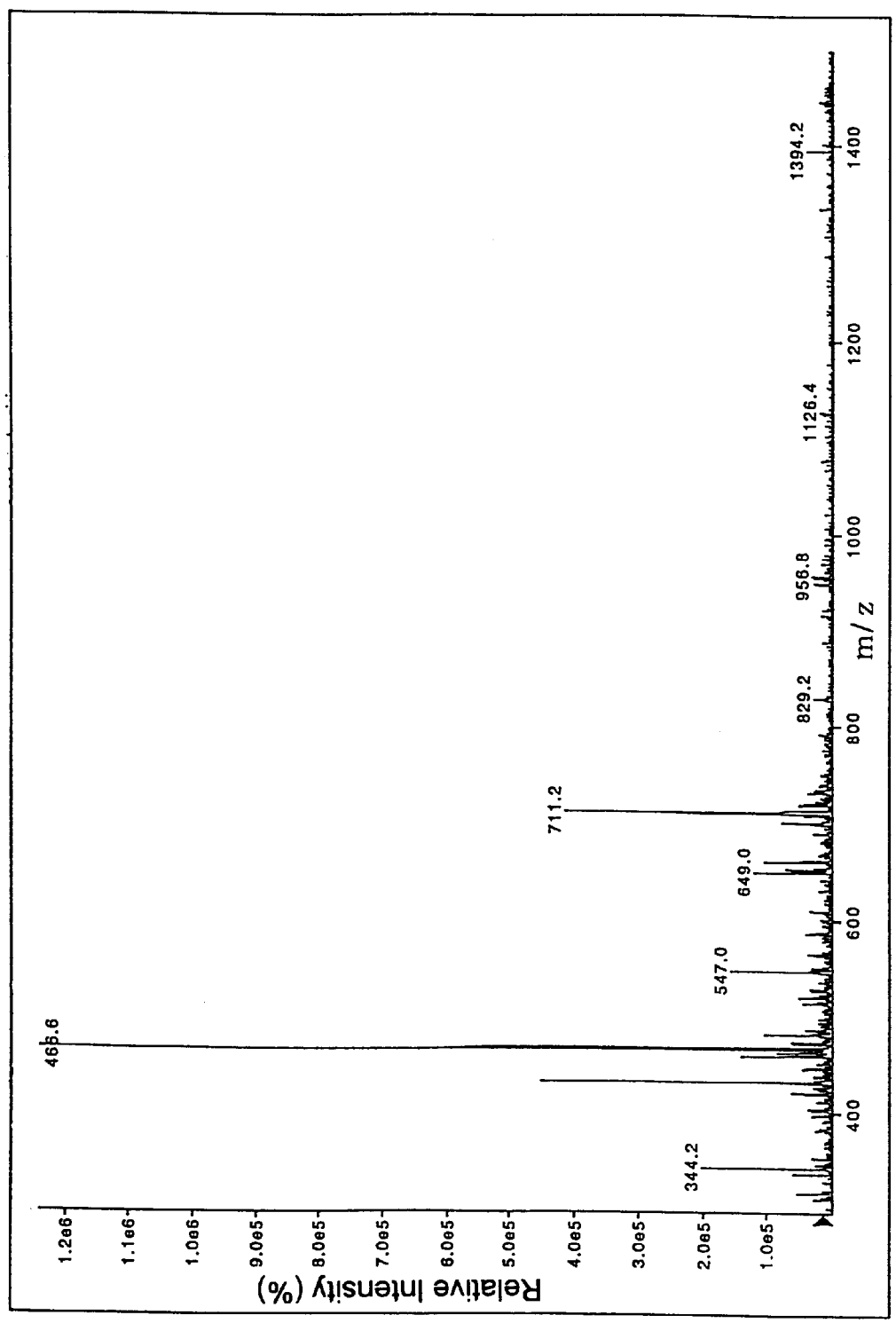
FIG. 14: a figure which illustrates the mass spectrum of the smaller molecule (D) from the sulfated fucogalactan according to the present invention.

The results for mass spectrometric analysis and identification in NMR are shown below. The $^1$H-NMR spectrum, $^{13}$C-NMR spectrum and mass spectrum of the smaller molecule (D) from the sulfated fucogalactan of the present invention are illustrated in FIGS. 12, 13 and 14, respectively. FIG. 12 is a figure which illustrates the $^1$H-NMR spectrum of the smaller molecule (D) from the sulfated fucogalactan of the present invention. FIG. 13 is a figure which illustrates the $^{13}$C-NMR spectrum of the smaller molecule (D) from the sulfated fucogalactan of the present invention. FIG. 14 is a figure which illustrates the mass spectrum of the smaller molecule (D) from the sulfated fucogalactan of the present invention. In FIGS. 12 and 13, the vertical axes represent the signal intensity and the horizontal axes represent the chemical shift value (ppm) In FIG. 14, the vertical axis represents the relative intensity (%) and the horizontal axis represents the m/z value.

Molecular weight: 1358; MS m/z 711.2 $[M+3Na^+-5H^+]^{2-}$, 466.6 $[M+2Na^+-5H^+]^{3-}$, 344.2; $[M+Na^+-5H^+]^{4-}$; $^1$H-NMR(D$_2$O); δ; 5.19 (1H, d, J=4.3 Hz, F1-1-H), 4.93 (1H, d, J=3.7 Hz, F2-1-H), 4.62 (1H, overlapped with HOD, G1-1-H), 4.59 (1H, overlapped with HOD, G2-1-H), 4.54 (1H, d-d, J=10.6, 2.7 Hz, F1-3-H), 4.46 (1H, d, J=7.6 Hz, G3-1-H), 4.46 (1H, m, F2-3-H), 4.41 (1H, br-s, G2-4-H), 4.41 (1H, d, J=7.6 Hz, G4-1-H), 4.37 (1H, q, J=6.4 Hz, F2-5-H), 4.27 (1H, m, G2-3-H), 4.24 (1H, br-s, G3-4-H), 4.21 (1H, m, G3-3-H), 4.19 (1H, m, G4-3-H), 4.15 (1H, br-s, G4-4-H), 4.13 (1H, q, J=6.7 Hz, F1-5-H), 4.09 (1H, d, J=2.7 Hz, F1-4-H), 4.04 (1H, d, J=2.8 Hz, F2-4-H), 3.98 (1H, m, G2-6-H), 3.96 (1H, d-d, J=10.6, 4.3 Hz, F1-2-H), 3.93 (1H, m, G3-6-H), 3.88 (1H, br-s, G1-4-H), 3.86 (1H, m, G2-5-H), 3.81 (1H, m, G2-6-H), 3.81 (1H, m, F2-2-H), 3.80 (1H, m, G3-5-H), 3.80 (1H, m, G3-6-H), 3.66 (1H, m, G1-3-H), 3.65 (1H, m, G2-2-H), 3.64 (1H, m, G1-6-H), 3.64 (1H, m, G4-6-H), 3.61 (1H, m, G4-5-H), 3.58 (1H, m, G1-2-H), 3.56 (1H, m, G1-6-H), 3.56 (1H, m, G4-6-H), 3.55 (1H, m, G4-2-H), 3.54 (1H, m, G1-5-H), 3.54 (1H, m, G3-2-H), 1.20 (3H, d, J=6.7, F1-6-H), 1.14 (3H, d, J=6.4, F2-6-H); $^{13}$C-NMR(D$_2$O).

Chemical shift values for the respective carbons in $^{13}$C-NMR analysis are shown in Tables 4 and 5.

TABLE 4

| Carbon position | $^{13}$C-NMR chemical shift value (ppm) |
|---|---|
| G1-1 | 103.4 |
| G1-2 | 71.4 |
| G1-3 | 80.9 |
| G1-4 | 69.5 |
| G1-5 | 75.6 |
| G1-6 | 61.7 |
| G2-1 | 97.0 |
| G2-2 | 70.7 |
| G2-3 | 80.9 |
| G2-4 | 73.8 |
| G2-5 | 74.1 |
| G2-6 | 70.8 |
| G3-1 | 103.7 |
| G3-2 | 69.5 |
| G3-3 | 80.8 |
| G3-4 | 67.4 |
| G3-5 | 73.6 |
| G3-6 | 69.0 |
| G4-1 | 103.6 |
| G4-2 | 69.5 |
| G4-3 | 81.1 |
| G4-4 | 67.7 |
| G4-5 | 75.5 |
| G4-6 | 61.7 |

TABLE 5

(continued from Table 4)

| Carbon position | $^{13}$C-NMR chemical shift value (ppm) |
|---|---|
| F1-1 | 101.4 |
| F1-2 | 67.4 |
| F1-3 | 77.1 |
| F1-4 | 78.2 |
| F1-5 | 68.8 |
| F1-6 | 16.3 |
| F2-1 | 100.8 |
| F2-2 | 67.4 |
| F2-3 | 78.4 |
| F2-4 | 71.2 |
| F2-5 | 67.8 |
| F2-6 | 16.2 |

Saccharide composition: L-fucose: D-galactose=2:4
Sulfate group: 5 molecules

The numbers for peak identification in ¹H-NMR are as indicated in formula (VIII) below.

(VIII)

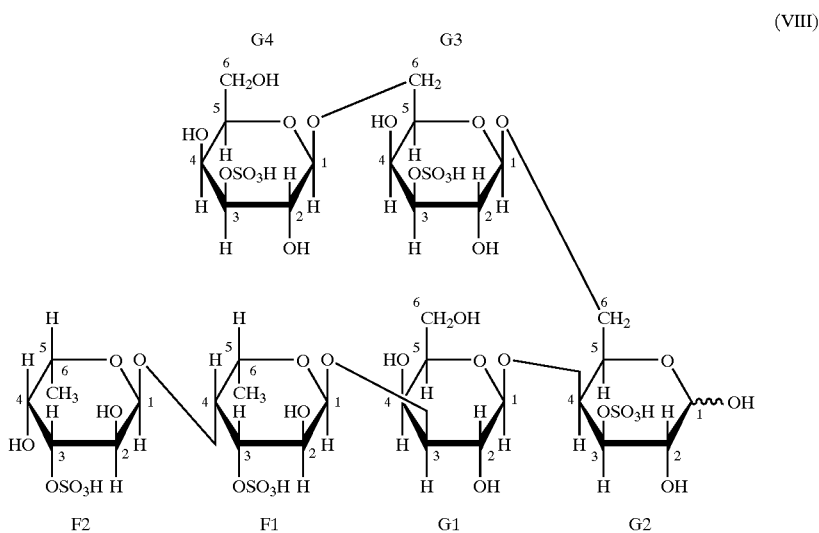

(5) Physical Properties of Smaller Molecule (E)

Figure 15:
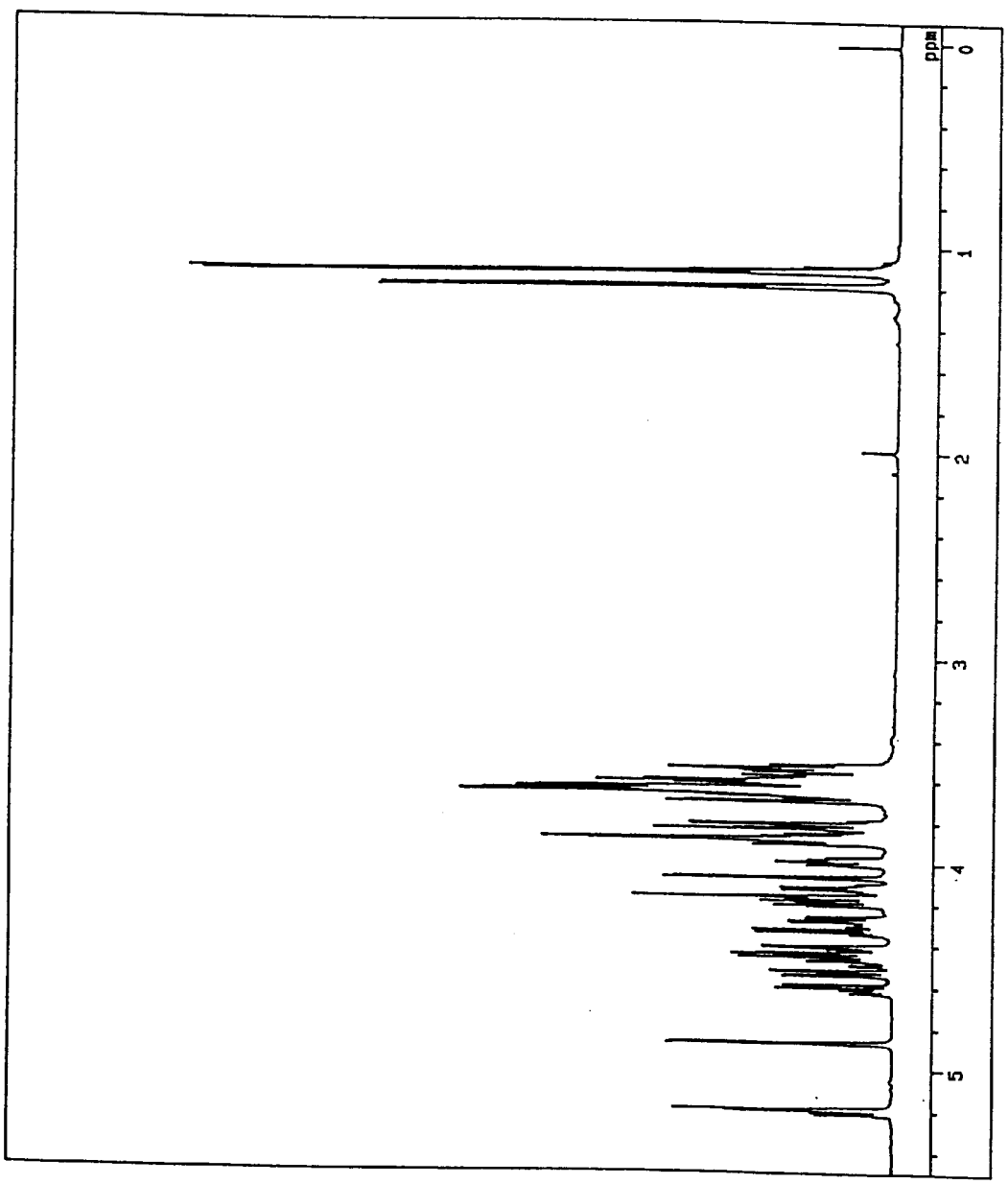
FIG. 15: a figure which illustrates the $^1$H-NMR spectrum of the smaller molecule (E) from the sulfated fucogalactan according to the present invention.
Figure 16:
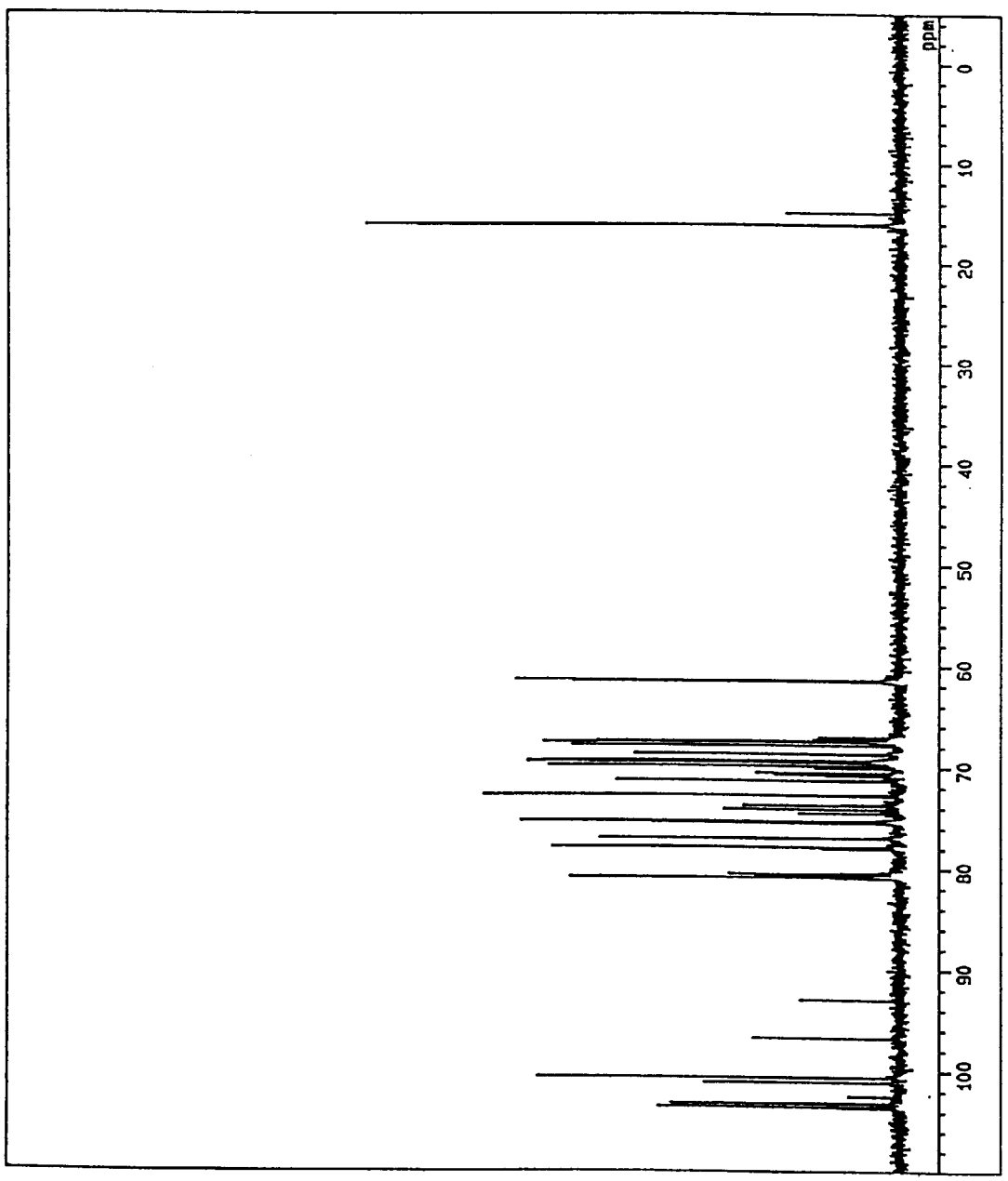
FIG. 16: a figure which illustrates the $^{13}$C -NMR spectrum of the smaller molecule (E) from the sulfated fucogalactan according to the present invention.
Figure 17:
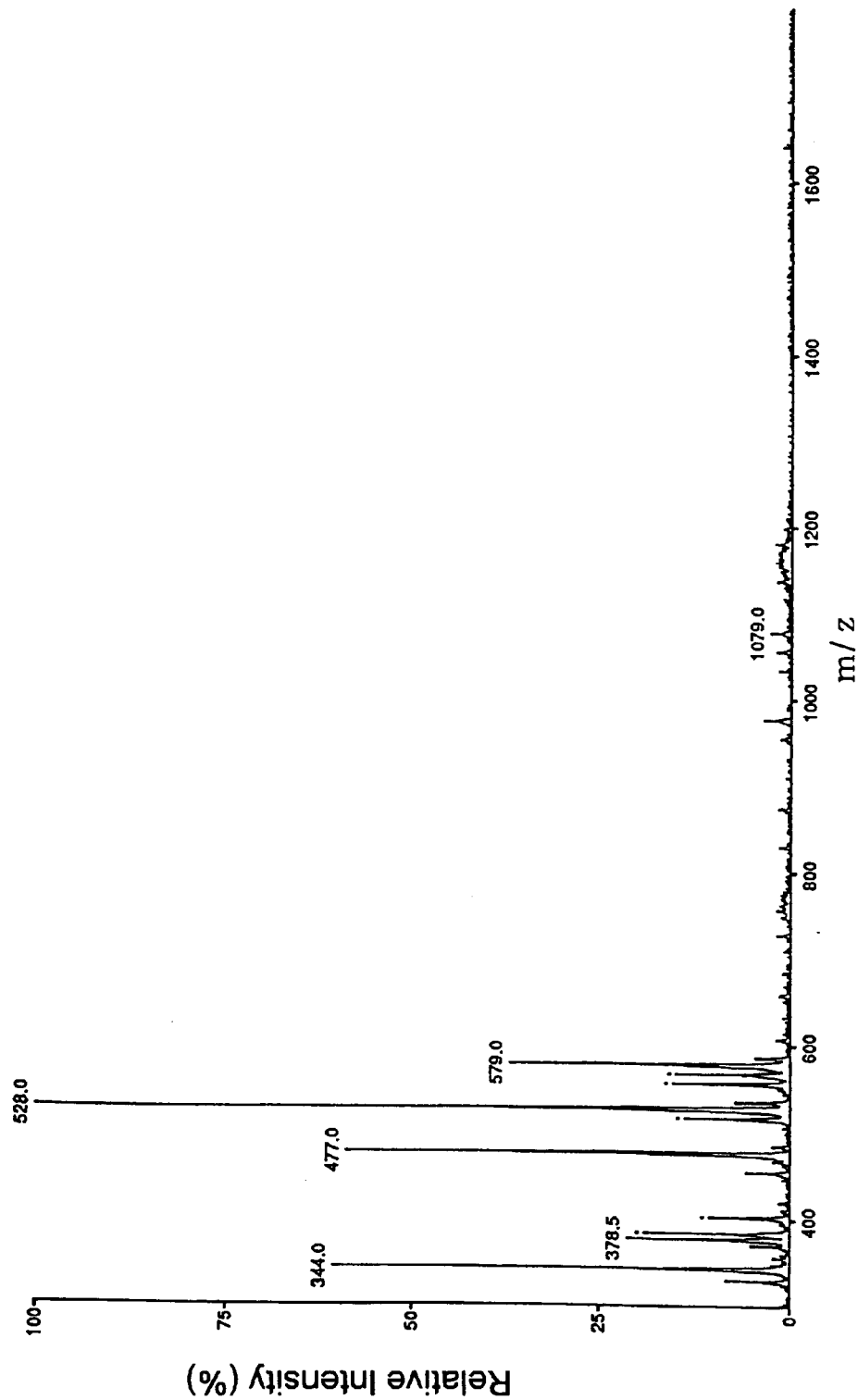
FIG. 17: a figure which illustrates the mass spectrum of the smaller molecule (E) from the sulfated fucogalactan according to the present invention.

The results for mass spectrometric analysis and identification in NMR are shown below. The ¹H-NMR spectrum, ¹³C-NMR spectrum and mass spectrum of the smaller molecule (E) from the sulfated fucogalactan of the present invention are illustrated in FIGS. 15, 16 and 17, respectively. FIG. 15 is a figure which illustrates the ¹H-NMR spectrum of the smaller molecule (E) from the sulfated fucogalactan of the present invention. FIG. 16 is a figure which illustrates the ¹³C-NMR spectrum of the smaller molecule (E) from the sulfated fucogalactan of the present invention. FIG. 17 is a figure which illustrates the mass spectrum of the smaller molecule (E) from the sulfated fucogalactan of the present invention. In FIGS. 15 and 16, the vertical axes represent the signal intensity and the horizontal axes represent the chemical shift value (ppm). In FIG. 17, the vertical axis represents the relative intensity (%) and the horizontal axis represents the m/z value.

Molecular weight: 1036; MS m/z 528.0[M+Na$^+$–3H$^+$]$^{2-}$, 344.0[M–3H$^+$]$^{3-}$; ¹H-NMR(D$_2$O); δ; 5.19 (1H, d, J=4.3 Hz, F1-1-H), 4.87 (1H, d, J=3.7 Hz, F2-1-H), 4.63 (1H, overlapped with HOD, G1-1-H), 4.59 (1H, d, J=7.9 Hz, G2-1-H), 4.53 (1H, d-d, J=10.7, 1.8 Hz, F1-3-H), 4.44 (1H, d, J=7.6 Hz, G3-1-H), 4.40 (1H, br-s, G2-4-H), 4.32 (1H, q, J=6.4 Hz, F2-5-H), 4.27 (1H, m, G2-3-H), 4.19 (1H, m, G3-3-H), 4.16 (1H, br-s, G3-4-H), 4.12 (1H, q, J=6.4 Hz, F1-5-H), 4.06 (1H, d, J=1.8 Hz, F1-4-H), 3.99 (1H, m, G2-6-H), 3.88 (1H, br-s, G1-4-H), 3.88 (1H, d-d, J=10.7, 4.3 Hz, F1-2-H), 3.86 (1H, m, G2-5-H), 3.81 (1H, m, G2-6-H), 3.81 (1H, m, F2-3-H), 3.69 (1H, d, J=1.8 Hz, F2-4-H), 3.66 (1H, m, G1-3-H), 3.65 (1H, m, G2-2-H), 3.64 (1H, m, F2-2-H), 3.63 (2H, m, G1-6-H), 3.61 (1H, m, G3-5-H), 3.61 (2H, m, G3-6-H), 3.60 (1H, m, G1-2-H), 3.53 (1H, m, G1-5-H), 3.53 (1H, m, G3-2-H), 1.19 (3H, d, J=6.4, F1-6-H), 1.12 (3H, d, J=6.4, F2-6-H); ¹³C-NMR(D$_2$O).

Chemical shift values for the respective carbons in ¹³C-NMR analysis are shown in Table 6.

TABLE 6

| Carbon position | ¹³C-NMR chemical shift value (ppm) |
| --- | --- |
| G1-1 | 103.2 |
| G1-2 | 71.2 |
| G1-3 | 80.3 |
| G1-4 | 69.3 |
| G1-5 | 75.4 |
| G1-6 | 61.3 |
| G2-1 | 96.7 |
| G2-2 | 70.4 |
| G2-3 | 80.8 |
| G2-4 | 73.7 |
| G2-5 | 74.0 |
| G2-6 | 70.6 |
| G3-1 | 103.5 |
| G3-2 | 69.4 |
| G3-3 | 80.8 |
| G3-4 | 67.4 |
| G3-5 | 75.2 |
| G3-6 | 61.5 |
| F1-1 | 101.1 |
| F1-2 | 67.3 |
| F1-3 | 76.9 |
| F1-4 | 77.8 |
| F1-5 | 68.5 |
| F1-6 | 16.1 |
| F2-1 | 100.6 |
| F2-2 | 69.2 |
| F2-3 | 69.8 |
| F2-4 | 72.7 |
| F2-5 | 67.7 |
| F2-6 | 16.0 |

Saccharide composition: L-fucose: D-galactose=2:3
Sulfate group: 3 molecules

The numbers for peak identification in $^1$H-NMR are as indicated in formula (IX) below.

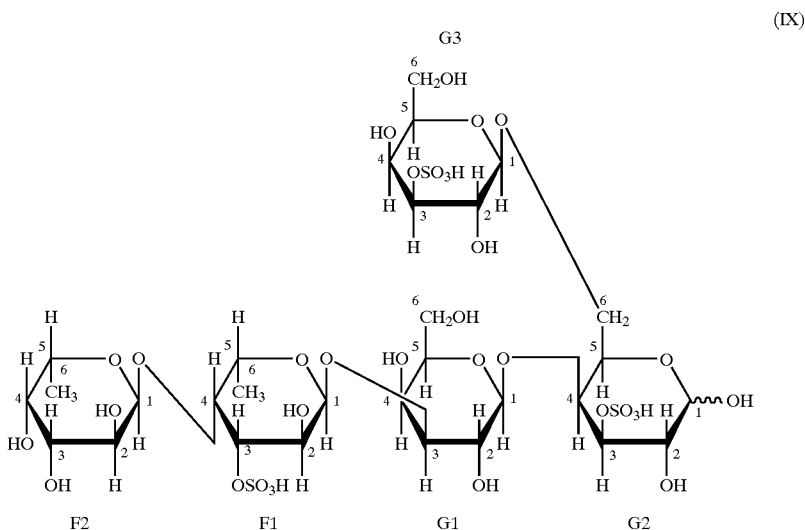

(IX)

(6) Physical Properties of Smaller Molecule (F)

Figure 18:
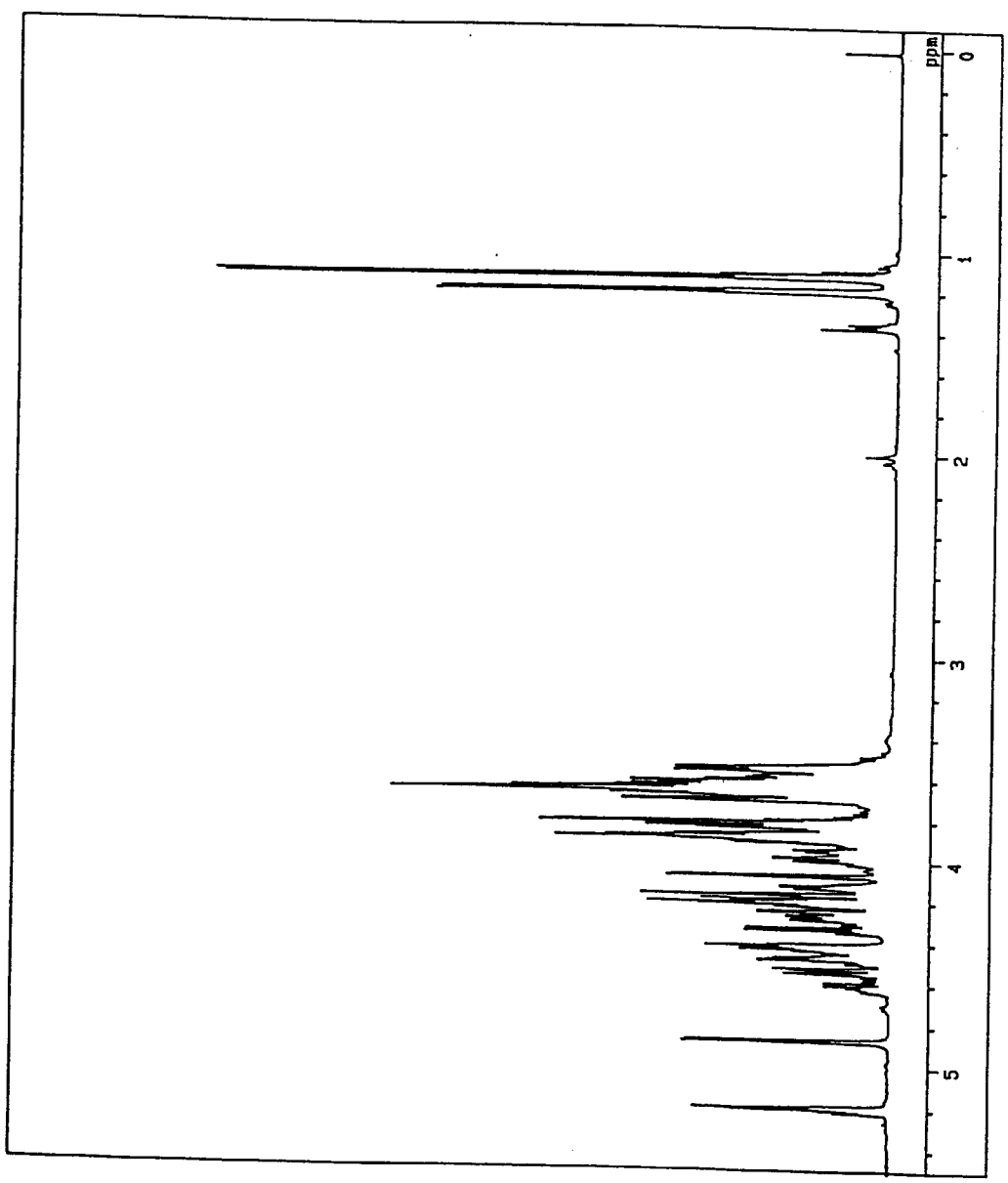
FIG. 18: a figure which illustrates the $^1$H-NMR spectrum of the smaller molecule (F) from the sulfated fucogalactan according to the present invention.
Figure 19:
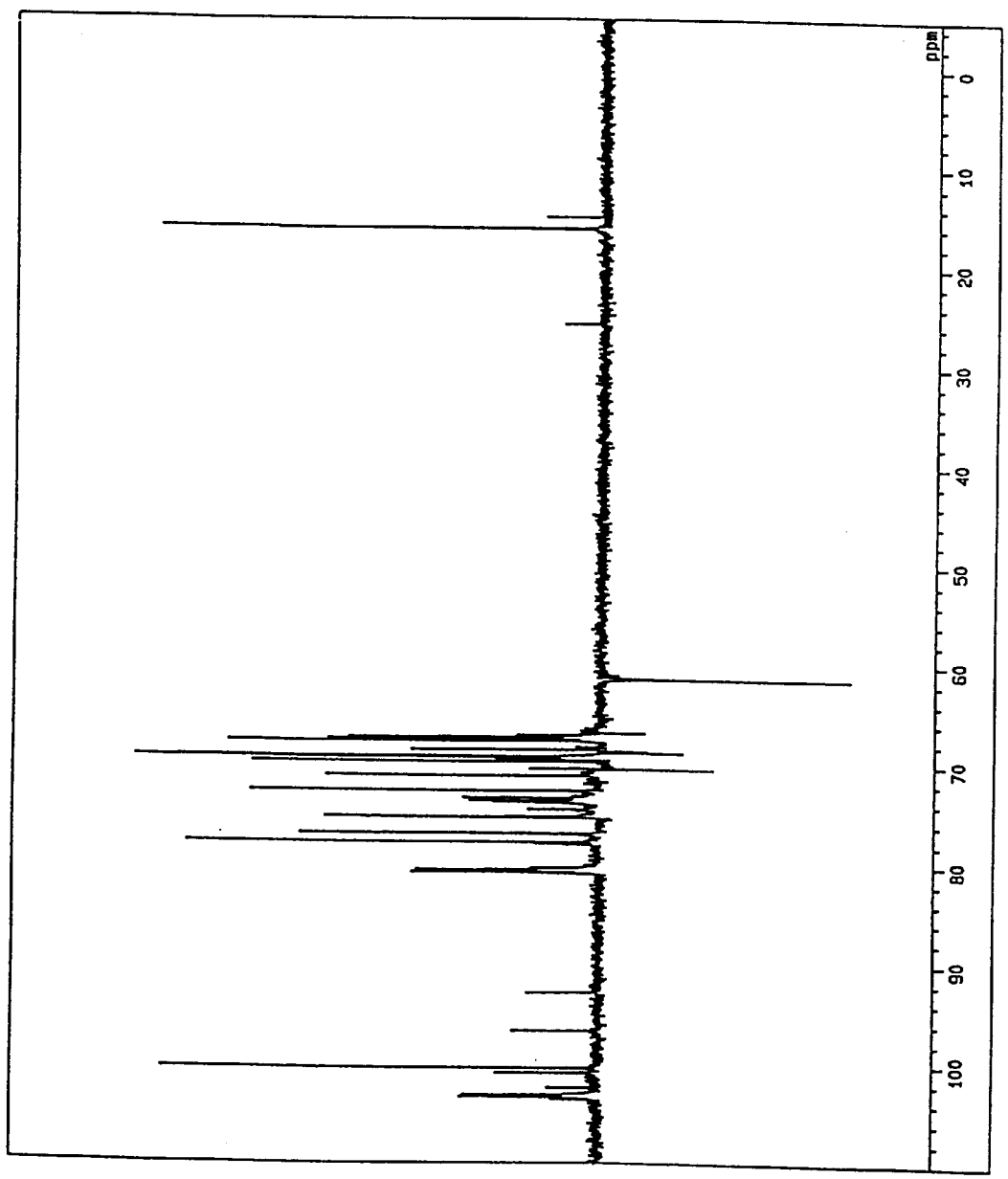
FIG. 19: a figure which illustrates the $^{13}$C-DEPT-135° spectrum of the smaller molecule (F) from the sulfated fucogalactan according to the present invention.
Figure 20:
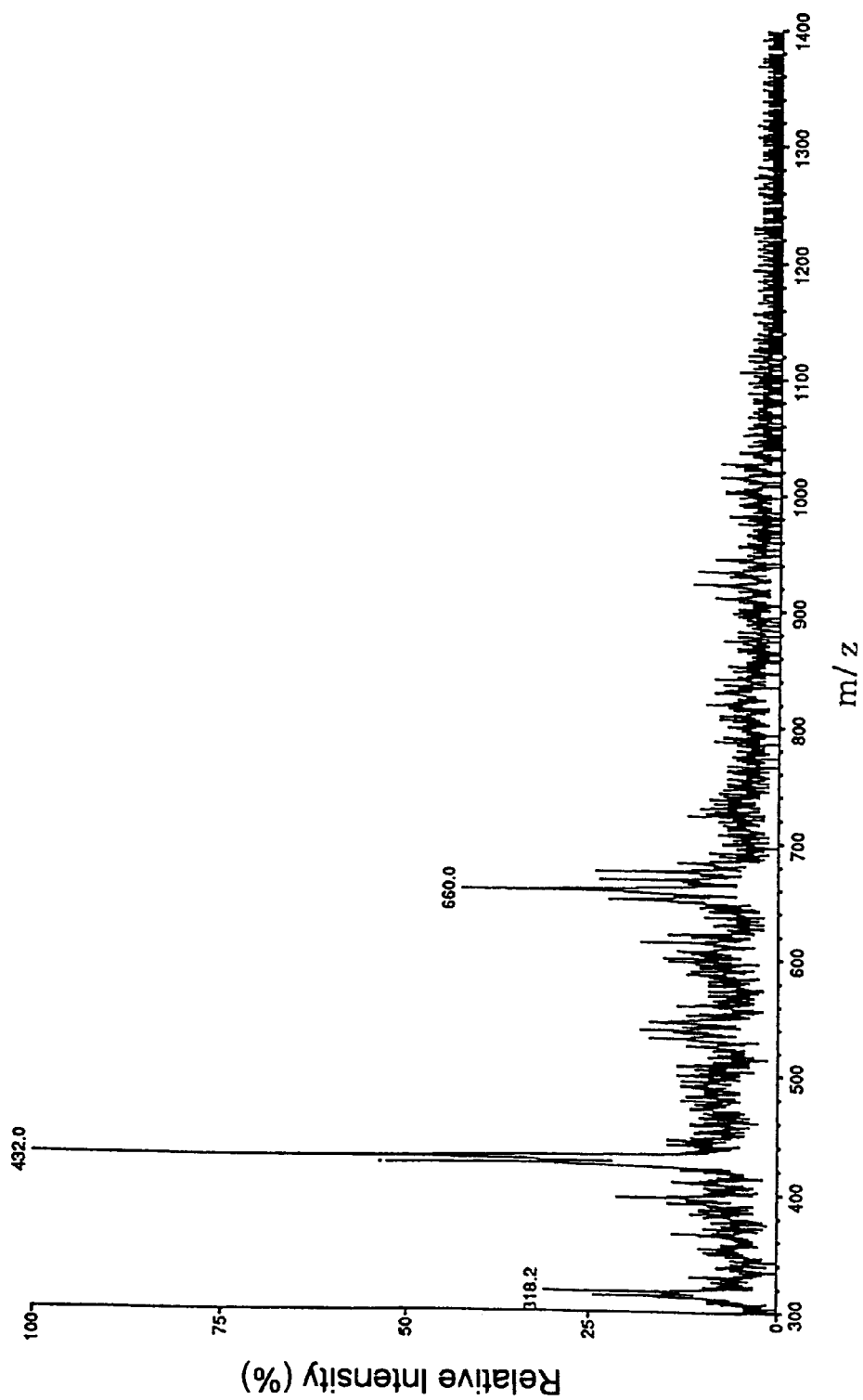
FIG. 20: a figure which illustrates the mass spectrum of the smaller molecule (F) from the sulfated fucogalactan according to the present invention.

The results for mass spectrometric analysis and identification in NMR are shown below. The $^1$H-NMR spectrum, $^{13}$C-DEPT-135° spectrum and mass spectrum of the smaller molecule (F) from the sulfated fucogalactan of the present invention are illustrated in FIGS. 18, 19 and 20, respectively. FIG. 18 is a figure which illustrates the $^1$H-NMR spectrum of the smaller molecule (F) from the sulfated fucogalactan of the present invention. FIG. 19 is a figure which illustrates the $^{13}$C-DEPT-135° spectrum of the smaller molecule (F) from the sulfated fucogalactan of the present invention. FIG. 20 is a figure which illustrates the mass spectrum of the smaller molecule (F) from the sulfated fucogalactan of the present invention. In FIGS. 18 and 19, the vertical axes represent the signal intensity and the horizontal axes represent the chemical shift value (ppm). In FIG. 20, the vertical axis represents the relative intensity (%) and the horizontal axis represents the m/z value.

Molecular weight: 1278; MS m/z 660.0 $[M+2Na^+-4H^+]^{2-}$, 432.0 $[M+Na^+-4H^+]^{3-}$, 318.2 $[M-4H^+]^{4-}$; $^1$H-NMR(D$_2$O); δ; 5.19 (1H, d, J=4.3 Hz, F1-1-H), 4.87 (1H, d, J=3.8 Hz, F2-1-H), 4.61 (1H, overlapped with HOD, G1-1-H), 4.59 (1H, J=7.9 Hz, G2-1-H), 4.53 (1H, d-d, J=10.6, 2.7 Hz, F1-3-H), 4.46 (1H, d, J=7.6 Hz, G3-1-H), 4.42 (1H, d, J=7.6 Hz, G4-1-H), 4.41 (1H, br-s, G2-4-H), 4.32 (1H, q, J=6.4 Hz, F2-5-H), 4.27 (1H, m, G2-3-H), 4.24 (1H, br-s, G3-4-H), 4.20 (1H, m, G3-3-H), 4.20 (1H, m, G4-3-H), 4.16 (1H, br-s, G4-4-H), 4.12 (1H, q, J=6.7 Hz, F1-5-H), 4.06 (1H, d, J=2.7 Hz, F1-4-H), 3.98 (1H, m, G2-6-H), 3.94 (1H, m, G3-6-H), 3.89 (1H, d-d, J=10.6, 4.3 Hz, F1-2-H), 3.88 (1H, br-s, G1-4-H), 3.86 (1H, m, G2-5-H), 3.86 (1H, m, G2-6-H), 3.82 (1H, m, F2-3-H), 3.80 (1H, m, G3-5-H), 3.80 (1H, m, G3-6-H), 3.69 (1H, d, J=2.8, F2-4-H), 3.66 (1H, m, G1-3-H), 3.65 (2H, m, G1-6-H), 3.65 (2H, m, G4-6-H), 3.64 (1H, m, G2-2-H), 3.64 (1H, m, F2-2-H), 3.62 (1H, m, G4-5-H), 3.59 (1H, m, G1-2-H), 3.54 (1H, m, G1-5-H), 3.54 (1H, m, G3-2-H), 3.54 (1H, m, G4-2-H), 1.19 (3H, d, J=6.7, F1-6-H), 1.12 (3H, d, J=6.4, F2-6-H); $^{13}$C-NMR(D$_2$O).

Chemical shift values for the respective carbons in $^{13}$C-NMR analysis are shown in Tables 7 and 8.

TABLE 7

| Carbon position | $^{13}$C-NMR chemical shift value (ppm) |
|---|---|
| G1-1 | 103.2 |
| G1-2 | 71.2 |
| G1-3 | 80.4 |
| G1-4 | 69.3 |
| G1-5 | 75.3 |
| G1-6 | 61.3 |
| G2-1 | 96.7 |
| G2-2 | 70.4 |
| G2-3 | 80.5 |
| G2-4 | 73.7 |
| G2-5 | 73.8 |
| G2-6 | 70.5 |
| G3-1 | 103.5 |
| G3-2 | 69.2 |
| G3-3 | 80.5 |
| G3-4 | 67.2 |
| G3-5 | 73.4 |
| G3-6 | 68.8 |
| G4-1 | 103.4 |
| G4-2 | 69.2 |
| G4-3 | 80.8 |
| G4-4 | 67.4 |
| G4-5 | 75.3 |
| G4-6 | 61.3 |

TABLE 8

(continued from Table 7)

| Carbon position | $^{13}$C-NMR chemical shift value (ppm) |
|---|---|
| F1-1 | 101.0 |
| F1-2 | 67.3 |
| F1-3 | 76.9 |
| F1-4 | 77.7 |
| F1-5 | 68.5 |
| F1-6 | 16.0 |
| F2-1 | 100.5 |
| F2-2 | 69.1 |
| F2-3 | 69.7 |
| F2-4 | 72.7 |

TABLE 8-continued (continued from Table 7)

| Carbon position | $^{13}$C-NMR chemical shift value (ppm) |
|---|---|
| F2-5 | 67.7 |
| F2-6 | 15.9 |

Saccharide composition: L-fucose: D-galactose 2:4
Sulfate group: 4 molecules

The numbers for peak identification in $^1$H-NMR are as indicated in formula (X) below.

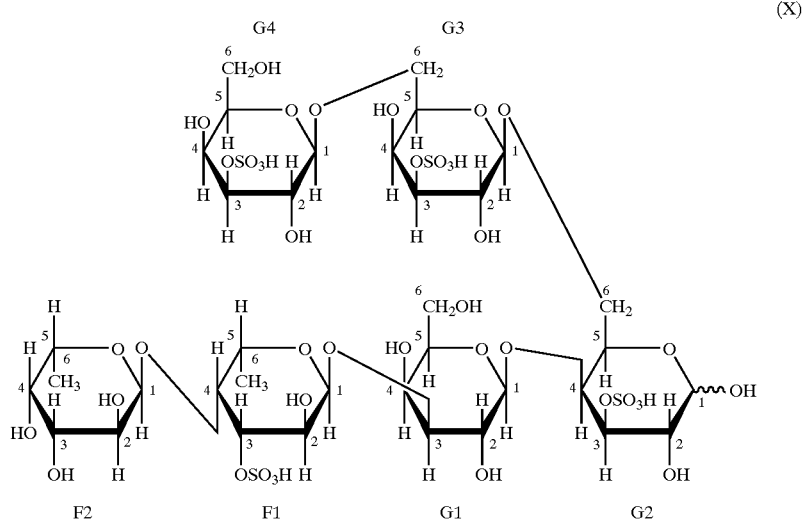

(X)

Example 8

(1) Analysis of the Main Structure of the Sulfated Fucogalactan of the Present Invention NMR analysis was carried out in order to determine the entire structure of the sulfated fucogalactan fraction as prepared in Example 1(2) and the cleavage site by the sulfated fucogalactan-digesting enzyme.

Figure 21:
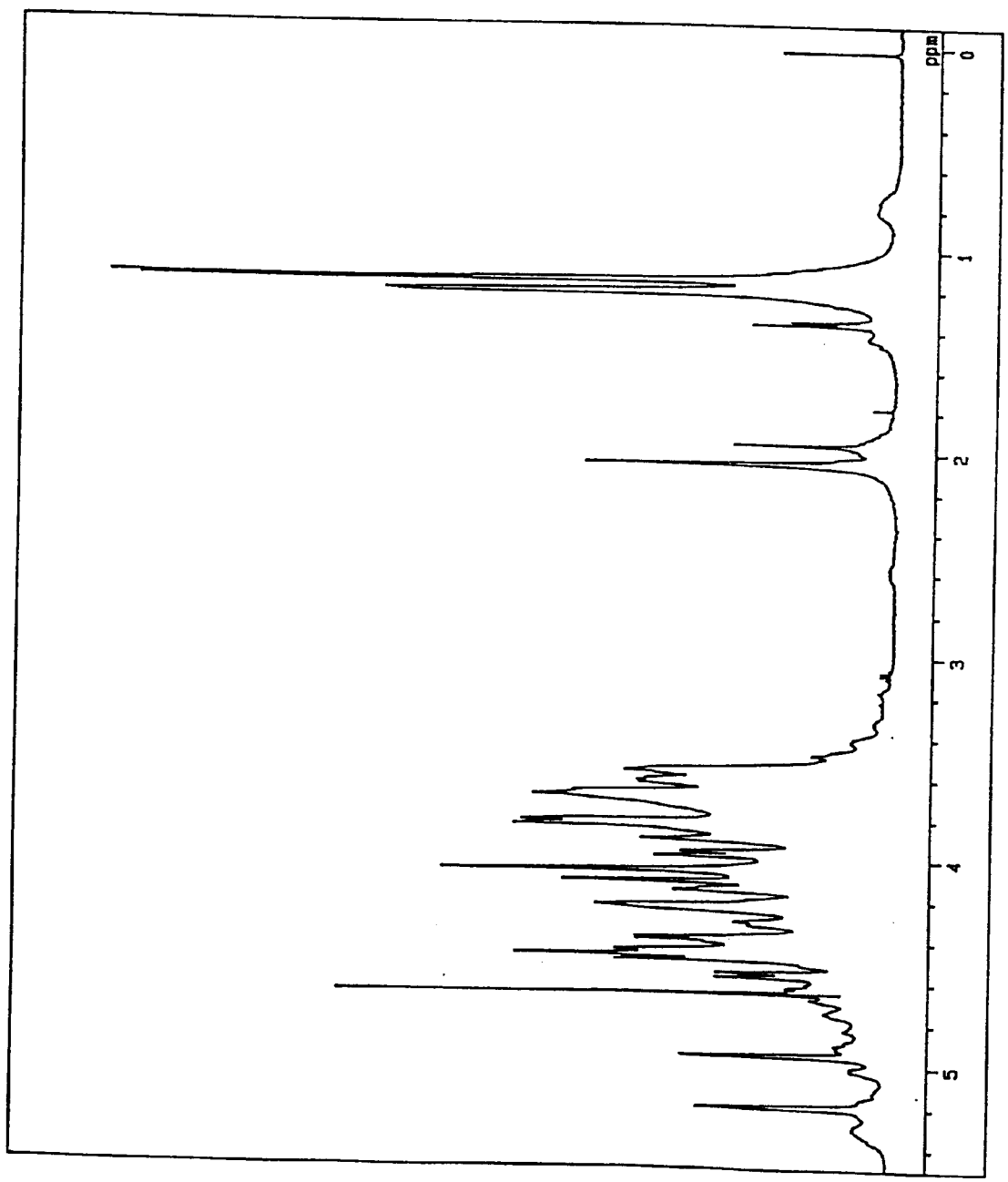
FIG. 21: a figure which illustrates the $^1$H-NMR spectrum of the sulfated fucogalactan according to the present invention.
Figure 22:
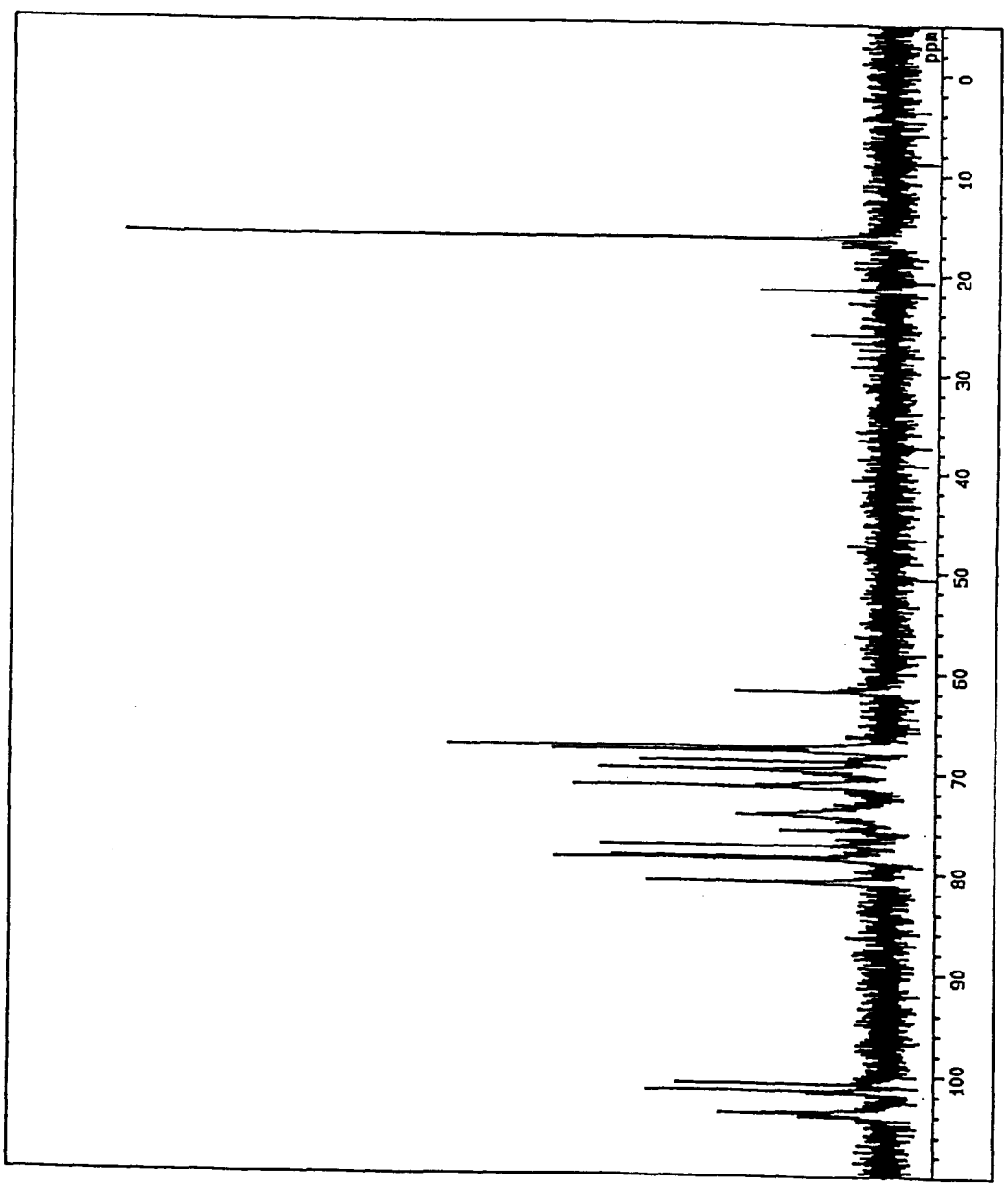
FIG. 22: a figure which illustrates the $^{13}$C-NMR spectrum of the sulfated fucogalactan according to the present invention.
Figure 23:
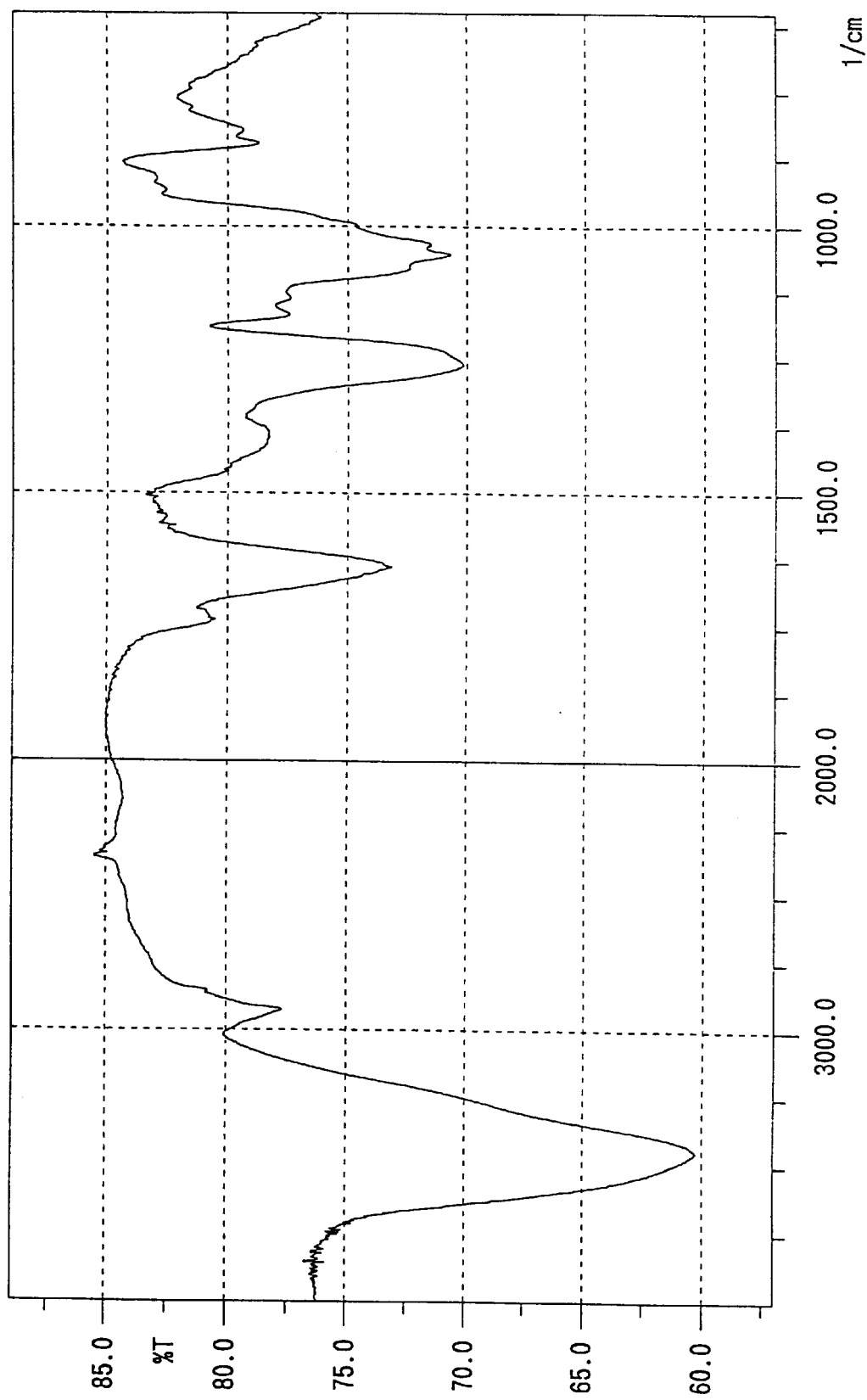
FIG. 23: a figure which illustrates the infrared absorption spectrum of the sulfated fucogalactan according to the present invention.

Identification in NMR is shown below. The $^1$H-NMR spectrum, $^{13}$C-NMR spectrum and infrared absorption (IR) spectrum of the sulfated fucogalactan of the present invention are illustrated in FIGS. 21, 22 and 23, respectively. FIG. 21 is a figure which illustrates the $^1$H-NMR spectrum of the sulfated fucogalactan of the present invention. FIG. 22 is a figure which illustrates the $^{13}$C-NMR spectrum of the sulfated fucogalactan of the present invention. FIG. 23 is a figure which illustrates the infrared absorption spectrum of the sulfated fucogalactan of the present invention. In FIGS. 21 and 22, the vertical axes represent the signal intensity and the horizontal axes represent the chemical shift value (ppm). In FIG. 23, the vertical axis represents the transmissivity (%) and the horizontal axis represents the wave number (cm$^{-1}$). Results for the $^1$H-NMR analysis and the $^{13}$C-NMR analysis are shown in Tables 9 and 10.

TABLE 9

| Carbon position | Chemical shift value (ppm) | |
|---|---|---|
| | $^{13}$C-NMR | $^1$H-NMR |
| G1-1 | 103.4 | 4.63 |
| G1-2 | 71.3 | 3.61 |
| G1-3 | 80.8 | 3.67 |
| G1-4 | 69.6 | 3.89 |
| G1-5 | 75.6 | 3.57 |
| G1-6 | 61.7 | 3.62, 3.68 |
| G2-1 | 103.7 | 4.45 |

TABLE 9-continued

| Carbon position | Chemical shift value (ppm) | |
|---|---|---|
| | $^{13}$C-NMR | $^1$H-NMR |
| G2-2 | 69.6 | 3.56 |
| G2-3 | 80.8 | 4.32 |
| G2-4 | 74.1 | 4.44 |
| G2-5 | 74.1 | 3.87 |
| G2-6 | 71.3 | 3.83, 3.97 |
| G3-1 | 103.7 | 4.45 |
| G3-2 | 69.6 | 3.56 |
| G3-3 | 80.8 | 4.23 |
| G3-4 | 67.4 | 4.24 |
| G3-5 | 74.1 | 3.82 |
| G3-6 | 69.6 | 3.85, 3.99 |
| G4-1 | 103.7 | 4.45 |
| G4-2 | 69.6 | 3.56 |
| G4-3 | 80.8 | 4.23 |
| G4-4 | 67.4 | 4.17 |
| G4-5 | 74.1 | 3.82 |

TABLE 10

(continued from Table 9)

| Carbon position | Chemical shift value (ppm) | |
|---|---|---|
| | $^{13}$C-NMR | $^1$H-NMR |
| G4-6 | 68.8 | 4.07, 4.17 |
| F1-1 | 101.5 | 5.20 |

TABLE 10-continued (continued from Table 9)

| Carbon position | Chemical shift value (ppm) | |
|---|---|---|
| | $^{13}$C-NMR | $^{1}$H-NMR |
| F1-2 | 67.4 | 3.97 |
| F1-3 | 77.1 | 4.58 |
| F1-4 | 78.5 | 4.11 |
| F1-5 | 68.8 | 4.14 |
| F1-6 | 16.3 | 1.21 |
| F2-1 | 100.8 | 4.95 |
| F2-2 | 67.4 | 3.82 |
| F2-3 | 78.5 | 4.50 |
| F2-4 | 71.3 | 4.05 |
| F2-5 | 67.8 | 4.39 |
| F2-6 | 16.2 | 1.15 |

Based on the identification as shown in Tables 9 and 10, it was demonstrated that the main backbone of the sulfated fucogalactan of the present invention is the compound (D) in Example 7(4), and that the sulfated fucogalactan of the present invention has a structure in which the compounds are repeatedly bonded. The bond between the repeated structure was a β-bond of the galactose G2 to the position 6 of the galactose G4 as shown in formula (XIII) below. Thus, it was demonstrated that the sulfated fucogalactan has a repeated structure of the main backbones as shown below.

(2) Activity of Inducing HGF Production of the Sulfated Fucogalactan of the Present Invention The activity of inducing HGF production of the sulfated fucogalactan of the present invention obtained as described in Example 1(2) was determined. The activity of inducing HGF production was measured as follows. Briefly, 500 μl of a suspension containing MRC-5 cells (CCL171; Dainippon Pharmaceutical, code. 02-021) in DME medium containing 10% fetal calf serum at a concentration of $1 \times 10^5$ cells/ml was placed in each well of a 48-well cell culture plate and the plate was incubated at 37° C. for 24 hours in the presence of 5% $CO_2$. The medium was then replaced by DME medium containing 1% fetal calf serum. The sulfated fucogalactan obtained as described in Example 1(2) as a sample was added to the well at a final concentration of 1, 10 or 100 μg/ml. The plate was further incubated for 24 hours. The amount of HGF in the collected medium was then measured using Quantikine Human Hepatocyte Growth Factor (HGF) ELISA Kit (Funakoshi, Code. RS-0641-00). Distilled water in an amount equal to that of the sample was added for a control. The amount of HGF for the control, 4.3 ng/ml, was defined as 100%. The amounts of HGF produced for the groups to which the samples were added are shown in Table 11. All of the experiments were carried out in duplicate. The mean values are shown.

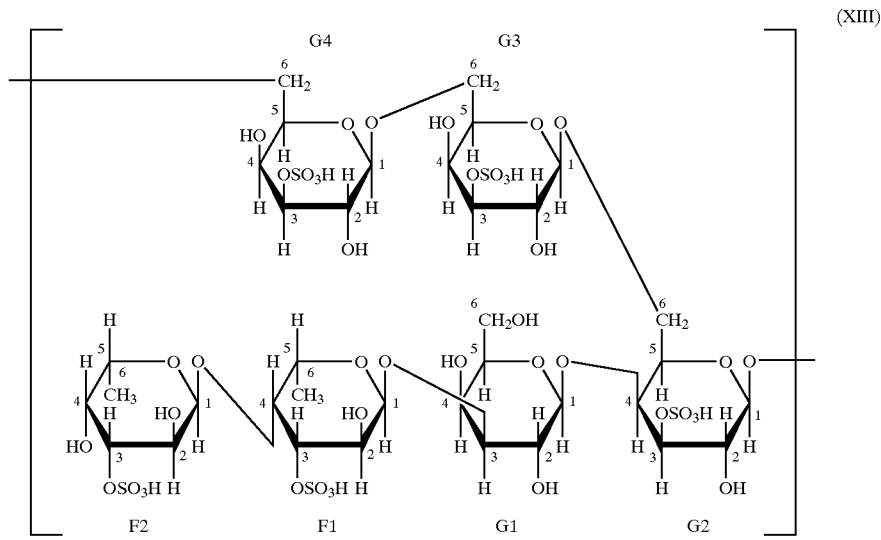

(XIII)

Furthermore, based on the chemical structures of the sulfated fucogalactan of the present invention and the smaller molecules from the sulfated fucogalactan of the present invention, it was demonstrated that the sulfated fucogalactan-digesting enzyme of the present invention is an enzyme that digests the β 1–6 bond and β 1–4 bond between sulfated D-galactose or galactose and sulfated D-galactose or galactose in the sulfated fucogalactan endowisely. Furthermore, the mean molecular weight of the sulfated fucogalactan of the present invention was about 130,000 with molecular weight distribution from about 10,000 to about 200,000 as measured under conditions as described in Example 1(3).

TABLE 11

| Concentration (μg/ml) | Increase in HGF production (%) |
|---|---|
| 1 | 194 |
| 10 | 355 |
| 100 | 429 |

The amount of HGF produced for the control was 4.3 ng/ml.

As shown in Table 11, it was confirmed that the sulfated fucogalactan of the present invention induces the production of HGF, and thus the sulfated fucogalactan of the present invention is useful as an inducer of HGF production.

Example 9

(1) 70 g of the sulfated-fucose-containing polysaccharide fraction from Kjellmaniella crassifolia obtained in Example 3 was dissolved in 20 mM imidazole-hydrochloride buffer (pH 7.5) containing 300 mM sodium chloride and 10% ethanol and subjected to ultrafiltration using an ultrafiltration device equipped with hollow fibers with exclusion molecular weight of 100,000 to thoroughly remove any substances which could be filtrated. The same buffer as that used above for the dissolution was used for the ultrafiltration.

20 U of the sulfated-fucose-containing polysaccharide-U-digesting enzyme obtained from a culture of Flavobacterium sp. SA-0082 (FERM BP-5402) as described in WO97/26896 was added to the solution retained after the ultrafiltration. The mixture was reacted at 25° C. for 5 days. The reaction mixture was subjected to ultrafiltration using an ultrafiltration device equipped with hollow fibers with exclusion molecular weight of 100,000 to thoroughly remove substances which were converted into smaller molecules by the sulfated-fucose-containing polysaccharide-U-digesting enzyme, i.e., smaller molecules from the sulfated fucoglucuronomannan. Water was used for the ultrafiltration, which was finally exchanged for 10 mM imidazole-hydrochloride buffer (pH 8) containing 200 mM sodium chloride.

2 U of the sulfated fucogalactan-digesting enzyme as described in Example 2(1) was added to the solution retained after the ultrafiltration. The mixture was reacted at 25° C. for 5 days. The reaction mixture was subjected to ultrafiltration using an ultrafiltration device equipped with hollow fibers with exclusion molecular weight of 100,000 to thoroughly remove substances which were converted into smaller molecules by the sulfated fucogalactan-digesting enzyme, i.e., smaller molecules from the sulfated fucogalactan. The same buffer as that used for the reaction mixture was used for the ultrafiltration.

Calcium chloride at a final concentration of 20 mM and 5 U of the sulfated-fucose-containing polysaccharide-F-digesting enzyme obtained from a culture of Alteromonas sp. SN-1009 (FERM BP-5747) as described in WO97/26896 were added to the solution retained after the ultrafiltration. The mixture was reacted at 25° C. for 3 days. The reaction mixture was subjected to ultrafiltration using an ultrafiltration device equipped with hollow fibers with exclusion molecular weight of 100,000 to thoroughly remove substances which were converted into smaller molecules by the sulfated-fucose-containing polysaccharide-F-digesting enzyme. Water was used for the ultrafiltration. Physical and chemical properties of the smaller molecules from the fucose sulfate-containing polysaccharide contained in the thus obtained filtrate were examined.

(2) The filtrate obtained in (1) above was collected and subjected to ultrafiltration using an ultrafiltration device equipped with hollow fibers with exclusion molecular weight of 3000 to separate a filtrate from a non-filtrate.

The filtrate was concentrated to about 3 L using a rotary evaporator and centrifuged to obtain a supernatant. The supernatant was desalted using an electrodialysis device equipped with a membrane with exclusion molecular weight of 300. Calcium acetate was added to the desalted solution at a concentration of 0.1 M. The formed precipitate was removed by centrifugation. The resulting supernatant was loaded onto a DEAE-Cellulofine column (resin volume: 4 L) equilibrated with 50 mM calcium acetate. After extensive washing with 50 mM calcium acetate and 50 mM sodium chloride, elution was carried out with a gradient of 50 mM to 800 mM sodium chloride. 500 ml of the eluate was collected for each fraction. The collected fractions were analyzed according to the cellulose acetate membrane electrophoresis method [Analytical Biochemistry, 37:197–202 (1970)], and a fraction eluted with about 0.4 M sodium chloride (hereinafter referred to as a 0.4 M-eluted fraction) was found to be homogeneous. Additionally, a fraction eluted with about 0.6 M sodium chloride (hereinafter referred to as a 0.6 M-eluted fraction) was almost homogeneous as determined by electrophoresis.

The 0.4 M-eluted fraction was concentrated to 150 ml. Sodium chloride was added thereto at a concentration of 4 M. The resulting solution was loaded onto a Phenyl-Cellulofine column (resin volume: 200 ml) equilibrated with 4 M sodium chloride. After extensive washing with 4 M sodium chloride, fractions containing a non-adsorptive sulfated saccharide were collected and desalted using an electrodialysis device equipped with a membrane with exclusion molecular weight of 300 to obtain 505 ml of a desalted solution.

40 ml of the thus obtained desalted solution was loaded onto a Cellulofine GCL-90 column (4.1 cm×87 cm) equilibrated with 0.2 M sodium chloride containing 10% ethanol for gel filtration. 9.2 ml of the eluate was collected for each fraction.

The total sugar content was measured for each fraction according to the phenol-sulfuric acid method [Analytical Chemistry, 28:350 (1956)].

The sulfated saccharide formed one peak. A fraction in the middle portion of the peak was collected, desalted using an electrodialysis device equipped with a membrane with exclusion molecular weight of 300 and lyophilized to obtain 112 mg of a dried product of the sulfated saccharide of the present invention. A portion of the dried product was subjected to saccharide composition analysis and mass spectrometric analysis. In addition, 10 mg of the dried product was subjected to NMR analysis after exchange for heavy water according to a conventional method.

The results of the saccharide composition analysis demonstrated that the 0.4 M-eluted fraction contained a sulfated saccharide consisting of fucose.

Figure 24:
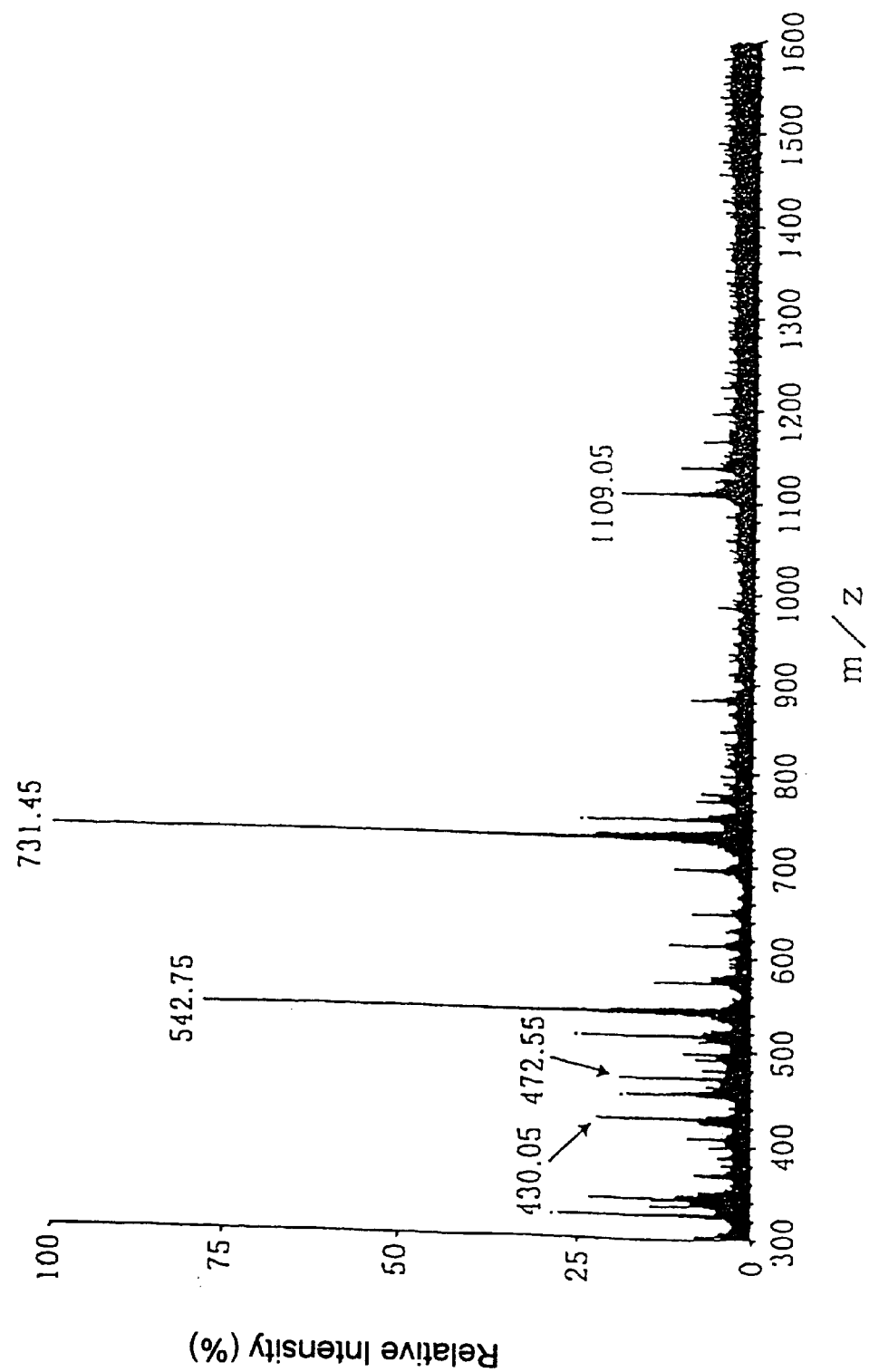
FIG. 24: a figure which illustrates the mass spectrum of the fraction of the smaller molecule from the fucose sulfate-containing polysaccharide eluted with 0.4 M sodium chloride.

Results of mass spectrometric analysis of the sulfated saccharide using API-III mass spectrometer (Perkin-Elmer Sciex) are shown in FIG. 24. The analytical results are shown below. FIG. 24 is a figure which shows results of the mass spectrometric analysis of the sulfated saccharide. The vertical axis represents the relative intensity (%) and the horizontal axis represents the m/z value. The molecular weight was determined to be 2264±1 provided that all of the sulfate groups formed sodium salts. The sulfated saccharide contains only fucose as its constituting saccharide. Thus, it was demonstrated that the sulfated saccharide is one in which 7 molecules of fucose and 12 molecules of sulfate group are bonded, and has a theoretical molecular weight of 2265 provided that all of the sulfate groups are forming sodium salts.

The main signals in FIG. 24 can be identified as follows defining the present substance as M.

| m/z | 1109.05 | — | $[M-2Na^+]^{2-}$ | (theoretical value: 1109.5) |
|---|---|---|---|---|
| | 731.45 | — | $[M-3Na^+]^{3-}$ | (theoretical value: 732) |
| | 542.75 | — | $[M-4Na^+]^{4-}$ | (theoretical value: 543.25) |
| | 430.05 | — | $[M-5Na^+]^{5-}$ | (theoretical value: 430) |

Thus, the present substance is an oligosaccharide consisting of 7 molecules of fucose and 12 molecules of sulfate group.

NMR analysis was then carried out using a nuclear magnetic resonance apparatus JNM-α500 (Nippon Denshi) in order to analyze the bond of fucose and determine the positions at which sulfate groups attach. Bonds of constituting saccharides were analyzed using the HMBC method, a method for $^1$H-detection of heteronuclear bond. The DQF-COSY method and the HOHAHA method were used for identification in $^1$H-NMR. The HSQC method was used for identification in $^{13}$C-NMR.

Figure 25:
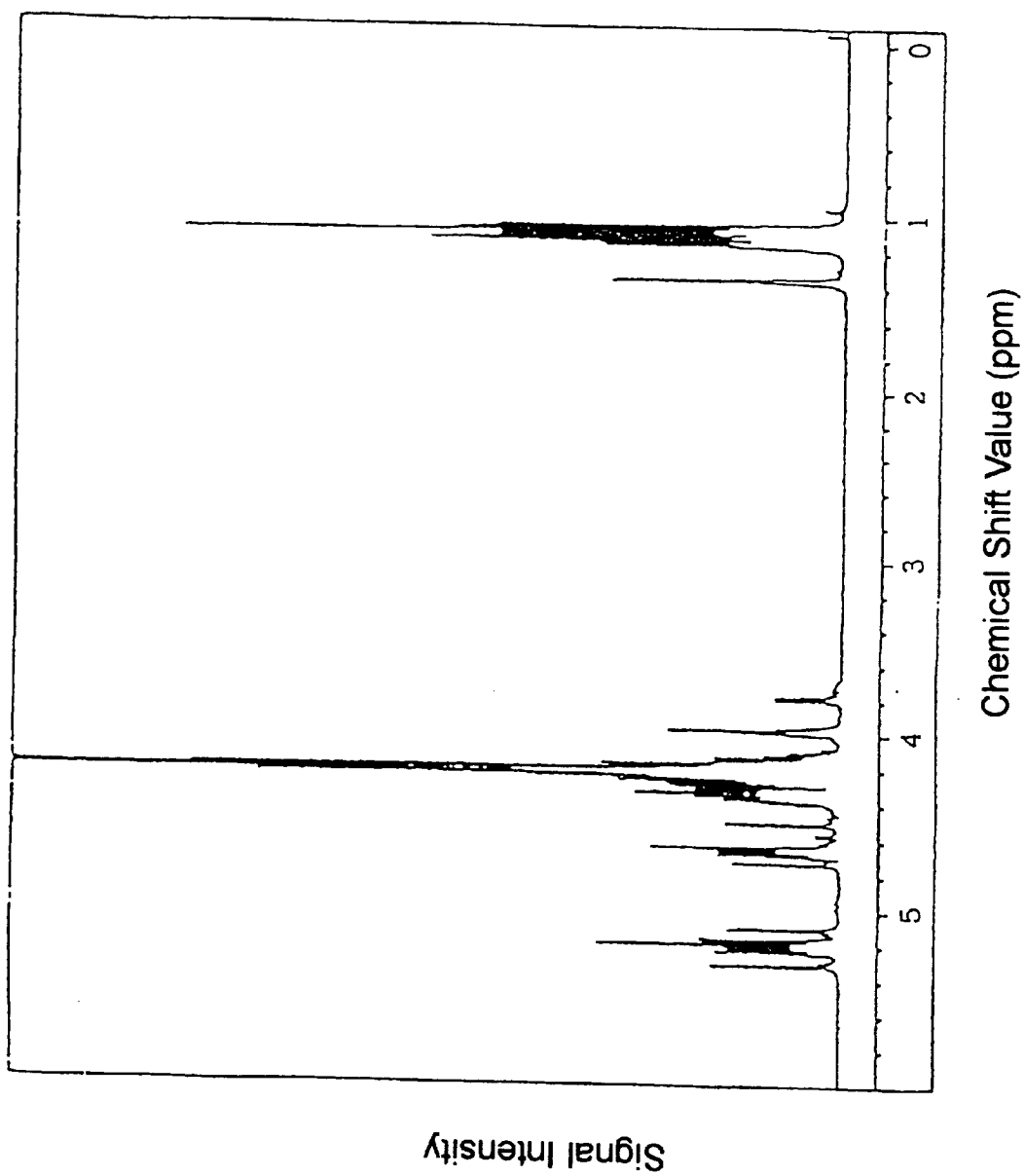
FIG. 25: a figure which illustrates the $^1$H-NMR spectrum of the fraction of the smaller molecule from the fucose sulfate-containing polysaccharide eluted with 0.4 M sodium chloride.
Figure 26:
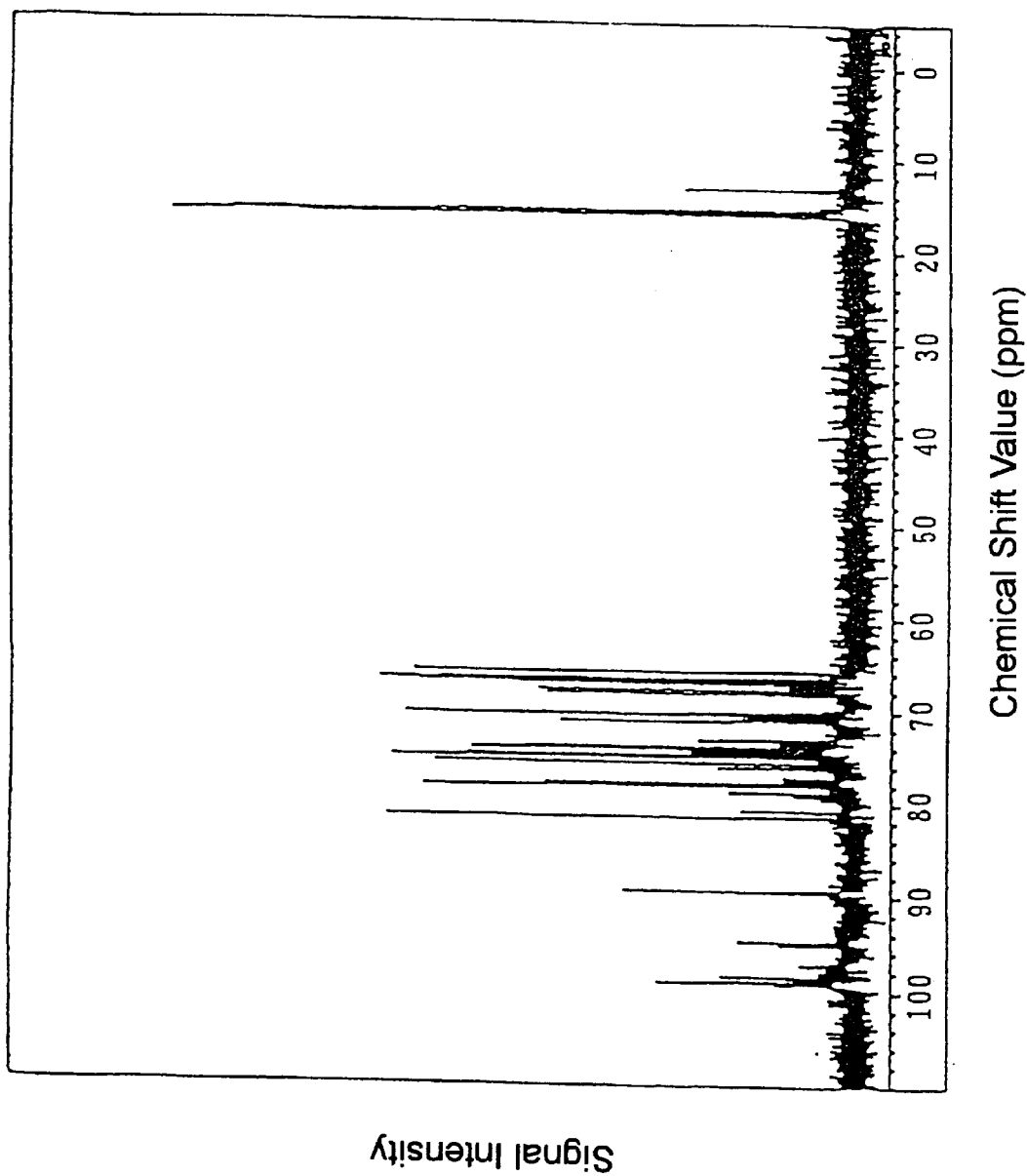
FIG. 26: a figure which illustrates the $^{13}$C-NMR spectrum of the fraction of the smaller molecule from the fucose sulfate-containing polysaccharide eluted with 0.4 M sodium chloride.

The results for identification in NMR are shown below. The $^1$H-NMR spectrum and $^{13}$C-NMR spectrum of the sulfated saccharide in the 0.4 M-eluted fraction are illustrated in FIGS. 25 and 26, respectively. The chemical shift values in $^1$H-NMR are expressed assuming the chemical shift value of dioxane as 3.53 ppm. The chemical shift values in $^{13}$C-NMR are expressed assuming the chemical shift value of dioxane as 66.5 ppm. Both of the measurements were carried out at 60° C. FIG. 25 is a figure which illustrates the $^1$H-NMR spectrum of the sulfated saccharide in the 0.4 M-eluted fraction. FIG. 26 is a figure which illustrates the $^{13}$C-NMR spectrum of the sulfated saccharide in the 0.4 M-eluted fraction. In FIGS. 25 and 26, the vertical axes represent the signal intensity and the horizontal axes represent the chemical shift value (ppm). Results for the $^1$H-NMR analysis and the $^{13}$C-NMR analysis are shown in Tables 12 and 13.

TABLE 12

| Carbon position | Chemical shift value (ppm) | |
|---|---|---|
| | $^{13}$C-NMR | $^1$H-NMR |
| A-1 | 89.3 | 5.30 |
| A-2 | 75.4 | 4.30 |
| A-3 | 73.9 | 4.17 |
| A-4 | 78.6 | 4.67 |
| A-5 | 67.5 | 4.14 |
| A-6 | 15.3 | 1.12 |
| B-1 | 98.3 | 5.23 |
| B-2 | 74.5 | 4.33 |
| B-3 | 75.9 | 4.18 |
| B-4 | 80.6 | 4.72 |
| B-5 | 68.0 | 4.10 |
| B-6 | 15.9 | 1.08 |
| C-1 | 98.9 | 5.18 |
| C-2 | 73.6 | 4.35 |
| C-3 | 70.9 | 4.32 |
| C-4 | 77.5 | 4.62 |
| C-5 | 66.9 | 4.24 |
| C-6 | 16.0 | 1.11 |

TABLE 12-continued

| Carbon position | Chemical shift value (ppm) | |
|---|---|---|
| | $^{13}$C-NMR | $^1$H-NMR |
| D-1 | 89.3 | 5.16 |
| D-2 | 73.9 | 3.98 |
| D-3 | 74.2 | 4.16 |
| D-4 | 73.0 | 4.64 |
| D-5 | 70.6 | 4.25 |
| D-6 | 13.1 | 1.34 |

TABLE 13

(continued from Table 12)

| Carbon position | Chemical shift value (ppm) | |
|---|---|---|
| | $^{13}$C-NMR | $^1$H-NMR |
| E-1 | 97.1 | 5.20 |
| E-2 | 73.0 | 4.37 |
| E-3 | 69.9 | 4.17 |
| E-4 | 77.4 | 4.65 |
| E-5 | 67.5 | 4.21 |
| E-6 | 15.8 | 1.15 |
| F-1 | 94.6 | 5.19 |
| F-2 | 74.8 | 4.27 |
| F-3 | 66.5 | 4.18 |
| F-4 | 81.3 | 4.49 |
| F-5 | 66.3 | 4.27 |
| F-6 | 15.8 | 1.06 |
| G-1 | 99.2 | 5.09 |
| G-2 | 65.6 | 3.78 |
| G-3 | 77.9 | 4.36 |
| G-4 | 70.1 | 3.97 |
| G-5 | 66.7 | 3.96 |
| G-6 | 15.4 | 1.04 |

The numbers for peak identification in NMR are as indicated in formula (XV) below.

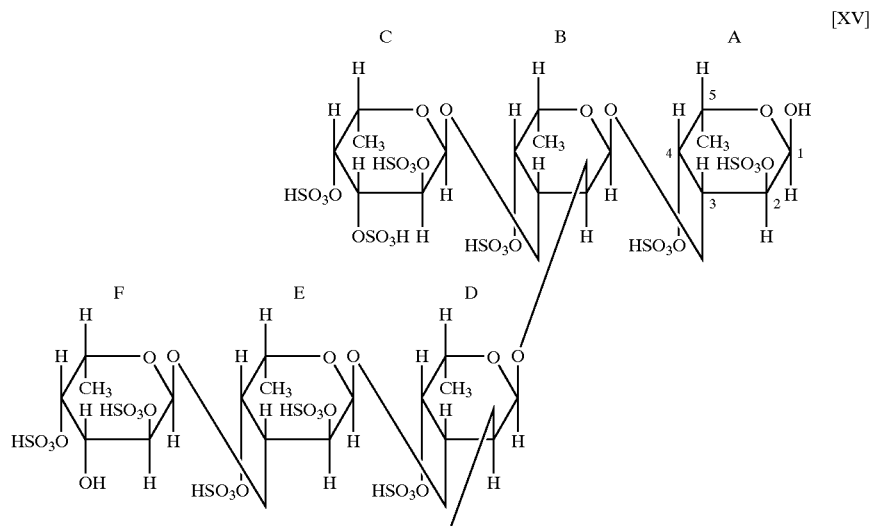

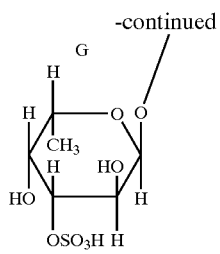

Based on these results, it was demonstrated that the present substance was a sulfated saccharide of formula (XVI) below.

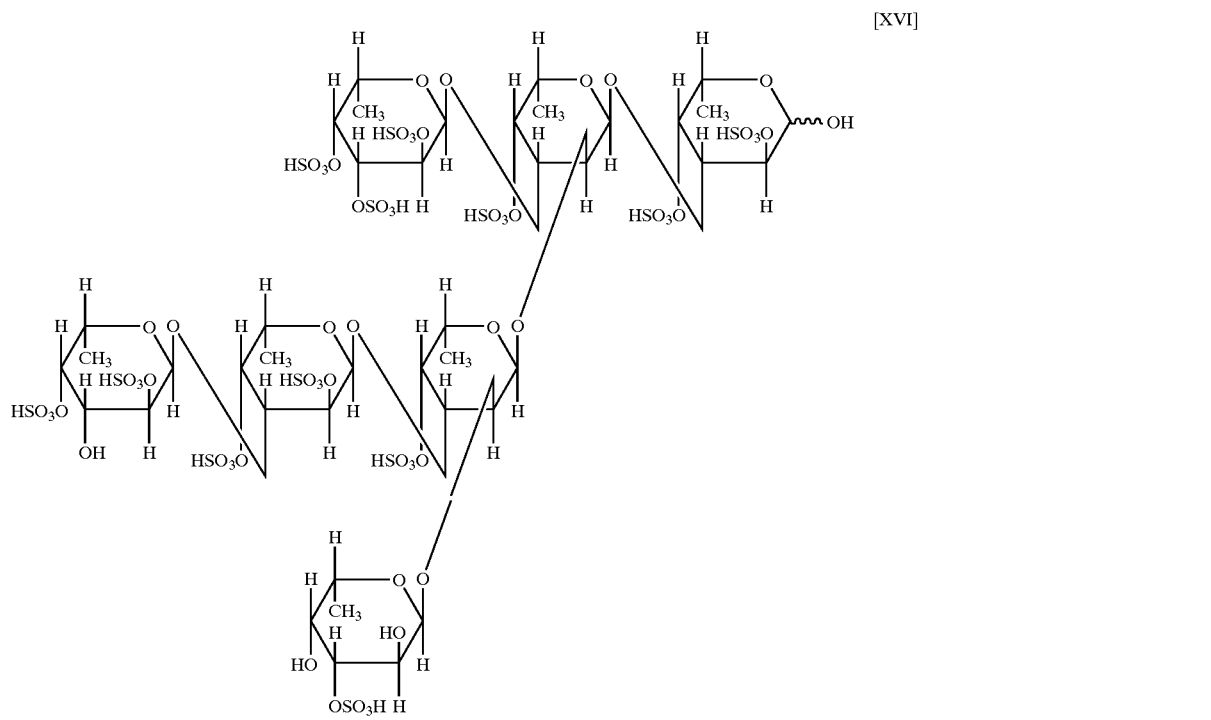

(3) The 0.6 M-eluted fraction from DEAE-Cellulofine as described in Example 9(2) was purified as described above for the 0.4 M-eluted fraction to obtain a lyophilization product.

Analysis of the product using HPLC demonstrated that the product was a sulfated saccharide having a higher molecular weight than that of the product contained in the 0.4 M-eluted fraction. NMR analysis of the product provided almost the same spectrum as that obtained for the 0.4 M-eluted fraction.

Figure 27:
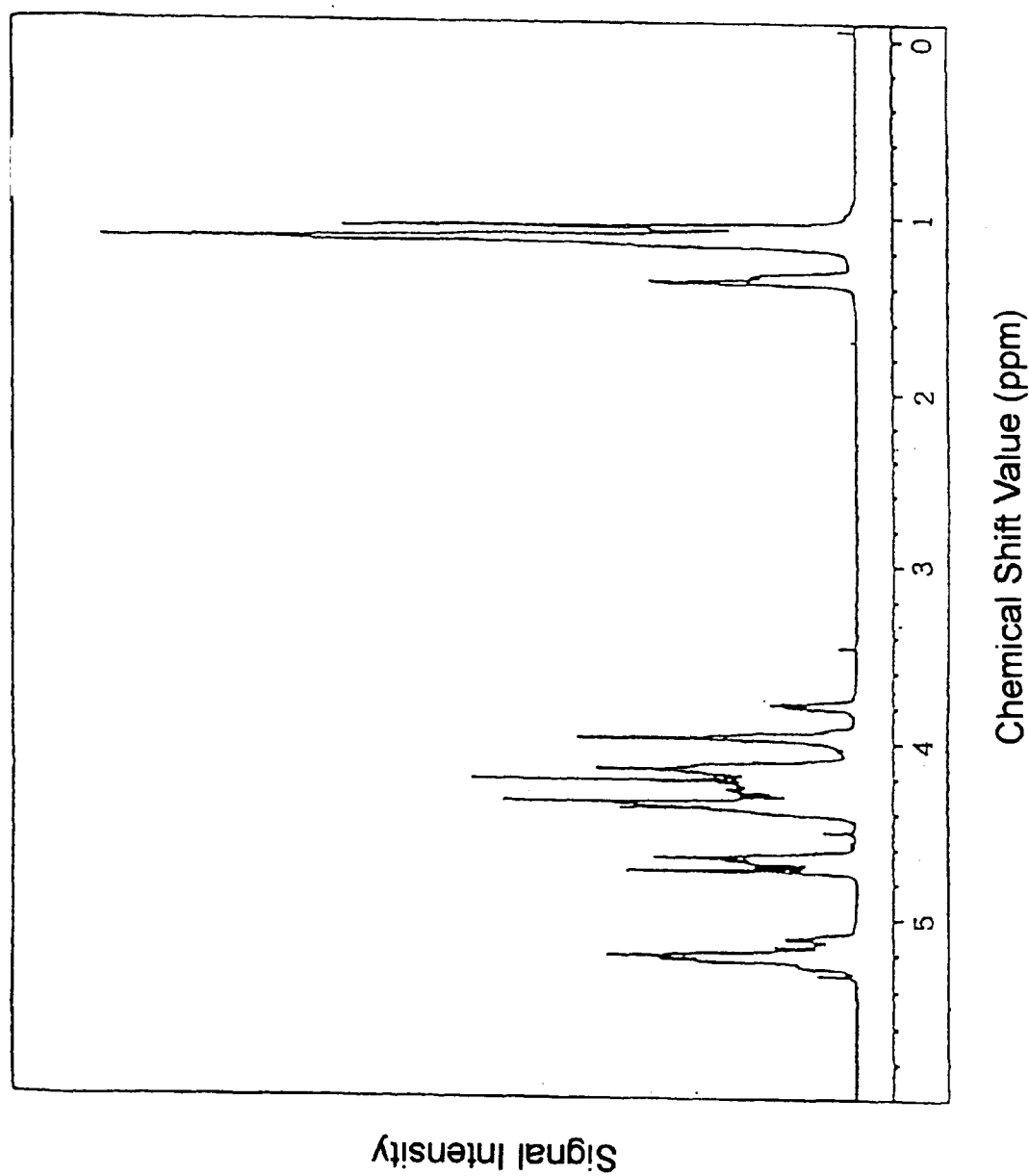
FIG. 27: a figure which illustrates the $^1$H-NMR spectrum of the fraction of the smaller molecule from the fucose sulfate-containing polysaccharide eluted with 0.6 M sodium chloride.

The $^1$H-NMR spectrum of the 0.6 M-eluted fraction is illustrated in FIG. 27. Heavy water was used as a solvent. The chemical shift values in $^1$H-NMR are expressed assuming the chemical shift value of dioxane as 3.53 ppm. The measurement was carried out at 60° C. FIG. 27 is a figure which illustrates the $^1$H-NMR spectrum of the 0.6 M-eluted fraction. The vertical axis represents the signal intensity and the horizontal axis represents the chemical shift value (ppm).

The results strongly suggested that the 0.6 M-eluted fraction had a structure in which several molecules of the 0.4 M-eluted fraction were bonded. When products obtained by further digesting the 0.6 M-eluted fraction with the sulfated-fucose-containing polysaccharide-F-digesting enzyme as described in Example 9(1) were analyzed using HPLC, many of the reaction products were eluted at the same position as that for the sulfated saccharide in the 0.4 M-eluted fraction from DEAE-Cellulofine as described in Example 9(2).

The HPLC was carried out as follows.
Column: Shodex SB802.5 (Showa Denko);
Column temperature: 25° C.;
Eluent: 50 mM sodium chloride containing 5 mM sodium azide; and
Detection: differential refractive index detector Shodex RI-71.

The molecular weight was determined by gel filtration using pullulan (Showa Denko) as a standard for the 0.6 M-eluted fraction and the 0.4 M-eluted fraction. As a result, it was demonstrated that the 0.4 M-eluted fraction had a molecular weight of about 8500 based on the molecular weight of pullulan, and the 0.6 M-eluted fraction had a molecular weight of about 26000 based on the molecular weight of pullulan, indicating that the 0.6 M-eluted fraction was a trimer of the sulfated saccharide in the 0.4 M-eluted fraction. Furthermore, detailed analysis of the $^1$H-NMR spectrum of the 0.6 M-eluted fraction demonstrated that each of the repeating heptasaccharides bonded to the position 3 of the fucose F in formula (XV) via an α-(1→3) bond. Furthermore, a pentamer of the sulfated saccharide of (XVI), i.e., the sulfated saccharide of general formula (XIV) below wherein n is 5, was obtained from the smaller molecules from the fucose sulfate-containing polysaccharide according to the above-mentioned method.

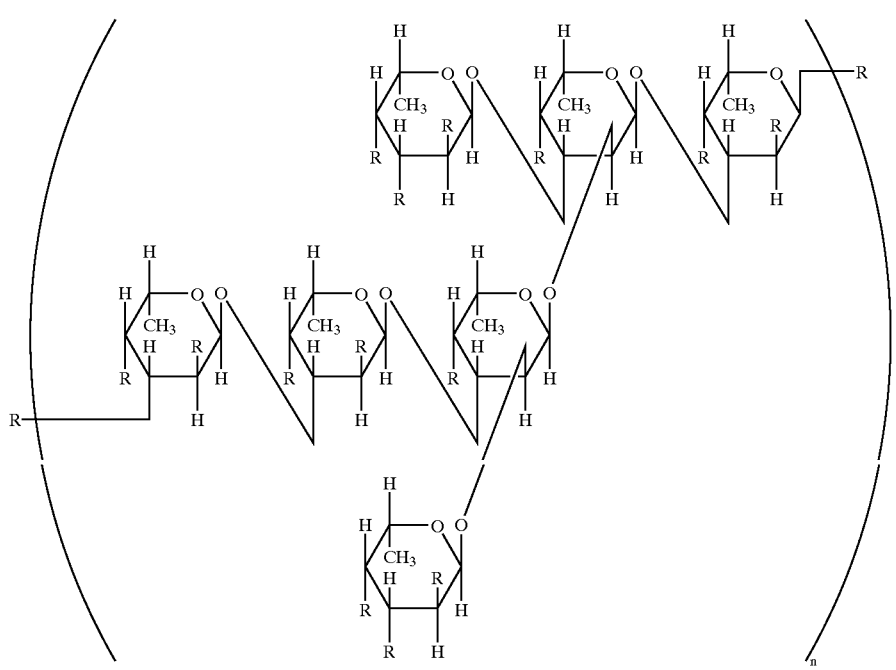

[XIV]

wherein R is H or OSO$_3$H.

As described above, it was confirmed that a sulfated polysaccharide which is converted into smaller molecules by the action of the sulfated-fucose-containing polysaccharide-F-digesting enzyme and which contains a sulfated saccharide of general formula below as an essential component of the constituting saccharide is obtained by treating a sulfated-fucose-containing polysaccharide obtained from brown algae such as Kjellmaniella crassifolia with the sulfated-fucose-containing polysaccharide-U-digesting enzyme and the sulfated fucogalactan-digesting enzyme of the present invention. The mean molecular weight of the sulfated polysaccharide was about 200,000 (molecular weight distribution: about 10,000 to about 1000,000) under extraction conditions at pH 6–8, at 95° C. for about 2 hours as measured according to the method described in Example 1(3). The mean molecular weight was about 13,000,000 (molecular weight distribution: about 100,000 to about 20,000,000) under extraction conditions at pH 6–8, at 25° C. for about 24 hours.

Industrial Applicability

The present invention provides a sulfated fucogalactan and a smaller molecule from the sulfated fucogalactan which are useful as reagents for glycotechnology or inducers of HGF production. The present invention also provides a novel sulfated fucogalactan-digesting enzyme which can be used for structural analysis and digestion of the sulfated fucogalactan and reproducible production of the smaller molecules from the sulfated fucogalactan. The present invention further provides a method for producing the enzyme. The present invention also provides a method for selectively removing the sulfated fucogalactan from a mixture of sulfated-fucose-containing polysaccharides using the sulfated fucogalactan-digesting enzyme of the present invention. Furthermore, the present invention provides a novel sulfated saccharide obtained by using the sulfated fucogalactan-digesting enzyme of the present invention in combination with other fucose sulfate-containing polysaccharide-digesting enzymes.

What is claimed is:

1. A sulfated fucogalactan having the following chemical and physical properties:
    (1) consisting of galactose and fucose as constituting saccharides at a molar ratio of 1:1 to 6:1;
    (2) containing a sulfated saccharide of general formula (XI) as an essential component of the constituting saccharides:

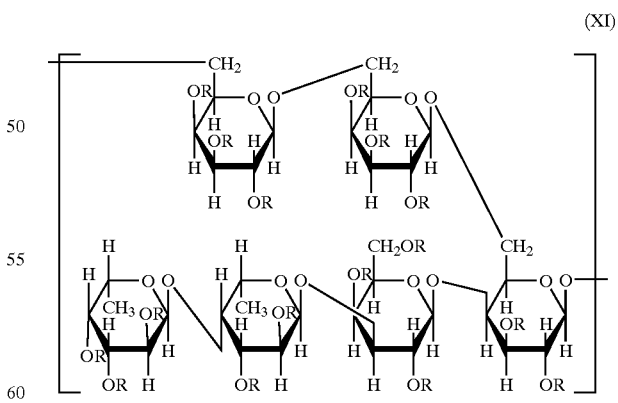

(XI)

wherein R is H or SO$_3$H; and
    (3) containing a sulfated saccharide that is capable of being converted into smaller molecules by a sulfated fucogalactan-digesting enzyme to generate at least one compound selected from the group consisting of the compounds of general formulas (I) to (IV):

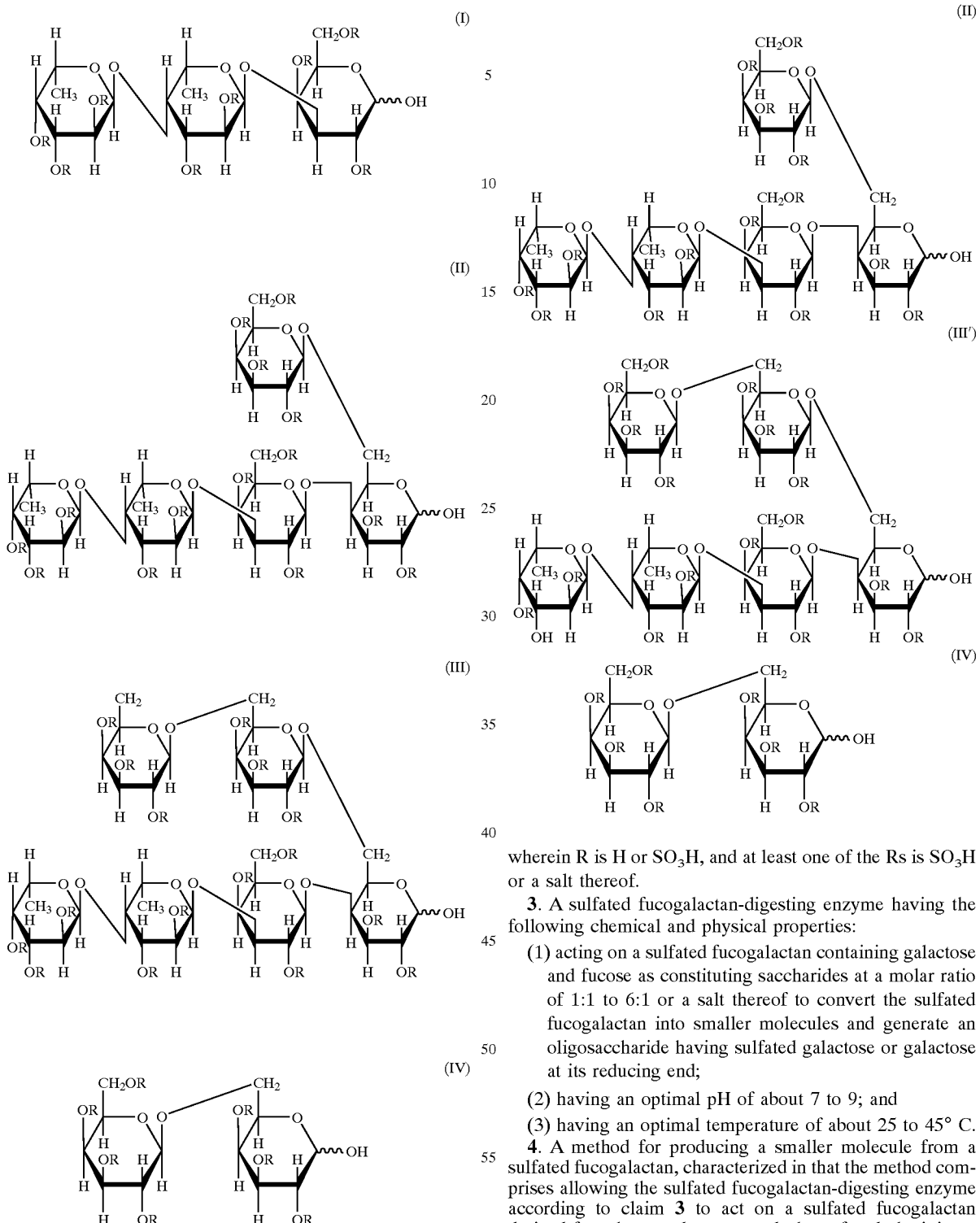

wherein R is H or SO₃H, or a salt thereof.

2. A saccharide having a chemical structure selected from the group consisting of general formulas (II), (III') and (IV):

wherein R is H or SO$_3$H, and at least one of the Rs is SO$_3$H or a salt thereof.

3. A sulfated fucogalactan-digesting enzyme having the following chemical and physical properties:

(1) acting on a sulfated fucogalactan containing galactose and fucose as constituting saccharides at a molar ratio of 1:1 to 6:1 or a salt thereof to convert the sulfated fucogalactan into smaller molecules and generate an oligosaccharide having sulfated galactose or galactose at its reducing end;

(2) having an optimal pH of about 7 to 9; and (3) having an optimal temperature of about 25 to 45° C.

4. A method for producing a smaller molecule from a sulfated fucogalactan, characterized in that the method comprises allowing the sulfated fucogalactan-digesting enzyme according to claim 3 to act on a sulfated fucogalactan derived from brown algae or a salt thereof and obtaining a smaller molecule.

5. A method for producing the sulfated fucogalactan-digesting enzyme according to claim 3, characterized in that the method comprises culturing a bacterium of genus Flavobacterium capable of producing the sulfated fucogalactan-digesting enzyme according to claim 3 and collecting the enzyme from the culture.

* * * * *